(12) United States Patent
Brabet et al.

(10) Patent No.: US 11,014,947 B2
(45) Date of Patent: May 25, 2021

(54) LIPOPHENOL COMPOUNDS AND USES THEREOF

(71) Applicants: INSTITUT NATIONAL DE LA SANTE ET DE LA RECHERCHE MEDICALE (INSERM), Paris (FR); CENTRE HOSPITALIER UNIVERSITAIRE DE MONTPELLIER, Montpellier (FR); UNIVERSITE D'AUVERGNE, Clermont-Ferrand (FR); UNIVERSITE DE MONTPELLIER, Montpellier (FR)

(72) Inventors: Philippe Brabet, Montpellier (FR); David Cia, Clermont-ferrand (FR); Laurent Guillou, Montpellier (FR); Christian Hamel, Montpellier (FR); Claire Vigor, Montpellier (FR); Thierry Durand, Montpellier (FR); Céline Crauste, Montpellier (FR); Joseph Vercauteren, Montpellier (FR)

(73) Assignees: INSERM (INSTITUT NATIONAL DE LA SANTE ET DE LA RECHERCHE MEDICALE), Paris (FR); CENTRE HOSPITALIER UNIVERSITAIRE DE MONTPELLIER, Montpellier (FR); UNIVERSITE D'AUVERGNE, Clermont-Ferrand (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/972,282

(22) Filed: May 7, 2018

(65) Prior Publication Data

US 2018/0273554 A1 Sep. 27, 2018

Related U.S. Application Data

(62) Division of application No. 15/303,797, filed as application No. PCT/EP2015/058960 on Apr. 24, 2015, now Pat. No. 10,011,620.

(30) Foreign Application Priority Data

Apr. 24, 2014 (EP) ..................... 14305607

(51) Int. Cl.
*C07F 9/10* (2006.01)
*C07C 69/587* (2006.01)
*C07C 69/017* (2006.01)
*C07B 59/00* (2006.01)

(52) U.S. Cl.
CPC .............. *C07F 9/10* (2013.01); *C07B 59/001* (2013.01); *C07B 59/004* (2013.01); *C07C 69/017* (2013.01); *C07C 69/587* (2013.01); *C07F 9/106* (2013.01); *C07B 2200/05* (2013.01)

(58) Field of Classification Search
CPC .......... C07F 9/10; C07F 9/106; C07B 59/001; C07B 59/004; C07C 69/017; C07C 69/587
USPC ....................................................... 514/770
See application file for complete search history.

(56) References Cited

FOREIGN PATENT DOCUMENTS

| CN | 1632865 A | 6/2005 | |
|---|---|---|---|
| JP | 10139718 | * 5/1998 | .............. C07C 57/03 |
| WO | 2005/069998 A2 | 8/2005 | |

OTHER PUBLICATIONS

Tonnies et al., Journal of Alzheimer's disease, 2017, 57, 1105-1121 (Year: 2017).*
Blessa et al., Frontiers in Neuroanatomy, 2015, vol. 9, article 91 (Year: 2015).*
Dias et al J Parkinsons Dis, 2013, 3(4), 461-491 (Year: 2013).*
JP 10139718 CAPLUS abstract (Year: 1998).*
Matsuyama et al: "Polyunsaturated Fatty Acid Anilides as Inhibitors of ACYL-COA: Cholesterol Acyltransferase (ACAT)", Bioorganic & Medicinal Chemistry Letters 9, pp. 2039-2042, 1999.
Cambridge Medchem, Bioisosteric Replacements, 2012.

* cited by examiner

*Primary Examiner* — Yevgeny Valenrod
(74) *Attorney, Agent, or Firm* — W&C IP

(57) ABSTRACT

The present invention relates to a compound of formula (I) wherein: i is 0 or 1; j is 0 or 1; k is 0 or 1; $R_1$ and $R_2$ are in particular H, ($C_1$-$C_{12}$)alkyl, or a group of formula C(O)R; R is a, linear or branched, alkyl radical, comprising at least 19 carbon atoms; $R_3$ is H and k=0 when j=1; or, when j=0, $R_3$ is —C(O)R or -L-C(O)R; L, L' and L" are linkers; wherein, when j=0, at least one of the groups $R_1$; $R_2$ and $R_3$ comprises a radical R.

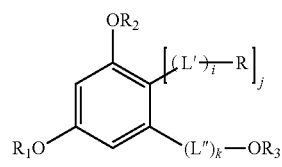

(I)

18 Claims, 10 Drawing Sheets

LIPOPHENOL COMPOUNDS AND USES THEREOF

CROSS-REFERENCE TO RELATED APPLICATIONS

Figure 1:
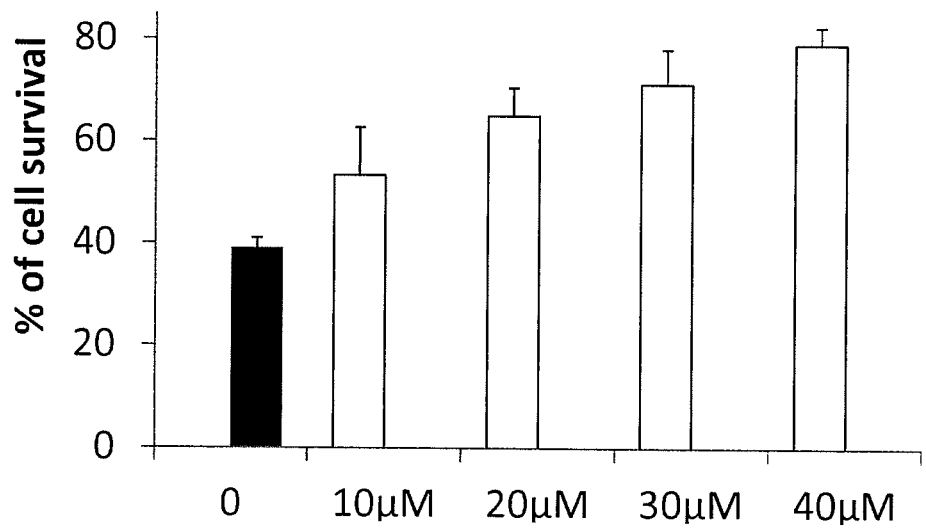

This application is a divisional application of USSN 15/303,797 filed Oct. 13, 2016, now U.S. Pat. No. 10,011,620, which itself was a Rule 371 filing from international application PCT/EP2015/058960 filed Apr. 24, 2015, and that international application claimed priority to European Patent Application 14305607.5 filed Apr. 24, 2014.

The present invention concerns new lipophenol compounds, their preparation processes, as well as uses thereof, especially for the treatment of neurodegenerative diseases.

Reactive carbonyl species, such as sugars, α-dicarbonyls or metabolites derived from lipid oxidation, are involved in glycation and cross-linking reactions of nucleophiles (like proteins—Maillard reactions), and thus affect cellular viability leading to tissue injuries. Aging-associated pathologies like age-related macular degeneration (AMD) but also other neurodegenerative diseases such as Alzheimer and Parkinson, result from carbonyl stress, strongly connected to oxidative stress.

Among those ones, retinal pathologies (AMD, namely) are a major public health issue in the world. Circumstantial evidences gathered over a number of years have implicated retinal pigment epithelial (RPE) lipofuscin in the aetiology of atrophic AMD and genetic macular degeneration like Stargardt disease. Major constituents of RPE lipofuscin are the bisretinoid conjugate A2E, its photoisomers and its oxidized metabolites. Pathologic A2E biosynthesis occurs when molecules of all-trans-retinal (AtR, key constituent of the visual cycle), rather than undergoing a detoxifying reduction to retinol, accumulate and react with phosphatidylethanolamine (PE) through a dual carbonyl and oxidative stress (COS) (N. L. Mata, J. Weng, G. H. Travis, *Invest. Ophthalmol. Vis. Sci.* 2000, 41, S144-S144; and J. R. Sparrow, E. Gregory-Roberts, K. Yamamoto, A. Blonska, S. K. Ghosh, K. Ueda, J. Zhou, *Prog. Retin. Eye Res.* 2012, 31, 121-135). This reactive aldehyde itself also presents a direct toxicity, involved in retinal dystrophy.

Thus, anti-COS derivatives, able to reduce the toxicity of the main carbonyl stressor, AtR, are proposed to reduce A2E formation and to slow down the pace of lipofuscin deposit. Recent literature addressed question of the ability of (poly)phenols, already known to be potent antioxidant, to also trap reactive toxic electrophilic carbonyl entities, showing them to be potent anti-carbonyl stressors (C. Y. Lo, W. T. Hsiao, X. Y. Chen, *J. Food Sci.* 2011, 76, H90-96; WO 2009/063440 and WO 2009/063439). One of them is represented by the phloroglucinol, monomer of the abundant phlorotannins in brown algae, active ingredient of commercialized spasmolytic drugs, and which has already been identified to reduce oxidative stress damages in cultured cells. Phloroglucinol efficiency to scavenge acrolein, 4-hydroxy-trans-2-nonenal (HNE) (two toxic α,β-unsaturated aldehydes derived from lipid peroxidation) and methylglyoxal) has been recently reported in physiological conditions. One disadvantage using such compound to treat retinal pathologies, is its low lipid solubility which would affect the bioavailability and reduce plasma concentrations.

There is thus a need for improving the efficiency of anti-COS derivatives, and especially for improving the bioavailability of such anti-COS derivatives.

An aim of the present invention is to provide novel compounds having an anti-COS activity.

Another aim of the present invention is to provide compounds having an anti-COS activity with an improved lipid solubility.

Another aim of the present invention is to provide compounds having an anti-COS activity with an improved bioavailability.

The present invention relates to compounds having the following formula (I):

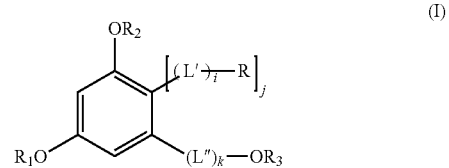

wherein:
i is 0 or 1;
j is 0 or 1;
k is 0 or 1;
$R_1$ is chosen from the group consisting of: H, $(C_1-C_{12})$alkyl, $(C_3-C_6)$cycloalkyl, and $(C_6-C_{10})$aryl radicals; or $R_1$ may form a heterocycloalkyl radical with the oxygen atom bearing it; or $R_1$ is a group of formula C(O)R, R being as defined below;
$R_2$ is chosen from the group consisting of: H, $(C_1-C_{12})$alkyl, $(C_3-C_6)$cycloalkyl, and $(C_6-C_{10})$aryl radicals; or $R_2$ may form a heterocycloalkyl radical with the oxygen atom bearing it; or $R_2$ is a group of formula C(O)R, R being as defined below;
R is a, linear or branched, alkyl radical, possibly interrupted by one or several double bonds, comprising at least 19 carbon atoms, and wherein one or several hydrogen atoms may be replaced by deuterium atoms;
$R_3$ is H and k=0 when j=1; or, when j=0, $R_3$ is a group of formula —C(O)R or —L—C(O)R, R being as defined above;
L is a linker having one of the following formulae (L1) or (L2):

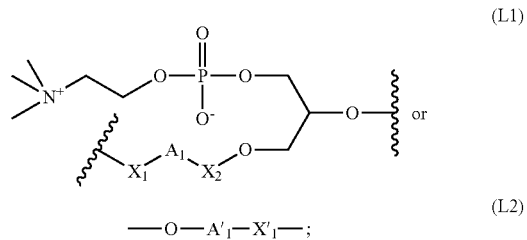

wherein:
$A_1$ is an alkylene radical comprising from 3 to 6 carbon atoms;
$A'_1$ is an alkylene radical comprising from 1 to 6 carbon atoms, optionally interrupted by one or several heteroatoms, such as oxygen atoms;
$X_1$ is a radical —C(O)— or an alkylene radical comprising from 1 to 6 carbon atoms;
$X_2$ is a radical —C(O)— or an alkylene radical comprising from 1 to 6 carbon atoms;
$X'_1$ is chosen from the group consisting of: —O—, —N($R_a$)— or an alkylene radical comprising from 1 to 6 carbon atoms, optionally interrupted by one or several heteroatoms, such as oxygen atoms, $R_a$ being H or an alkyl group comprising from 1 to 6 carbon atoms;

L' is a linker of formula $-(A)_p-(X)_q-C(O)-$, wherein:
p is 0 or 1;
q is 0 or 1;
A is an alkylene radical comprising from 1 to 6 carbon atoms, optionally interrupted by one or several heteroatoms, such as oxygen atoms,
X is —O—, —N($R_b$)— or an alkylene radical comprising from 1 to 6 carbon atoms, $R_b$ being H or an alkyl group comprising from 1 to 6 carbon atoms;

L" is a linker chosen from the group consisting of: $(C_6-C_{10})$arylene, $(C_1-C_{12})$alkylene, $(C_1-C_{12})$alkylene-$(C_6-C_{10})$arylene, $(C_6-C_{10})$arylene-$(C_1-C_{12})$alkylene, —CH=CH-$(C_6-C_{10})$arylene and $(C_1-C_{12})$alkylene-CH=CH-$(C_6-C_{10})$arylene radicals;

wherein, when j=0, at least one of the groups $R_1$, $R_2$ and $R_3$ comprises a radical R;

provided that the compound of formula (I) is other than the following compound:

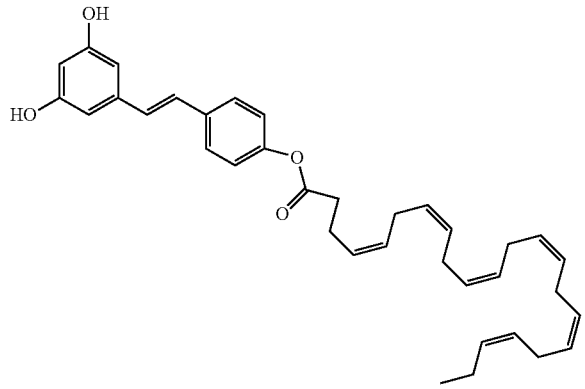 [SMILES: CC/C=C\C/C=C\C/C=C\C/C=C\C/C=C\C/C=C\CCC(=O)Oc1ccc(/C=C/c2cc(O)cc(O)c2)cc1]

or their pharmaceutically acceptable salts, racemates, diastereomers or enantiomers.

In the context of the present invention:
the expression "$C_t-C_z$" means a carbon-based chain which can have from t to z carbon atoms, for example $C_1-C_3$ means a carbon-based chain which can have from 1 to 3 carbon atoms;

the term "an alkyl group" means: a linear or branched, saturated, hydrocarbon-based aliphatic group comprising, unless otherwise mentioned, from 1 to 12 carbon atoms. By way of examples, mention may be made of methyl, ethyl, n-propyl, isopropyl, butyl, isobutyl, tert-butyl or pentyl groups;

the term "alkylene" (or "alkylidene") refers to a divalent hydrocarbon radical, which may be linear or branched, comprising from t to z carbon atoms, and in particular from 1 to 12 carbon atoms, and preferably from 1 to 6 carbon atoms. When said radical is linear, it may be represented by the formula $(CH_2)_k$ wherein k is an integer varying from t to z, and in particular from 1 to 12, and preferably from 1 to 6;

the term "a cycloalkyl group" means: a cyclic carbon-based group comprising, unless otherwise mentioned, from 3 to 6 carbon atoms. By way of examples, mention may be made of cyclopropyl, cyclobutyl, cyclopentyl, cyclohexyl, etc. groups;

the term "aryl group" means: a cyclic aromatic group comprising between 6 and 10 carbon atoms. By way of examples of aryl groups, mention may be made of phenyl or naphthyl groups;

the term "arylene" refers to an aromatic monocyclic, bicyclic or tricyclic hydrocarbon ring system comprising from 6 to 14 carbon atoms wherein any ring atom capable of substitution may be substituted by a substituent. A preferred arylene group is phenylene;

the term "a heterocycloalkyl" means: a 4- to 10-membered, saturated or partially unsaturated, monocyclic or bicyclic group comprising from one to three heteroatoms selected from O, S or N; the heterocycloalkyl group may be attached to the rest of the molecule via a carbon atom or via a heteroatom; the term bicyclic heterocycloalkyl includes fused bicycles and spiro-type rings.

By way of saturated heterocycloalkyl comprising from 5 to 6 atoms, mention may be made of oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridinyl, dioxanyl, morpholinyl, piperidinyl, piperazinyl, tetrahydrothiopyranyl, dithianyl, thiomorpholinyl or isoxazolidinyl.

When the heterocycloalkyl is substituted, the substitution(s) may be on one (or more) carbon atom(s) and/or on the heteroatom(s). When the heterocycloalkyl comprises several substituents, they may be borne by one and the same atom or different atoms.

The abovementioned "alkyl", "cycloalkyl", "aryl", and "heterocycloalkyl" radicals can be substituted with one or more substituents. Among these substituents, mention may be made of the following groups: amino, hydroxyl, thiol, oxo, halogen, alkyl, alkoxy, alkylthio, alkylamino, aryloxy, arylalkoxy, cyano, trifluoromethyl, carboxy or carboxyalkyl;

the term "a halogen atom" means: a fluorine, a chlorine, a bromine or an iodine;

the term "an alkoxy group" means: an —O-alkyl radical where the alkyl group is as previously defined. By way of examples, mention may be made of —O-$(C_1-C_4)$ alkyl groups, and in particular the —O-methyl group, the —O-ethyl group as —O-$C_3$alkyl group, the —O-propyl group, the -O-isopropyl group, and as —O-$C_4$alkyl group, the —O-butyl, —O-isobutyl or —O-tert-butyl group;

the term "an alkylthio" means: an —S-alkyl group, the alkyl group being as defined above;

the term "an alkylamino" means: an —NH-alkyl group, the alkyl group being as defined above;

the term "an aryloxy" means: an —O-aryl group, the aryl group being as defined above;

the term "an arylalkoxy" means: an aryl-alkoxy-group, the aryl and alkoxy groups being as defined above;

the term "a carboxyalkyl" means: an HOOC-alkyl-group, the alkyl group being as defined above. As examples of carboxyalkyl groups, mention may in particular be made of carboxymethyl or carboxyethyl;

the term "a carboxyl" means: a COOH group;

the term "an oxo" means: "=O".

When an alkyl radical is substituted with an aryl group, the term "arylalkyl" or "aralkyl" radical is used. The "arylalkyl" or "aralkyl" radicals are aryl-alkyl-radicals, the aryl and alkyl groups being as defined above. Among the arylalkyl radicals, mention may in particular be made of the benzyl or phenethyl radicals.

The compounds herein described may have asymmetric centers. Compounds of the present invention containing an asymmetrically substituted atom may be isolated in optically active or racemic forms. It is well-known in the art how to prepare optically active forms, such as synthesis from optically active starting materials. All chiral, diastereomeric, racemic forms and all geometric isomeric forms of a compound are intended, unless the stereochemistry or the isomeric form is specifically indicated.

The term "pharmaceutically acceptable salt" refers to salts which retain the biological effectiveness and properties of the compounds of the invention and which are not biologically or otherwise undesirable. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) J. Pharm. Sd, vol. 66, 1). For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

According to the present invention, in formula (I), R may be interrupted by one or several double bonds. In such embodiment, R may also be called an alkenyl radical, which is a hydrocarbon group formed when a hydrogen atom is removed from an alkene group.

Within the present application, R corresponds to a residue of a fatty acid (said fatty acid having the formula RCOOH).

According to a particular embodiment, the possible double bond(s) of R is(are) double bond(s) with the configuration Z.

The term "alkenyl" as employed herein includes partially unsaturated, nonaromatic, hydrocarbon groups.

According to an embodiment, in formula (I), R may comprise one or several deuterium atoms.

According to the present invention, in formula (I), $A'_1$ may be an alkylene radical comprising from 1 to 6 carbon atoms, interrupted by one or several heteroatoms, such as oxygen atoms. As an example, $A'_1$ may comprise one or several group(s) of formula —(OCH$_2$CH$_2$)—.

The compounds of the invention are lipophenol compounds and thus phenol derivatives. They comprise a phenyl group which may carry one or several phenol functions, each being possibly alkylated or acylated. Each compound according to the invention comprises at least one lipidic chain which corresponds to the R radical.

The compounds of the invention may also be called fatty acid-phenolic conjugates as they comprise a phenolic core on which is linked at least one fatty acid chain.

The present invention concerns active ingredients which are able to scavenge at the same time free radical and carbonyl stressors (anti-COS) and are thus intended for the treatment of diseases involving both carbonyl and oxidative stress.

According to the present invention, the compounds of formula (I) comprise at least one radical R.

When j=1, the compounds comprise necessarily a radical R on the phenyl group.

When j=0, at least one of the groups $R_1$, $R_2$ and $R_3$ comprises a radical R.

According to an embodiment, $R_3$ is a group of formula C(O)R.

According to an embodiment, $R_3$ is a group of formula C(O)R, and $R_1$ and $R_2$ are H.

According to an embodiment, $R_3$ is a group of formula C(O)R, and at least one of $R_1$ and $R_2$ is other than H.

According to an embodiment, $R_3$ is a group of formula C(O)R, $R_1$ is other than H and $R_2$ is H.

According to an embodiment, $R_3$ is a group of formula C(O)R, and $R_1$ and $R_2$ are alkyl groups as defined above.

According to an embodiment, in formula (I), when j=0, at most one of the groups $R_1$, $R_2$ and $R_3$ is H.

According to an embodiment, in formula (I), when j=0, at least one of the groups $R_1$, $R_2$ and $R_3$ is an alkyl group as defined above. Preferably, said alkyl group is an isopropyl group.

The present invention also relates to compounds having the following formula (I-1):

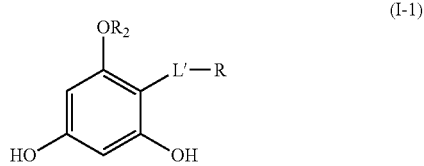

(I-1)

wherein L', R and $R_2$ are as defined above in formula (I), or their pharmaceutically acceptable salts, racemates, diastereomers or enantiomers.

The compounds of formula (I-1) correspond to compounds of formula (I) wherein i=1, j=1, k=0 and $R_1$ and $R_3$ are H.

According to an embodiment, in formula (I-1), $R_2$ is an alkyl group (Alk) as defined above in formula (I). Such compounds may be represented by the following formula:

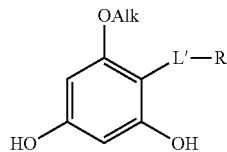

According to an embodiment, in formula (I-1), $R_2$ is H. Such compounds may be represented by the following formula:

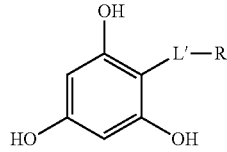

The present invention also relates to compounds having the following formula (I-1-1):

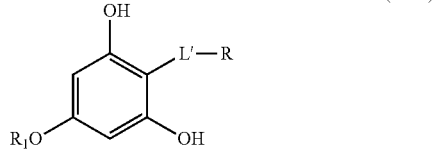

(I-1-1)

wherein L', R and $R_1$ are as defined above in formula (I), or their pharmaceutically acceptable salts, racemates, diastereomers or enantiomers.

The compounds of formula (I-1-1) correspond to compounds of formula (I) wherein i=1, j=1, k=0 and $R_2$ and $R_3$ are H.

According to an embodiment, in formula (I-1-1), $R_1$ is an alkyl group as defined above, and in particular an isopropyl group.

According to an embodiment, in formula (I-1-1), L' is a linker of formula -A-O—C(O)—, A being as defined above in formula (I). Preferably, L' is —(CH$_2$)$_3$—O—C(O)—.

The present invention also relates to compounds having the following formula (I-2):

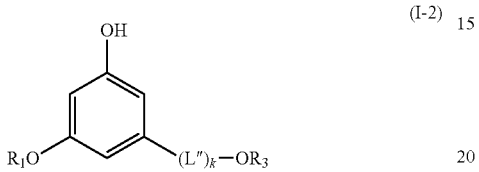

(I-2)

wherein k, L", $R_1$ and $R_3$ are as defined above in formula (I), or their pharmaceutically acceptable salts, racemates, diastereomers or enantiomers. In these compounds, the lipidic part (corresponding to the R group) is comprised in the $R_3$ group. Depending on the nature of $R_1$, it may also be comprised in this group (if $R_1$ is a group C(O)R).

The compounds of formula (I-2) correspond to compounds of formula (I) wherein j=0 and $R_2$ is H. Preferably, in formula (I-2), k=0. As above, compounds of formula (I-2) are other than the following compound

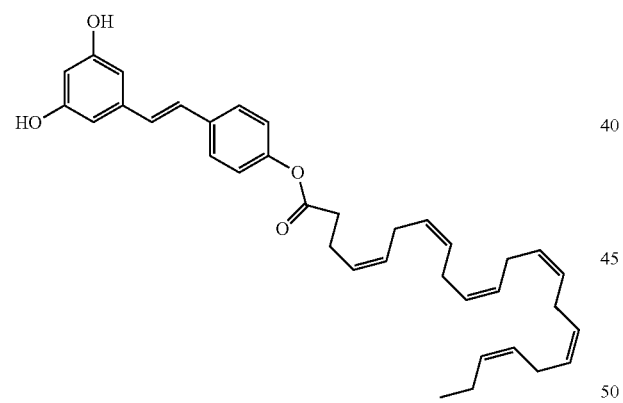

According to an embodiment, in formula (I-2), $R_1$ is H. Such compounds may be represented by the following formula:

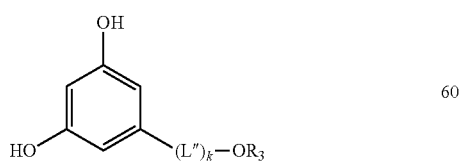

According to an embodiment, in formula (I-2), $R_1$ is an alkyl group (Alk) as defined above in formula (I). Such compounds may be represented by the following formula:

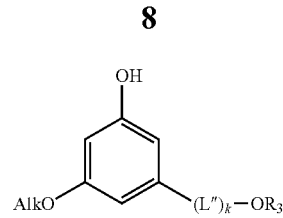

According to an embodiment, in formula (I-2), $R_3$ is a group of formula C(O)R, R being as defined above. Such compounds may be represented by the following formula:

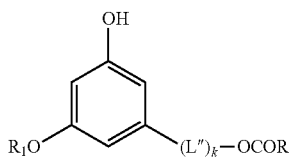

In this formula, k is preferably 0.

According to an embodiment, in formula (I-2), $R_1$ is H and $R_3$ is a group of formula C(O)R, R being as defined above. Such compounds may be represented by the following formula:

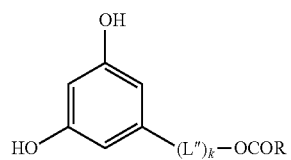

In this formula, k is preferably 0.

According to an embodiment, in formula (I-2), $R_1$ is an alkyl group (Alk) as defined above in formula (I) and $R_3$ is a group of formula C(O)R, R being as defined above. Such compounds may be represented by the following formula:

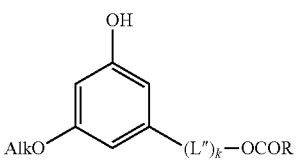

In this formula, k is preferably 0.

According to an embodiment, in formula (I-2), $R_1$ is an alkyl group (Alk) as defined above in formula (I), k=0 and $R_3$ is a group of formula C(O)R, R being as defined above. Such compounds have the following formula (I-2-1):

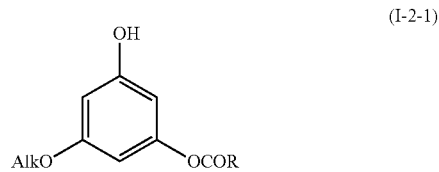

(I-2-1)

Preferably, in formula (I-2-1), Alk is a methyl, isopropyl or n-propyl group, and most preferably is an isopropyl group.

The present invention also relates to compounds having the following formula (I-5):

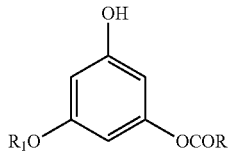 (I-5)

wherein R is as defined above in formula (I), and $R_1$ is an alkyl group comprising from 1 to 12 carbon atoms,
or their pharmaceutically acceptable salts, racemates, diastereomers or enantiomers.

The compounds of formula (I-5) correspond to compounds of formula (I) wherein j=0, k=0, $R_1$ is an alkyl group as defined above and $R_2$ is H.

The present invention also relates to compounds having the following formula (I-5-1):

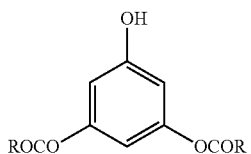 (I-5-1)

wherein R is as defined above in formula (I),
or their pharmaceutically acceptable salts, racemates, diastereomers or enantiomers.

The compounds of formula (I-5-1) correspond to compounds of formula (I) wherein j=0, k=0, $R_1$ and $R_3$ are OCOR as defined above and $R_2$ is H.

The present invention also relates to compounds having the following formula (I-6):

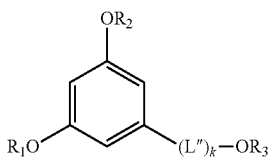 (I-6)

wherein k, L", $R_1$, $R_2$ and $R_3$ are as defined above in formula (I),
or their pharmaceutically acceptable salts, racemates, diastereomers or enantiomers.

The compounds of formula (I-6) correspond to compounds of formula (I) wherein j=0.

According to an embodiment, in formula (I-6), k=0. Such compounds may be represented by the following formula:

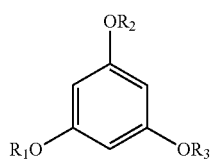 (I-6-1)

According to an embodiment, in formula (I-6) and (I-6-1), $R_3$ is C(O)R, R being as defined above. Such compounds may be represented by the following formula:

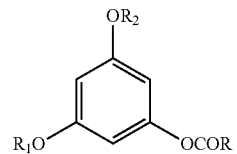

According to an embodiment, in formula (I-6) and (I-6-1), $R_1$ and $R_2$ are both alkyl groups as defined above.

According to an embodiment, in formula (I-6) and (I-6-1), $R_1$ and $R_2$ are both alkyl groups as defined above, and $R_3$ is C(O)R, R being as defined above.

According to an embodiment, in formula (I-6) and (I-6-1), $R_1$, $R_2$ are $R_3$ are C(O)R, R being as defined above.

The present invention also relates to compounds having the following formula (I-3)

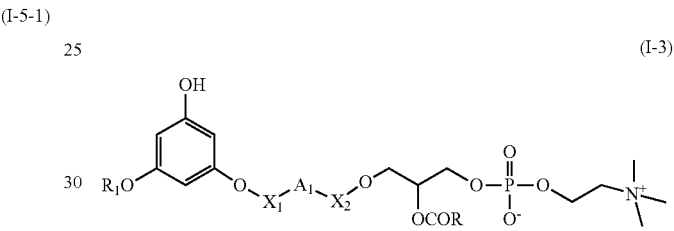 (I-3)

wherein $A_1$, $X_1$, $X_2$, R, and $R_1$ are as defined above in formula (I),
or their pharmaceutically acceptable salts, racemates, diastereomers or enantiomers.

The compounds of formula (I-3) correspond to compounds of formula (I) wherein j=0, k=0, $R_2$ is H, $R_3$ is -L-C(O)R, wherein R is as defined above and L is a linker of formula (L1).

According to an embodiment, in formula (I-3), $R_1$ is an alkyl group as defined above, and preferably an isopropyl group.

According to an embodiment, in formula (I-3), $X_1$ and $X_2$ are —C(O)—.

According to an embodiment, in formula (I-3), $A_1$ is a linear alkylene radical, preferably having 3 carbon atoms.

The present invention thus also relates to compounds having the following formula (I-3-1):

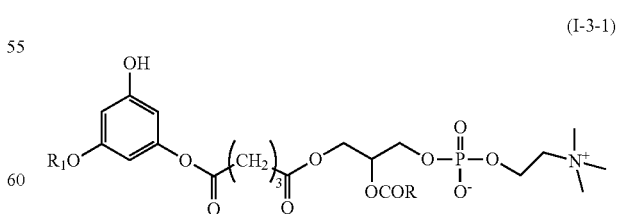 (I-3-1)

wherein R and $R_1$ are as defined above in formula (I), $R_1$ being preferably an alkyl group, such as an isopropyl group.

The present invention also relates to compounds having the following formula (I-4):

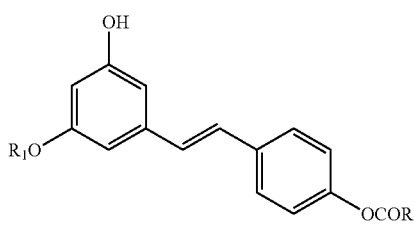

(I-4)

wherein R is as defined above in formula (I), and $R_1$ is an alkyl group comprising from 1 to 12 carbon atoms, preferably an isopropyl group, or their pharmaceutically acceptable salts, racemates, diastereomers or enantiomers.

Compounds of formula (I-4) correspond to compounds of formula (I) wherein j=0, k=1, $R_1$ is an alkyl group as defined above, $R_2$ is H, L" is —CH═CH-phenylene-, and $R_3$ is —C(O)R, wherein R is as defined above.

The present invention also relates to compounds having the following formula (I-4-1):

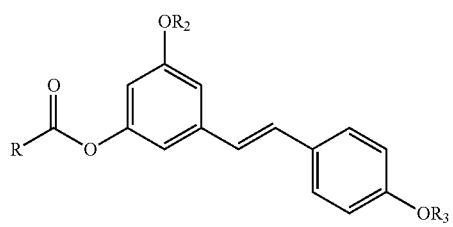

(I-4-1)

wherein

R is as defined above in formula (I), $R_2$ is H or an alkyl group comprising from 1 to 12 carbon atoms, $R_3$ is H or an alkyl group comprising from 1 to 12 carbon atoms, or their pharmaceutically acceptable salts, racemates, diastereomers or enantiomers.

Compounds of formula (I-4-1) correspond to compounds of formula (I) wherein j=0, k=1, $R_1$ is —C(O)R, wherein R is as defined above, $R_2$ is H or an alkyl group, L" is —CH═CH-phenylene-, and $R_3$ is H or an alkyl group.

According to an embodiment, in formula (I-4-1), $R_2$ is H.

According to an embodiment, in formula (I-4-1), $R_3$ is an alkyl group, preferably an isopropyl group.

According to an embodiment, in formula (I-4-1), $R_2$ is H, and $R_3$ is an alkyl group, preferably an isopropyl group.

According to an embodiment, in formula (I-4-1), $R_3$ is H.

According to an embodiment, in formula (I-4-1), $R_2$ is an alkyl group, preferably an isopropyl group.

According to an embodiment, in formula (I-4-1), $R_3$ is H, and $R_2$ is an alkyl group, preferably an isopropyl group.

The present invention also relates to compounds having the following formula (I-4-2):

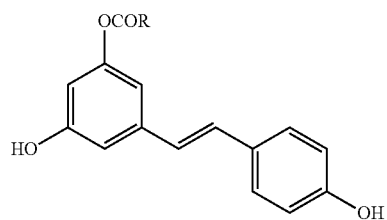

(I-4-1)

wherein R is as defined above in formula (I), or their pharmaceutically acceptable salts, racemates, diastereomers or enantiomers.

Compounds of formula (I-4-2) correspond to compounds of formula (I) wherein j=0, k=1, $R_1$ is H, $R_2$ is —C(O)R, wherein R is as defined above, L" is —CH═CH-phenylene-, and $R_3$ is H.

According to an embodiment, in formula (I), $R_1$ is a $(C_1$-$C_{12})$alkyl group, preferably a $(C_1$-$C_6)$alkyl group. According to a preferred embodiment, $R_1$ is an isopropyl group.

According to an embodiment, in the compounds of the invention, R is a linear or branched alkyl group, possibly interrupted by one or several double bonds, comprising from 19 to 23 carbon atoms. According to a preferred embodiment, R is a linear group.

According to an embodiment, in the compounds of the invention, R is a linear or branched alkyl group, possibly interrupted by one or several double bonds, comprising from 19 to 23 carbon atoms, and wherein one or several hydrogen atoms are replaced by deuterium atoms.

According to an embodiment, in the compounds of the invention, R is a linear or branched alkyl group, interrupted by at least one double bond, comprising from 19 to 21 carbon atoms.

According to an embodiment, in the compounds of the invention, R is a linear or branched alkyl group, interrupted by at least three double bonds, preferably at least five double bonds, comprising from 19 to 21 carbon atoms.

According to an embodiment, said double bonds have the configuration Z.

According to a preferred embodiment, R is a linear group.

According to an embodiment, in the compounds of the invention, R is the following radical:

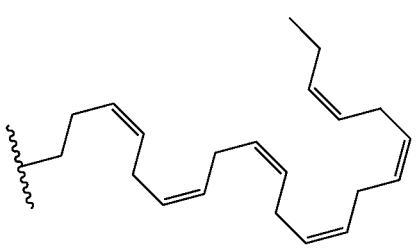 [SMILES: *CC/C=C\C/C=C\C/C=C\C/C=C\C/C=C\C/C=C\CC]

Such radical corresponds to the residue of docosahexaenoic acid (DHA).

According to an embodiment, in the compounds of the invention, R is the residue of eicosapentaenoic acid (EPA).

According to another embodiment, in the compounds of the invention, R is one of the following radicals:

13
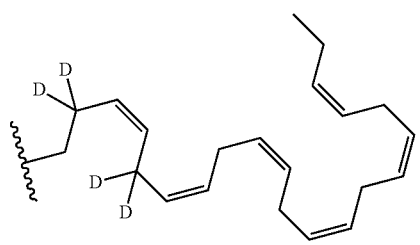 [SMILES: *CC([2H])([2H])/C=C\C([2H])([2H])/C=C\C/C=C\C/C=C\C/C=C\C/C=C\CC]
14
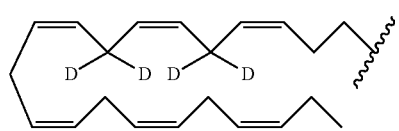 [SMILES: *CC/C=C\C([2H])([2H])/C=C\C([2H])([2H])/C=C\C/C=C\C/C=C\C/C=C\CC]
The preferred compounds according to the invention are as follows:
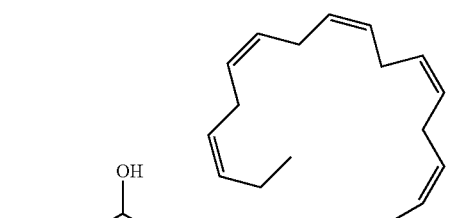
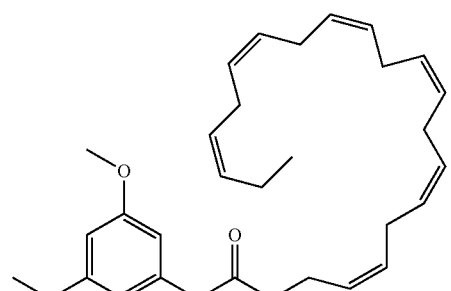
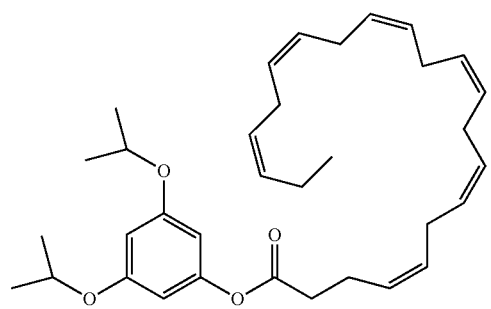
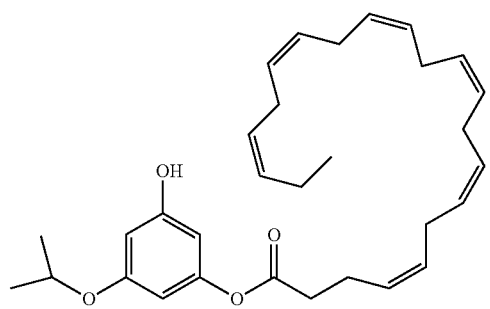
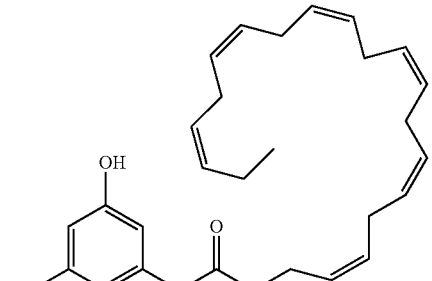
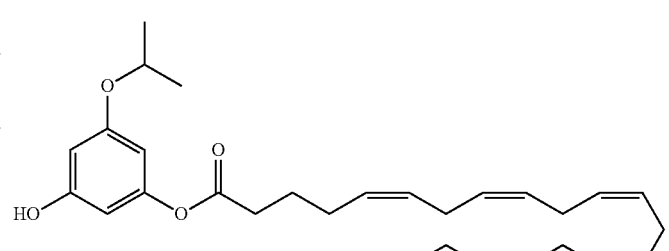
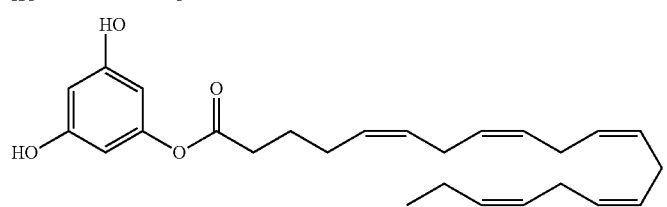
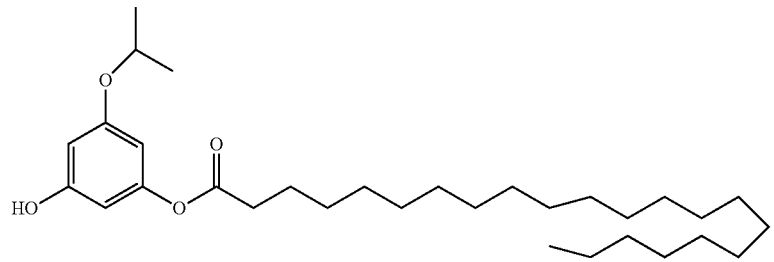

-continued
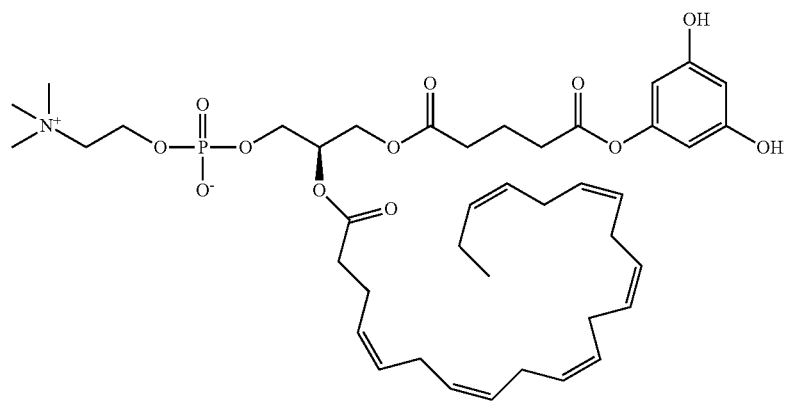
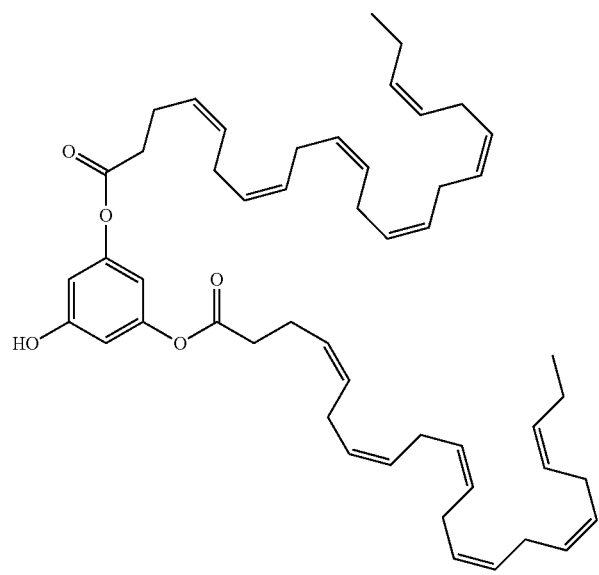
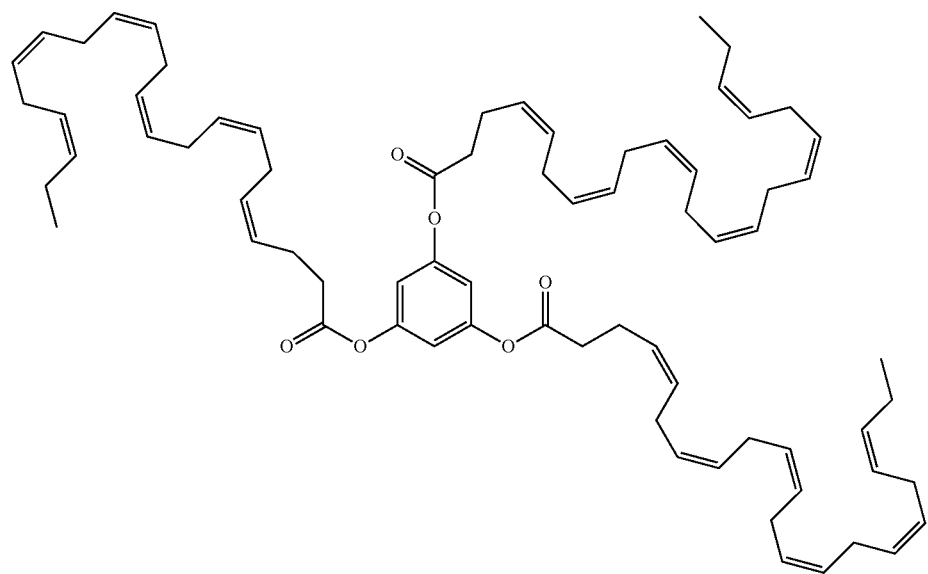

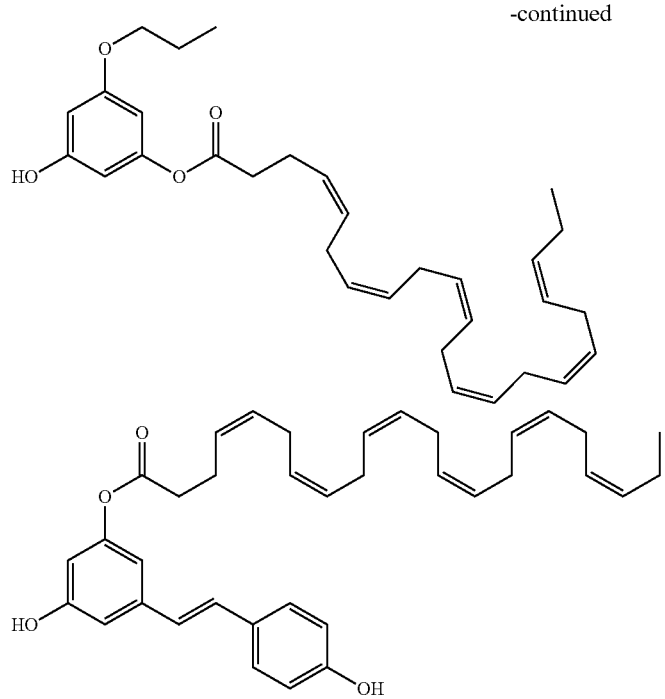
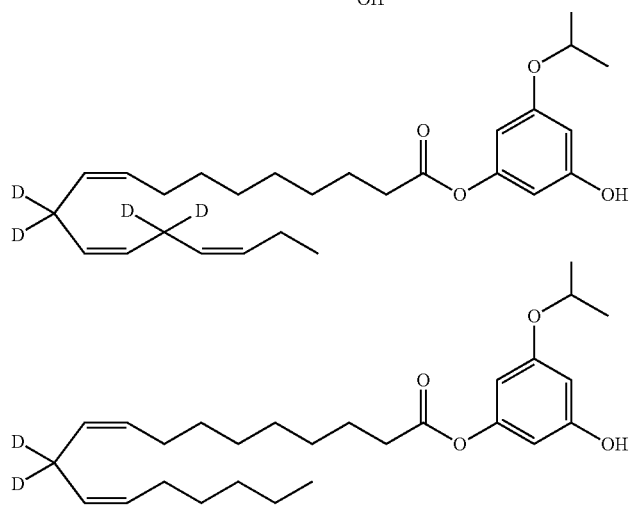
The present invention also relates to a process for preparing a compound having the formula (I-2-1) as defined above,
said process comprising:
a step of reacting a fatty acid RCOOH with a compound having the following formula (A-1):
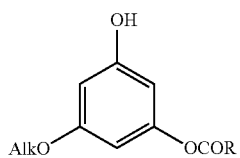
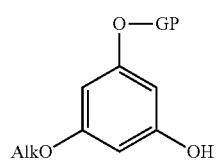
(A-1)
GP being a hydroxyl protecting group, in particular TIPS (triisopropylsilyl),
for obtaining a compound of formula (A-2):
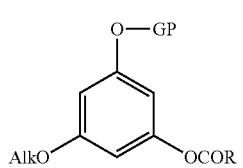
(A-2)

said step being in particular carried out in a solvent, such as dichloromethane, in the presence of DCC/DMAP, preferably at room temperature,
the duration of this step being preferably carried out for 5 hours, and
a step of deprotection of compound (A-2) for obtaining a compound of formula (I-2-1).

The present invention also relates to a process for preparing compounds having the following formula (B-1):

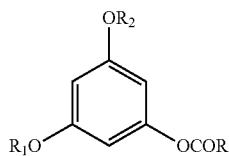
(B-1)

wherein $R_1$ and $R_2$ are alkyl groups,
said process comprising a step of reacting a fatty acid RCOOH with a compound having the following formula (B-2):

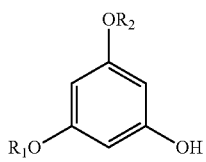
(B-2)

said step being in particular carried out in a solvent, such as dichloromethane, in the presence of DCC/DMAP, preferably at room temperature,
the duration of this step being preferably carried out for 5 hours.

The present invention also relates to a process for preparing a compound having the formula (C-1) as defined above,

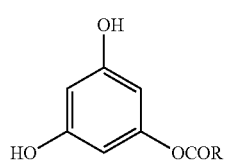
(C-1)

said process comprising:
a step of reacting a fatty acid RCOOH with a compound having the following formula (C-2):

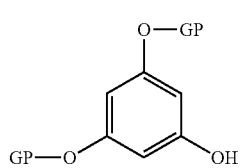
(C-2)

GP being a hydroxyl protecting group, in particular TIPS (triisopropylsilyl), for obtaining a compound of formula (C-3):

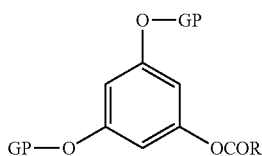
(C-3)

said step being in particular carried out in a solvent, such as dichloromethane, in the presence of DCC/DMAP, preferably at room temperature,
the duration of this step being preferably carried out for 5 hours, and
a step of deprotection of compound (C-3) for obtaining a compound of formula (C-1).

The present invention also relates to a process for preparing a compound having the formula (D-1) as defined above,

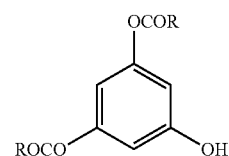
(D-1)

said process comprising:
a step of reacting a fatty acid RCOOH with a compound having the following formula (D-2):

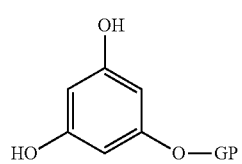
(D-2)

GP being a hydroxyl protecting group, in particular TIPS (triisopropylsilyl),
for obtaining a compound of formula (D-3):

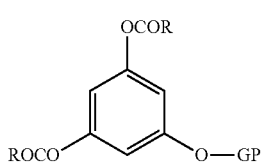
(D-3)

said step being in particular carried out in a solvent, such as dichloromethane, in the presence of DCC/DMAP, preferably at room temperature,
the duration of this step being preferably carried out for 5 hours, and
a step of deprotection of compound (D-3) for obtaining a compound of formula (D-1).

The present invention also relates to a process for preparing a compound having the formula (E-1) as defined above,

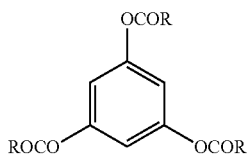

(E-1)

said process comprising reacting a fatty acid RCOOH with a compound having the above-mentioned formula (D-1), said step being in particular carried out in a solvent, such as dichloromethane, in the presence of DCC/DMAP, preferably at room temperature, the duration of this step being preferably carried out for 5 hours.

The compounds of formula (E-1) may also be prepared by reacting the fatty acid with phloroglucinol in the same operating conditions as described above.

The present invention also relates to a process for preparing a compound having the formula (F-1)

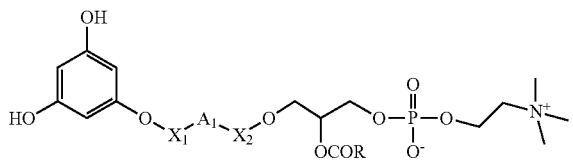

(F-1)

wherein $X_1$, $A_1$, $X_2$ and R are as defined above in formula (I-3), said process comprising:

a step of reacting a compound having the following formula (F-2):

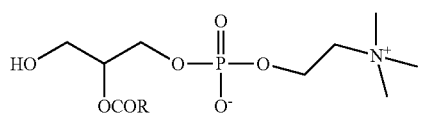

(F-2)

with a compound having the following formula (F-3):

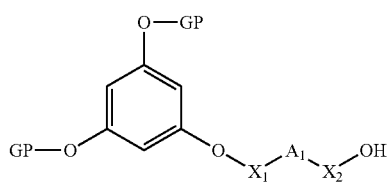

(F-3)

GP being a hydroxyl protecting group, in particular TIPS (triisopropylsilyl), for obtaining a compound of formula (F-4):

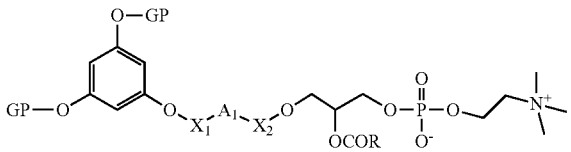

(F-4)

and a step of deprotection of compound (F-4) for obtaining compound of formula (F-1) as defined above.

In the above-mentioned processes, the steps of deprotection may be carried out by implementing well-known methods for the skilled person.

The present invention also relates to a pharmaceutical composition comprising a compound according to the invention, in association with a pharmaceutically acceptable vehicle.

The present invention relates to a pharmaceutical composition comprising a compound having one of the formulae as mentioned above, and in particular having formula (I), (I-1), (I-1-1), (I-2), (I-2-1), (I-3), (I-3-1), (I-4), (I-4-1), (I-5), (I-5-1), (I-6) or (I-6-1), in association with a pharmaceutically acceptable vehicle.

The present invention also relates to a drug, comprising a compound having formula (I) as defined above.

While it is possible for the compounds of the invention having formula (I) to be administered alone, it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and possibly other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not to be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The present invention also relates to the compound of formula (I) as defined above, for its use for the treatment of a pathology involving both carbonyl and oxidative stress.

According to the present invention, the term "pathology involving both carbonyl and oxidative stress" refers to a pathology (or disease) which involves abnormal alkylation of important intra or extracellular biological molecules: proteins, nucleic acids, glutathione, ethanolamine and many other ones like. This deleterious bond formation being due either to the reaction between nucleophilic functions of these molecules with reactive electrophiles (carbonyl species), thus said the carbonyl stress (leading to glycation or Maillard reactions), or as well as to oxidant reactive oxygen species (ROS), thus said theoxidative stress.

In the context of the invention, the term "carbonyl stress" is the abnormal metabolism resulting from the enhanced electrophilic reactivity of carbonyl species, said the carbonyl stressors, such as osides (glucose, fructose, and like) and their derivatives (osones, glyoxal, methylglyoxal, glyoxylic acid and like), but also, such as the aldehydes formed upon lipid peroxidation (malondialdhyde, 4-hydroxynonenal =4-HNE, and like).

A compound according to the invention has an anti-carbonyl stress activity because is able to efficiently reduce carbonyl stressor toxicity. It could then limit the formation of pathological glycated products such as lipofuscins.

In the context of the invention, the term "oxidative stress" is the result of an abnormal radical oxidation reaction taking place when a ROS is formed upon electron leakage during the respiration process. If this occurs in the bilayer membranes and in the presence of dioxygen, the alkyl radical oxidizes to the alkylperoxide radical which further reacts by abstracting one proton and one electron to another lipid of the membrane, which starts a chain oxidation reaction. This oxidative stress not only causes new bond formation or the breaking down of the lipids, but also the harmful peroxidation processes, eventually leading to inflammation through the ecosanoid cascade and the release of the cytokines.

A compound according to the invention has an anti-oxidative stress activity and is able to scavenge oxidative stressors (ROS), and thus to avoid the formation of the toxic oxidation products and the inflammatory response, to quench any chain oxidation reaction, thus, in case of Stargardt disease, the production of the lipofuscin A2E.

According to the present invention, the pathology involving carbonyl and oxidative stress may be chosen from the group consisting of: inflammatory and infectious diseases, cardiovascular diseases, metabolic diseases, cancer, retinal pathologies, and neurodegenerative diseases.

According to the present invention, the term "inflammatory diseases" refers to diseases characterized by a chronic inflammation. By "inflammation" is meant the phenomena by which the human body usually defends itself against aggression and which can manifest itself in various symptoms such as swelling, heat or redness of the skin.

In the context of the invention, the term "infectious disease" refers to a disease caused by pathogenic microorganisms, such as bacteria, viruses, parasites or fungi. Infectious diseases include influenza (or flu).

In the context of the invention, a "cardiovascular disease" refers to a disease that involves the heart or blood vessels (arteries and veins). More particularly, a cardiovascular disease according to the invention denotes a disease, lesion or symptom associated with an atherogenesis process that affects the cardiovascular system. It includes especially the conditions in which an atheroma plaque develops as well as the complications due to the formation of an atheroma plaque (stenosis, ischemia) and/or due to its evolution toward an acute ischemic stroke (thrombosis, embolism, infarction, arterial rupture).

Cardiovascular diseases include coronary artery disease, coronary heart disease, hypertension, atherosclerosis, in particular iliac or femoral atherosclerosis, angina pectoris, thrombosis, heart failure, stroke, vascular aneurysm, vascular calcification, myocardial infarction, cardiac dysrhythmia, vascular stenosis and infarction, and vascular dementia.

In the context of the invention, a "metabolic disease" denotes a disease that disrupts normal metabolism. Preferably, the metabolic disease according to the invention is a carbohydrate metabolism disorder.

As used herein a "carbohydrate metabolism disorder" denotes a disease wherein the metabolism of carbohydrate, for example of glucose, is disrupted. Carbohydrate metabolism disorders include diabetes, such as type II diabetes, high fasting glycemia, overweight and obesity.

According to the present invention, by the term "cancer" is meant malignant solid tumors and/or disseminated hematological cancers and/or their metastasis. The terms "metastasis" or "metastatic diseases" refer to secondary malignant tumors that are formed by cells from a primary malignant tumor, which have moved to another localization. The term "hematological cancers" refers to types of cancer that affect blood, bone marrow, and lymph nodes such as myelomas, lymphomas or leukemias.

In the context of the invention, the term "retinal pathology" refers to a disease or disorder of the retina.

The retina pathologies include Stargardt disease which is a hereditary retinal dystrophia linked to mutations of a gene encoding a lipidic (retinal) carrier of ATP-Binding Cassette subtype A4 (ABCA4) (Allikmets et al., 1997).

The term "neurodegenerative disease" is used throughout the specification to identify a disease which is caused by damage to the central nervous system and can be identified by neuronal death. The neuronal cell death observed in a neurodegenerative disease is often preceded by neuronal dysfunction, sometimes by several years. Accordingly, the term "neurodegenerative disease" includes a disease or disorder that is characterized by neuronal dysfunction and eventually neuronal cell death. Exemplary neurodegenerative diseases include HIV-associated Dementia, multiple sclerosis, Alzheimer's Disease, Parkinson's Disease, amyotrophic lateral sclerosis, and Pick's Disease.

The present invention also relates to the compound of formula (I) as defined above, for its use for the treatment of a pathology involving both carbonyl and oxidative stress, chosen from the group consisting of: atherosclerosis, type II diabetes, cancer, Alzheimer's disease, Parkinson's disease, Age-related Macular Degeneration (AMD), Stargardt disease, and severe influenza viruses.

The present invention also relates to the use of a compound of formula (I) for the preparation of a medicament for the prevention and/or treatment of a pathology involving both carbonyl and oxidative stress, said pathology being chosen from the group consisting of: inflammatory and infectious diseases, cardiovascular diseases, metabolic diseases, cancer, retinal pathologies, and neurodegenerative diseases.

The present invention also relates to a method of prevention and/or treatment of a disease selected from the group consisting of: inflammatory and infectious diseases, cardiovascular diseases, metabolic diseases, cancer, retina pathologies, and neurodegenerative diseases, comprising the administration of a pharmaceutical acceptable amount of a compound of formula (I) defined above to a patient in need thereof.

In the context of the invention, the term "treating" or "treatment", as used herein, means reversing, alleviating, inhibiting the progress of, or preventing the disorder or condition to which such term applies, or one or more symptoms of such disorder or condition.

FIGURES

FIG. 1 concerns dose-response results of compound 13b. It represents ARPE-19 cell survival in the presence of AtR (25 µM).

Figure 2:
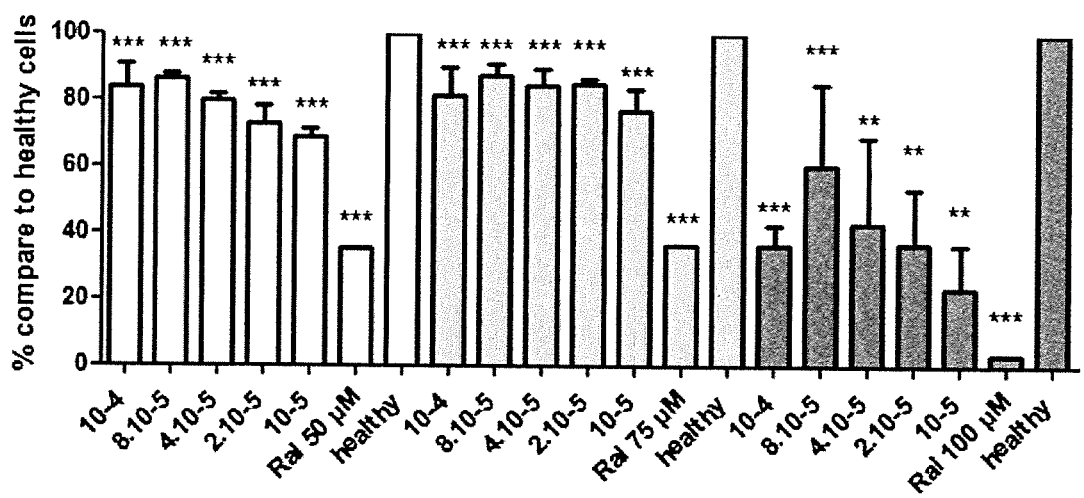

FIG. 2 concerns the dose-dependent protection of compound 13b of neural retina cell cultures exposed to atRal (: $P<0.005$ and *: $P<0.0005$). The white columns correspond to cells incubated with 50 µM atRal, the grey columns correspond to cells incubated with 75 µM atRal and the black columns correspond to cells incubated with 100 µM atRal.

Figure 3:
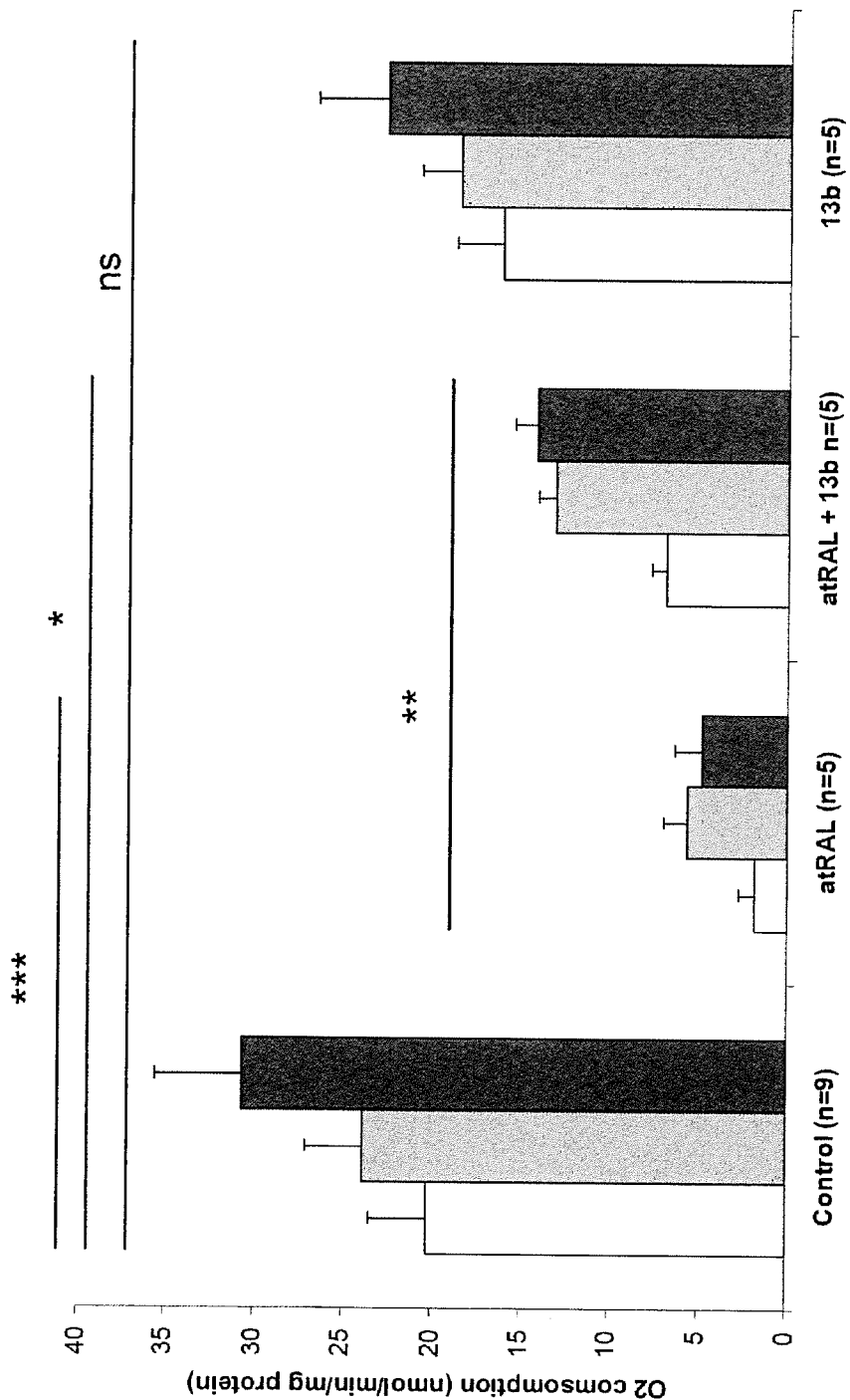

FIG. 3 concerns the mitochondrial respiration in ARPE-19 cells (*: $P<0.05$, : $P<0.005$, *: $P<0.0005$ and ns: not significant) exposed to atRal, in presence or absence of 13b. The white columns correspond to the inhibition of complex CI, the hatched columns correspond to the inhibition of complex CII, and the black columns correspond to the inhibition of both complexes.

Figure 4:
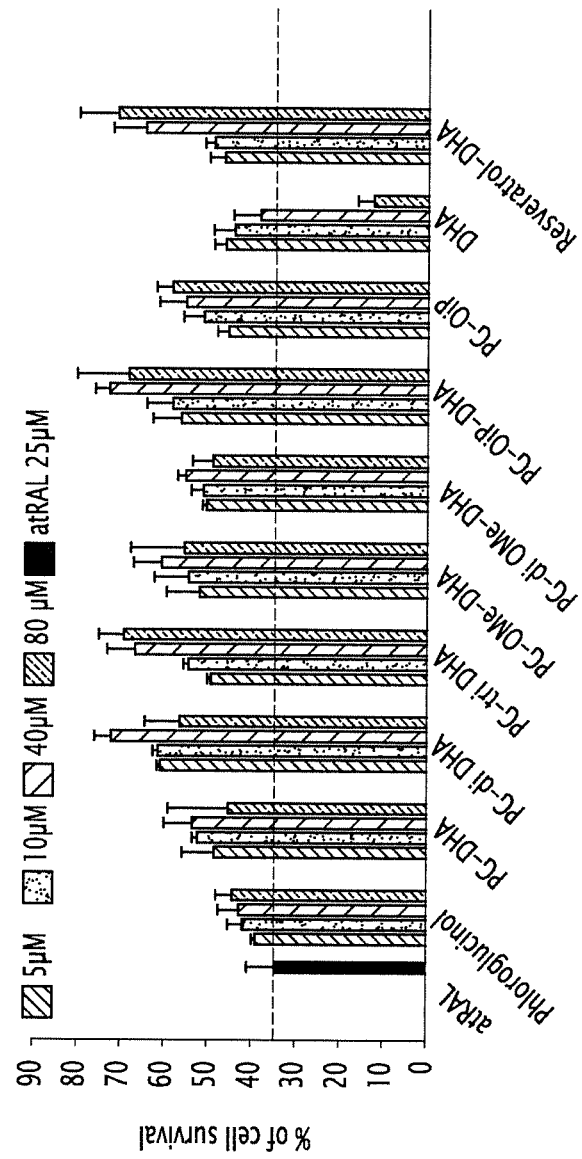

FIG. 4 concerns the dose-dependent protection of several compounds of the invention of ARPE-19 cell cultures exposed to atRal, in condition to prove their scavenging properties (Co-treatment). It represents ARPE-19 cell survival in the presence of AtR (25 µM) for several doses of each compound (5 µM, 10 µM, 40 µM, and 80 µM). PG-DHA corresponds to compound 6, PG-di DHA corresponds to compound 7, PG-tri DHA corresponds to compound 8, PG-OMe-DHA corresponds to compound 13a, PG-di OMe-DHA corresponds to compound 15a, and PG-OiP-DHA corresponds to compound 13b.

Figure 5:
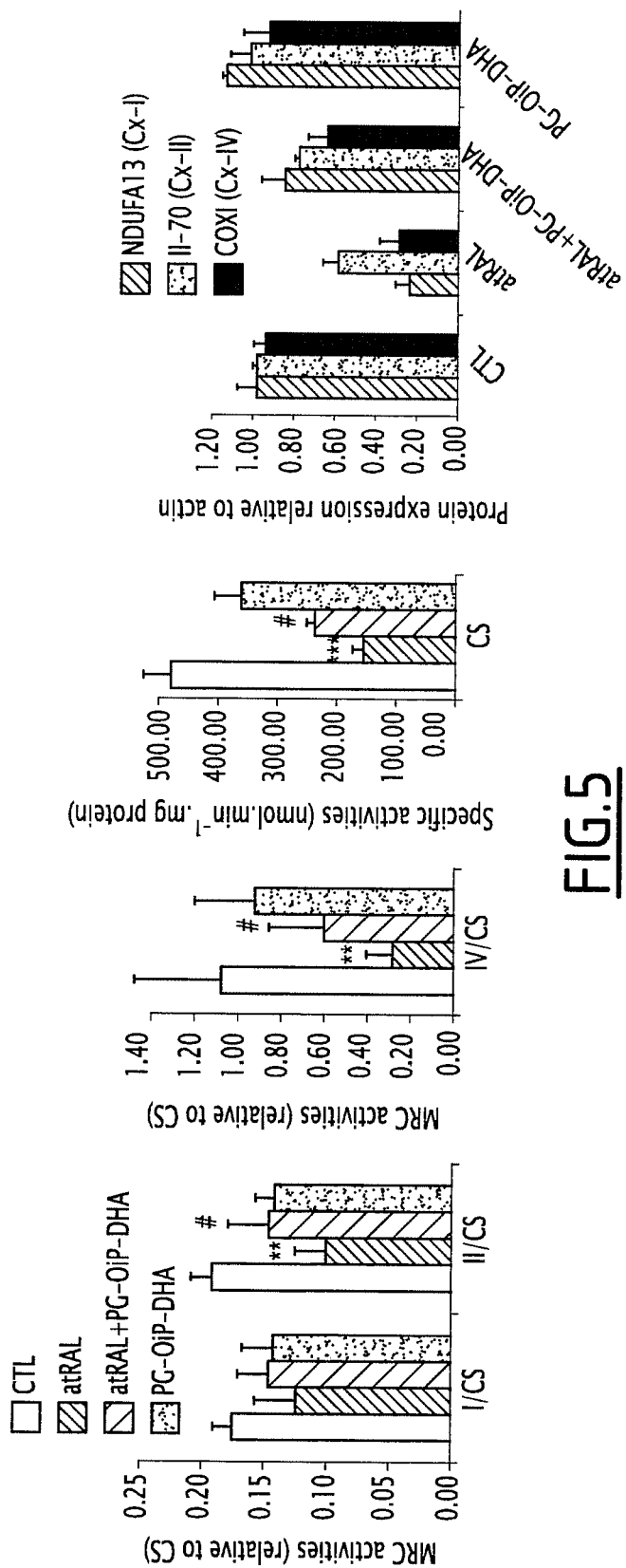

FIG. 5 concerns the measure of the intrinsic activity of each mitochondrial respiratory chain (MRC) complex (enzymology) and their level of protein expression.

Figure 6:
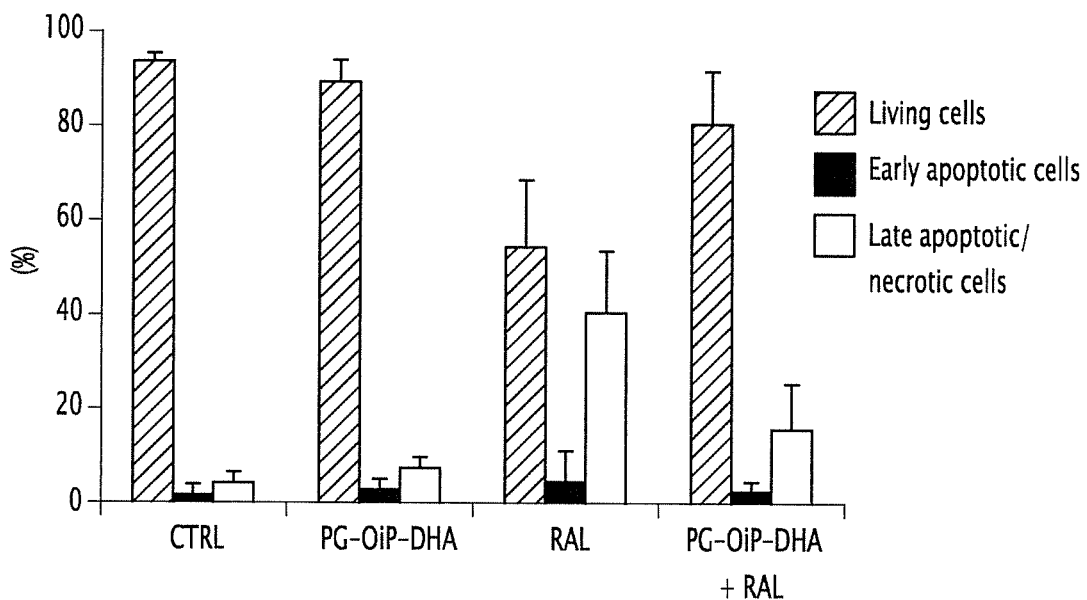

FIG. 6 concerns the characterization of atRAL-induced cell death. The columns with hatchings represent the percentage of living ARPE-19 cells, the columns in black represent the percentage of early apoptotic cells and the white columns represent the percentage of late apoptotic/necrotic cells.

Figure 7:
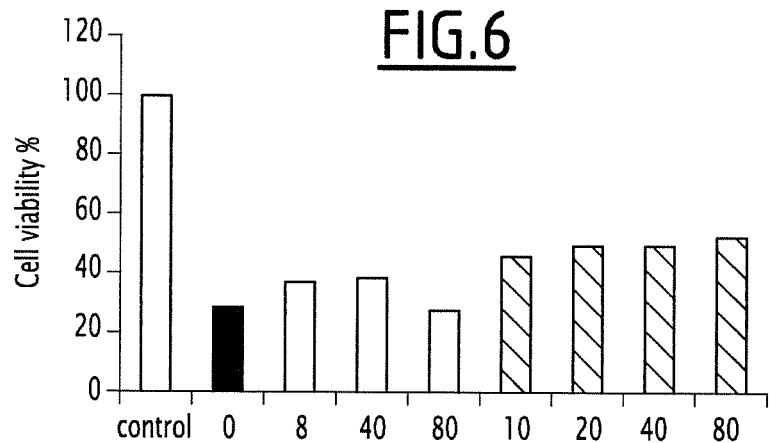

FIG. 7 relates to the comparison of the anti-oxidant efficacies of phloroglucinol (white columns) and PG-OiP-DHA (hatched columns) in RPE primary cells. It represents the cell viability (%) for these compounds at different concentrations.

Figure 8:
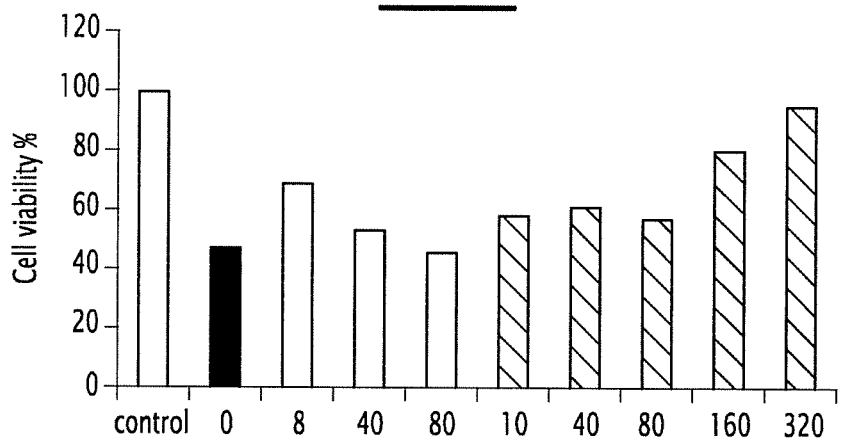

FIG. 8 relates to the comparison of the anti-carbonyl efficacies of phloroglucinol (white columns) and PG-OiP-DHA (hatched columns) in RPE primary cells. It represents the cell viability (%) for these compounds at different concentrations.

Figure 9:
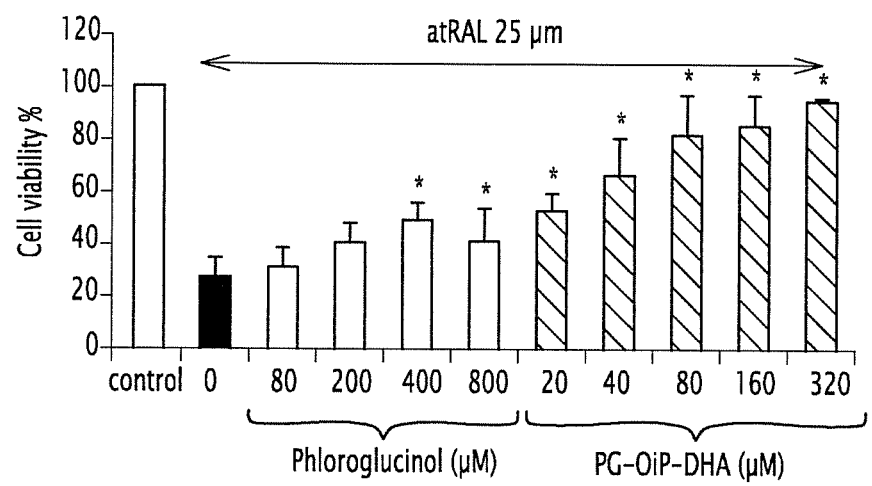

FIG. 9 relates to the comparison of the anti-carbonyl efficacies of phloroglucinol (white columns) and PG-OiP-DHA (hatched columns) in condition to prove their scavenging properties (Co-treatment), in RPE primary cells. It represents the cell viability (%) for these compounds at different concentrations.

Figure 10:
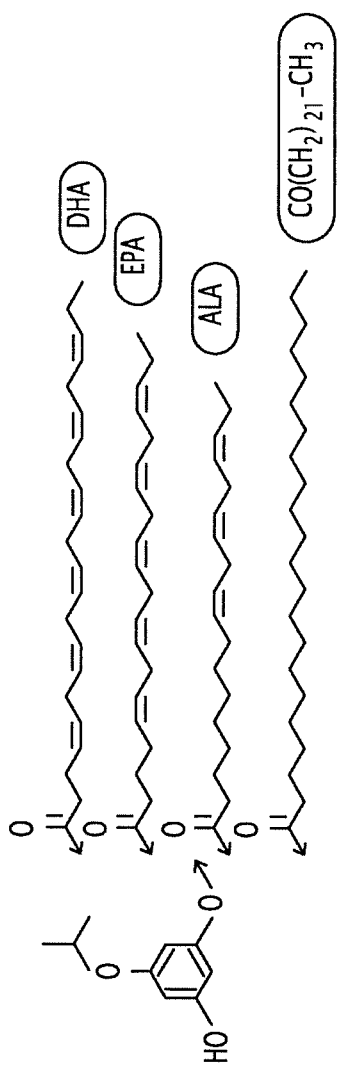
Figure 11:
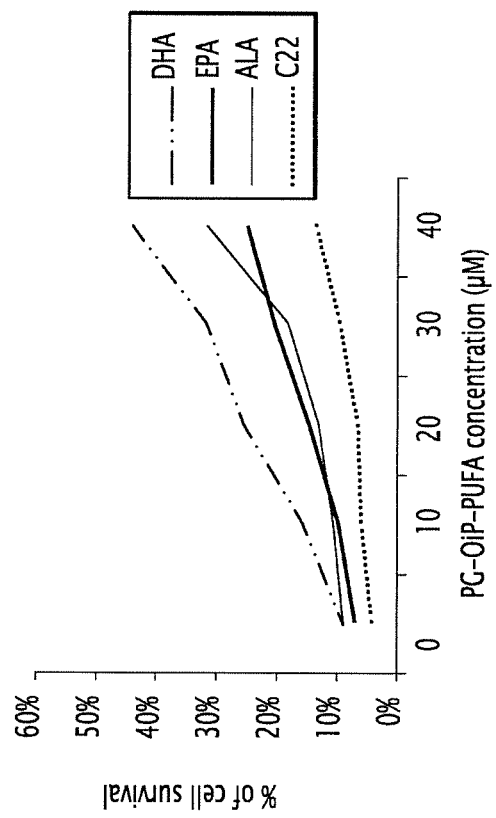

FIG. 10 represents some compounds according to the invention as explained in example 12, and FIG. 11 concerns the comparison of the anti- carbonyl efficacies in RPE cell lines of the compounds of FIG. 10.

Figure 12:
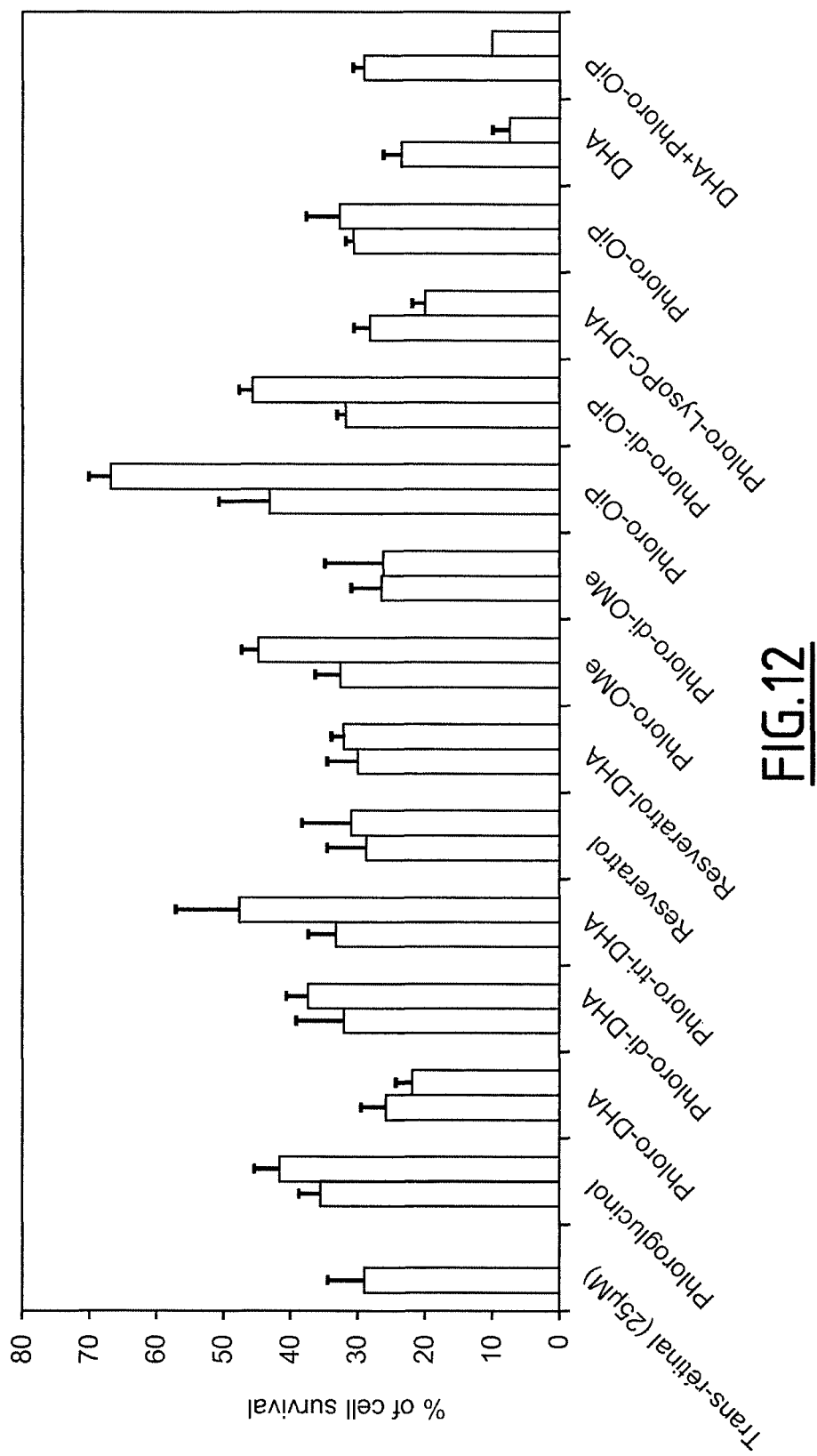

FIG. 12 concerns the dose-dependent protection of several compounds of the invention of ARPE-19 cell cultures exposed to atRal, in condition to prove their intracellular action (pre-treatment). It represents ARPE-19 cell survival in the presence of AtR (25 µM). For each compound, the left column corresponds to the dose of 10 µM and the right column corresponds to the dose of 40 µM.

Figure 13:
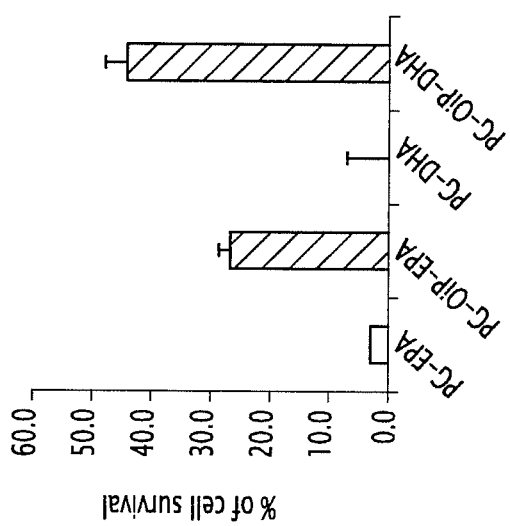

FIG. 13 concerns the comparison of the anti-carbonyl efficacies of PG derivatives with (hatched columns) and without an alkyl group (white columns) in ARPE-19 cell lines.

Figure 14:
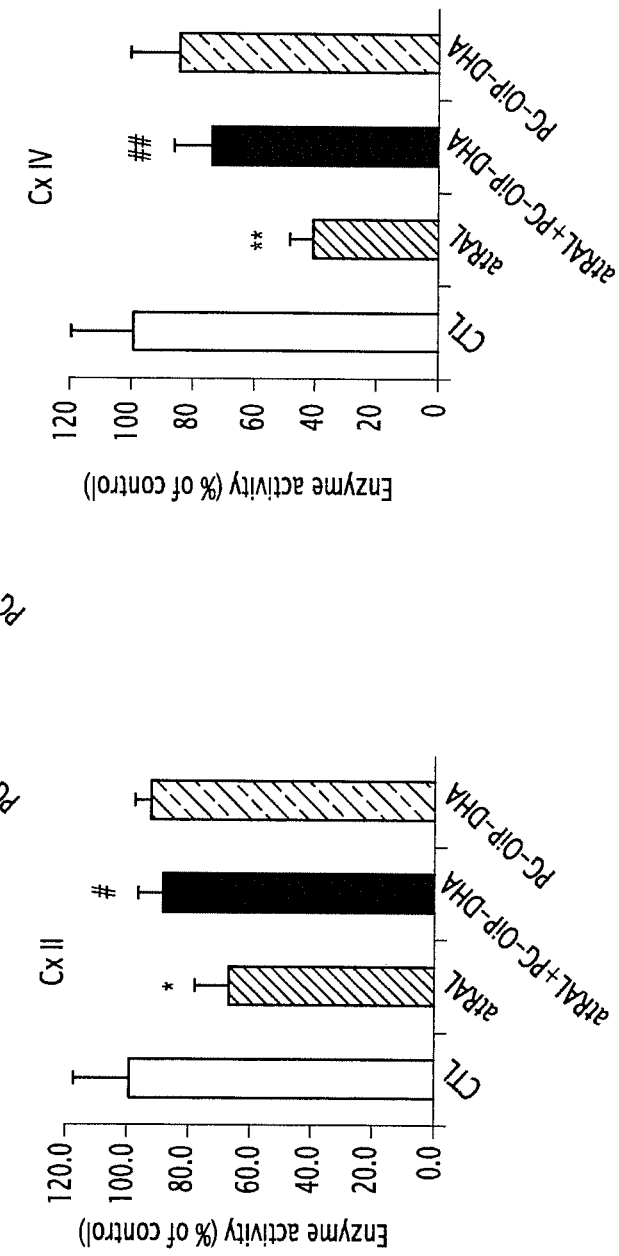
Figure 15:
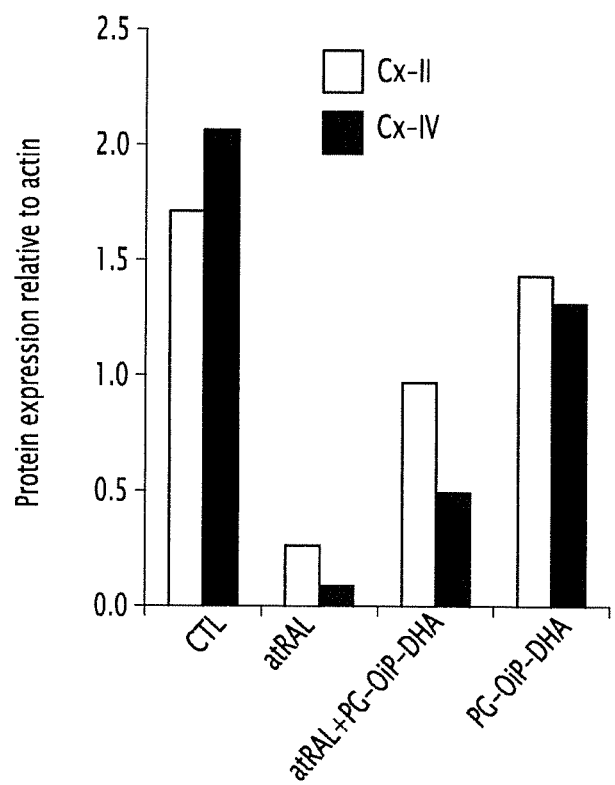

FIG. 14 concerns the efficacy of PG-OiP-DHA in the protection of the mitochondrial activity, and FIG. 15 concerns the analysis of MRC protein expression.

EXAMPLES

Example 1: Synthesis of DHA-Phloroglucinol Conjugates

DHA used in the following synthesis was extracted from cod liver oil using a process developed to concentrate PUFAs starting from fish or algal oil. The process was carried out in one single step, in which fish liver oil was saponified in the presence of NaOH, free fatty acids were extracted using liquid-liquid extraction and separated from the unsaponifiable material. Then, mono-unsaturated fatty acids were eliminated using urea complexation, based on the difference in the spatial configuration of fatty acids according to their degree of unsaturation. This crystallization process allowed to isolate a crude mixture of DHA and EPA (eicosapentaenoic acid C20:5 n-3), which after purification on reverse phase yielded 5% of DHA (starting from cod liver oil) with 85% of purity (impurities consisting of mono unsaturated fatty acids such as palmitoleic acid (C16:1 n-7) and oleic acid (C18:1 n-9)).

To obtain phloroglucinol-DHA conjugates with acceptable yield, a silyl protecting group such as triisopropylsilyl (TIPS) was selected because of its efficient deprotection in mild conditions in the presence of ester linkage.

The following scheme illustrates the implemented step for preparing the DHA-phloroglucinol conjugates of the invention.

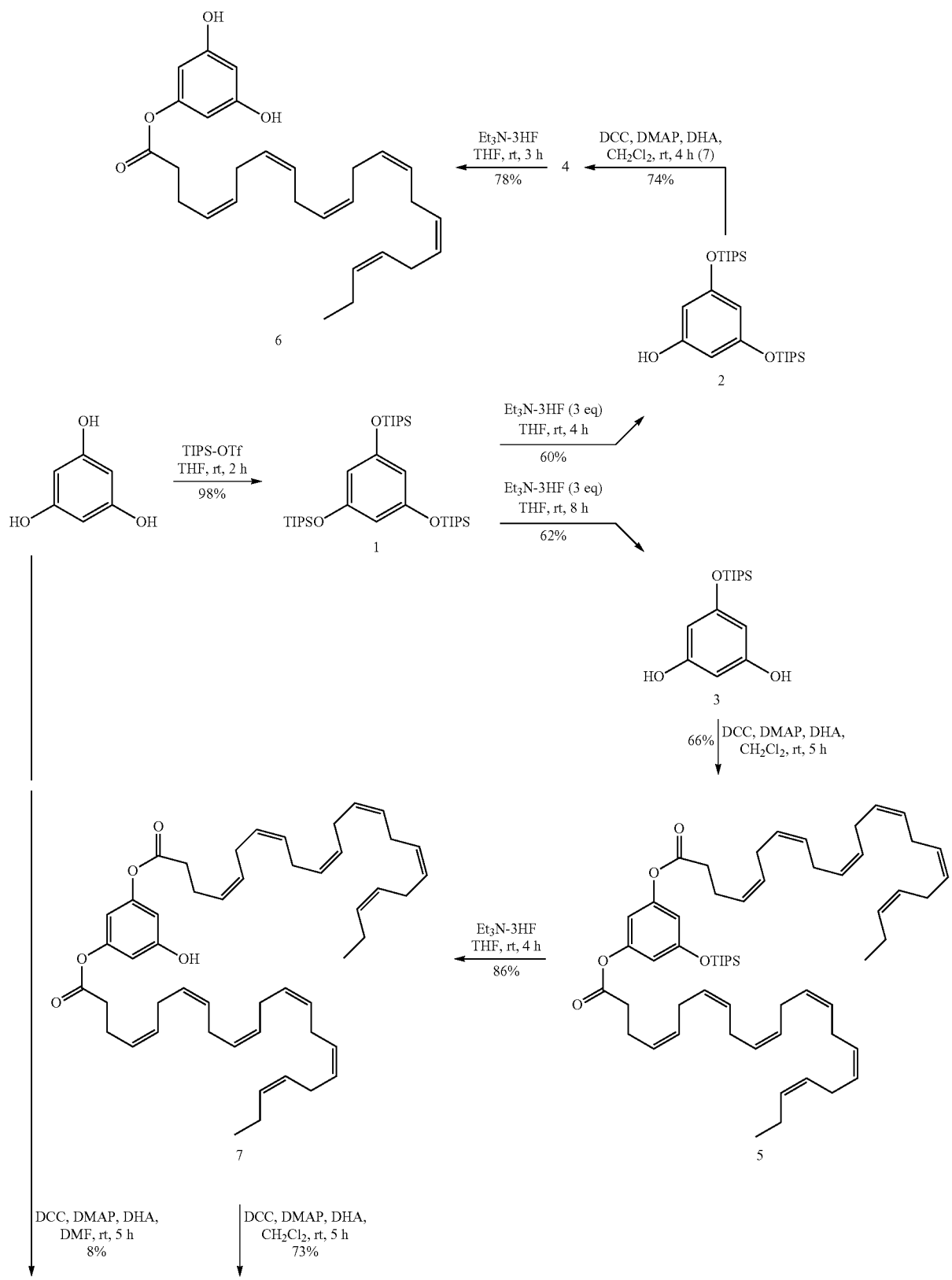

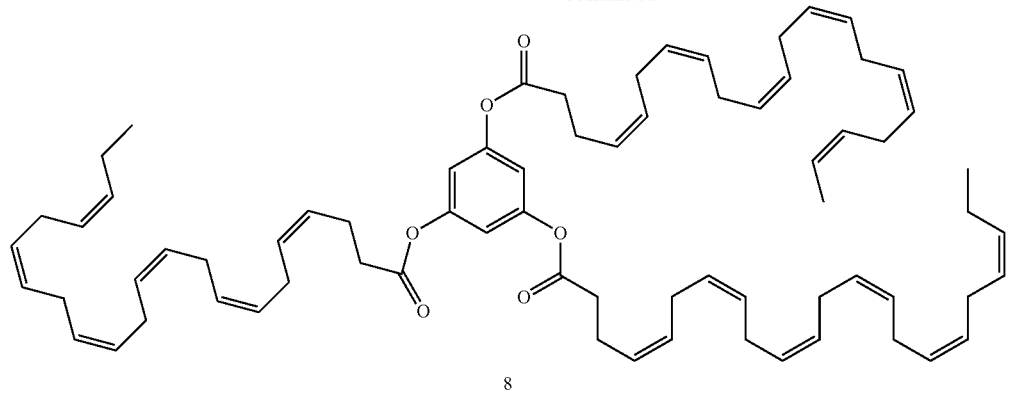 [SMILES: C/C=C\C/C=C\C/C=C\C/C=C\C/C=C\C/C=C\CCC(=O)Oc1cc(OC(=O)CC/C=C\C/C=C\C/C=C\C/C=C\C/C=C\C/C=C\CC)cc(OC(=O)CC/C=C\C/C=C\C/C=C\C/C=C\C/C=C\C/C=C\CC)c1]

8

The di-protected phloroglucinol 2 was prepared in an original way, starting from the total protection of phloroglucinol 1 using 3 equivalents of TIPS-OTf in THF following by a slow mono-desilylation using triethylamine trihydrofluoride (3 equiv. Et$_3$N-3HF) during 4 h. The process allowed to prepare the intermediate 2 in 59% overall yield on the two steps (only 30% could be obtained by a direct di-silylation process). Using the same amount of Et$_3$N-3HF and increasing the reaction time (from 4 h to 8 h) the mono-protected derivative 8 was obtained in 62%, while a controlled mono silylation (1eq. TIPS-OTf, at 0° C.) gave no more than 38%. Then, the coupling reactions were performed using classical DCC/DMAP reagents and afforded DHA conjugates 4 and 5 in 74% and 66% yield respectively. The deprotection of TIPS groups were performed using Et$_3$N-3HF in THF at room temperature and afforded the desired lipophenol 6 and 7 with 78% and 86% yield, without cleavage of the ester linkage or degradation of the polyunsaturated moiety.

Tri-DHA conjugate 8 was obtained in much better yield, starting from di-DHA-phloroglucinol 7 (73%), than from direct coupling of phloroglucinol with 3 equivalents of DHA (only 8%). The weak coupling conversion could be explained because of steric constraint or a less reactivity of phloroglucinol compared to its silylated derivatives.

The implemented steps as mentioned above are described hereafter in detail.

Extraction process of DHA from cod liver oil: Commercially available cod liver oil (5 g, commercially available, Cooper, France) were dissolved in a mixture of ethanol and water (35 mL, 95/5) in presence of NaOH (1.50 g) under argon atmosphere. The mixture was protected from the light with a foil paper and heated at 82° C. during 2 h. The ethanolic fraction was evaporated and the residue was dissolved in hexane (30 mL) after heating. Then, water (25 mL) was added to the organic layer and unsaponifiable material was removed with repeated hexane extraction of the aqueous phase (4×30 mL of hexane). The aqueous phase containing the soaps was acidified to pH 2 using HCl solution (50%). The fatty acids were extracted with hexane (4×25 mL). The organic phase was concentrated under reduced pressure to give 4.62 g of a crude fatty acids oil. Urea (13.86 g) and ethanol 95% (55 mL) were added to the crude residue. The mixture was heated at 60° C.-70° C., protected from the light, until the mixture turned into a clear homogenous solution. Then, the mixture was kept at room temperature and then placed at 4° C. during 24h. The crystals formed were separated from the liquid by filtration. The filtrate obtained was diluted with water (35 mL) and acidified to pH 4-5 with HCl solution (6N). Hexane (70 mL) was added and the solution was stirred thoroughly for 1 h. The hexane layer containing the liberated fatty acids was separated from the aqueous layer and washed with water three times (3×40 mL). The organic phase was dried with Na$_2$SO$_4$ and concentrated under reduced pressure to give 820 mg of a crude mixture of PUFAs, which was purified by preparative HPLC (column Atlantis Prep OBD™ 10 μm (19×250 mm), H$_2$O/MeOH 13/87 isocratic, detection 217 nm) to give pure DHA (266 mg, 5% w/w)). $^1$H NMR (500 MHz; CDCl$_3$) $\delta_H$ 5.43-5.30 (m, 12H, CH=CH), 2.85-2.80 (m, 10H, CH$_2$ bis-allylic), 2.42-2.40 (m, 4H, CH$_2$—C=O, CH$_2$ allylic), 2.07 (quint, J=7.5 Hz, 2H, CH$_2$ allylic), 0.98 (t, J=7.5 Hz, 3H, CH$_3$); MS (ESI) m/z 327 [M−H]$^-$.

2-methyl-2-((1E,3E,5E)-4-methyl-6-(2,6,6-trimethylcyclohex-1-enyl) hexa-1,3,5-trienyl)-2H-chromene-5,7-diol; Chromene A: To a stirred solution of trans-retinal (200 mg, 0.35 mmol) in ethanol (8 mL), were added phloroglucinol (48.28 mg, 0.35 mmol) and acetic acid (40 μL, 0.35 mmol). The reaction was stirred at room temperature for 48 h, protected from the light with foil paper. After concentration of is solvent under reduced pressure, the residue obtained was dissolved in AcOEt, (20 mL) and washed with water (10 mL). The organic layer was recovered, dried with MgSO$_4$ and concentrated under reduced pressure. The residue obtained was purified by chromatography on silica gel (90/10 to 85/15 pentane/AcOEt) to give Chromene A (112.4 mg, 41%) as a solid contaminated by 13% of a by product. Chromene A was isolated after purification by preparative HPLC to furnish full characterization (gradient of hexane/AcOEt, t$_{0'=100/0}$, t$_{15'=90/10}$, t$_{45'=80/20}$, t$_{75'=70/30}$; 15 mL/min, column luna 5μ Silica 100A 250×21.20 mm, detection 254 nm).

R$_f$(CH$_2$Cl$_2$/MeOH) 0.4; $^1$H NMR (500 MHz; CD$_3$OD) $\delta_H$ 6.63 (dd, J=11.5 Hz, J=15.5 Hz, 1H, H$_{11}$), 6.63 (d, J=10.0 Hz, 1H, H$_{15}$), 6.14 (d, J=16.5 Hz, 1H, H$_7$), 6.03 (d, J=16.5 Hz, 1H, H$_8$), 5.98 (d, J=11.0 Hz, 1H, H$_{10}$), 5.85 and 5.81 (d, J=2.0 Hz, 1H, and d, J=2.5 Hz, 1H, H$_{18}$ and H$_{20}$), 5.75 (d, J=15.0 Hz, 1H, H$_{12}$), 5.39 (d, J=10.0 Hz, 1H, H$_{14}$), 2.02-2.00 (m, 2H, H$_4$ (CH$_2$)), 1.86 (s, 3H, H$_{25}$ (CH$_3$)), 1.68 (s, 3H, H$_{24}$ (CH$_3$)), 1.67-1.60 (m, 2H, H$_3$ (CH$_2$)), 1.49 (s, 3H, H$_{26}$ (CH$_3$)), 1.48-1.46 (m, 2H, H$_2$ (CH$_2$)), 1.00 (s, 6H, H$_{22}$, H$_{23}$ (CH$_3$)); $^{13}$C NMR (125 MHz; CDCl$_3$ $\delta_c$ 159.7 (C$_{19}$), 156.4 (C$_{21/17}$), 139.1 (C$_8$, 139.0 (C$_6$), 137.1 (C$_{12}$), 137.0 (C$_9$), 130.4 (C$_{10}$), 129.9 (C$_5$), 127.6 (C$_7$), 126.3 (C$_{15}$), 123.1 (C$_{14}$), 119.1 (C$_{11}$), 103.9 (C$_{16}$), 96.3 (C$_{20/18}$), 78.5 (C$_{13}$), 40.7 (C$_2$), 35.1 (C$_1$), 33.9 (C$_4$), 29.3 (C$_{22/23}$), 27.6 (C$_{26}$), 21.8 ($C_{24}$), 20.3 ($C_3$), 12.6 ($C_{25}$); HRMS (ESI-TOF) m/z: [M–H]⁻ calcd. for $C_{26}H_{31}O_3$ 391.2278; found 391.2272; HPLC rt: 11.26 min, (Atlantis C18 5 μm (4.6×250 mm), $H_2O$ 0.1% TFA/ACN, $t_{0'=25/75}$, $t_{25'=20/80}$, $t_{28'=0/100}$, $t_{33'=0/100}$, detection 298 nm).

General Procedure for coupling step between DHA and polyphenolic derivatives: DHA (1.1 equiv., 0.30 mmol) and each of the concerned phenolic derivatives (1 equiv., 0.27 mmol) were dissolved in dry $CH_2Cl_2$ (6 mL). DCC (1.1 equiv., 0.30 mmol) and DMAP (0.1 equiv, 0.03 mmol) were added to the solution and the reaction was stirred at room temperature for 5 h under nitrogen. The mixture was left 2 h at 4° C. to induce dicyclohexylurea crystallization. The urea residue was then filtered off, and the filtrate was washed with water and brine. The organic layer was dried on $MgSO_4$ and concentrated under reduced pressure. Purification of the crude material was performed by chromatography on silica gel to afford the desired lipophenol.

General Procedure for deprotection of TIPS protecting group on DHA-polyphenols derivatives: To a solution of the appropriate protected DHA-polyphenol (1 equiv., 0.19 mmol) in anhydrous THF (13 mL), was added dropwise triethylammonium trihydrofluoride ($Et_3N$-3HF, 3 equiv., 0.57 mmol for mono-protected compounds or 6 equiv., 1.14 mmol for di-protected derivatives). The reaction was stirred at room temperature during 4 h to 6 h, until completion of the reaction. AcOEt (40 mL) was added to the mixture and the organic layer was washed with water (15 mL) and brine (15 mL). The organic phase was dried ($MgSO_4$) and concentrated under vacuum. The residue obtained was purified by chromatography on silica gel to give the deprotected lipophenol.

1,3,5-tris(triisopropylsilyloxy)benzene 1: To a stirred solution of phloroglucinol (1 g, 7.90 mmol) in dry THF (60 mL), triethylamine (3.68 ml, 23 mmol) and triisopropylsilyl trifluoromethanesulfonate (TIPS-OTf) (7 mL, 23 mmol) were added dropwise. The reaction mixture was stirred at room temperature during 2 h. AcOEt (60 mL) was added to the mixture and the organic layer was washed with water (40 mL) and brine (40 mL). The organic phase was dried ($MgSO_4$) and concentrated under vacuum. The residue obtained was purified by chromatography on silica gel (99/1 Hexane/AcOEt) to give the tri-protected phloroglucinol 1 (4.64 g, 98%) as a yellow oil.

$R_f$(pentane) 0.28; ¹H NMR (500 MHz; CDCl₃) $\delta_H$ 6.07 (s, 3H, $CH_{aro}$), 1.27-1.18 (m, 9H, CH—Si), 1.09 (d, J=7.3 Hz, 54H, $(CH_3)_2C$); ¹³C NMR (125 MHz; CDCl₃) $\delta_c$ 157.4, 105.8, 18.1, 12.8; HRMS (ESI-TOF) m/z: [M+H]⁺ calcd. for $C_{33}H_{67}O_3Si_3$ 595.4392; found 595.4395.

3,5-bis(triisopropylsilyloxy)phenol 2: The tri-protected phloroglucinol 1 (5.01 g, 8.43 mmol) was dissolved in dry THF (200 mL). $Et_3N$-3HF (2.90 mL, 17.70 mmol) was added dropwise and the mixture was stirred at room temperature during 4 h. The reaction was followed by TLC and stopped in order to avoid as much as possible the formation of di-deprotected derivative. AcOEt (200 mL) was added to the mixture and the organic layer was washed with water (200 mL) and brine (100 mL). The organic phase was dried ($MgSO_4$) and concentrated under vacuum. The residue obtained was purified by chromatography on silica gel (95/5 pentane/AcOEt) to give the di-protected phloroglucinol 2 (2.25 g, 60%) as a yellow oil. The mono-protected derivative 3 was isolated in 18% as a white solide (0.45 g).

$R_f$ (pentane/AcOEt 80/20) 0.8; ¹H NMR (500 MHz; CDCl₃) $\delta_H$ 6.03 (t, J=2.0 Hz, 1H, $CH_{aro}$), 6.01 (d, J=2.0 Hz, 2H, $CH_{aro}$), 1.27-1.19 (m, 6H, CH—Si), 1.09 (d, J=7.3 Hz, 36H, $(CH_3)_2C$); ¹³C NMR (125 MHz; CDCl₃) $\delta_c$ 157.8, 157.0, 105.1, 101.1, 18.1, 12.8; HRMS (ESI-TOF) m/z: [M–H]⁻ calcd. for $C_{24}H_{45}O_3Si_2$ 437.2907; found 437.2911.

(4,7,10,13,16,19 Z)-3,5-bis(triisopropylsilyloxy)phenyl-docosa-4, 7,10,13,16,19-hexaenoate 4: Coupling of the di-TIPS-phloroglucinol 2 (130 mg, 0.29 mmol) and DHA (104 mg, 0.32 mmol) was performed according to the general procedure and afforded 4 (164 mg, 74%) as an uncolored oil after purification on silica gel chromatography (hexane/AcOEt 99.7/0.3 to 99/1).

$R_f$ (hexane/AcOEt 99/1) 0.23; ¹H NMR (500 MHz; CDCl₃) $\delta_H$ 6.29-6.27 (m, 1H, $CH_{aro}$), 6.25-6.24 (m, 2H, $CH_{aro}$), 5.45-5.30 (m, 12H, CH=CH), 2.87-2.81 (m, 10H, $CH_2$ bis-allylic), 2.57 (t, J=7.3 Hz, 2H, $CH_2$—C=O), 2.52-2.48 (m, 2H, $CH_2$ allylic), 2.07 (quint, J=7.5 Hz, 2H, $CH_2$ allylic), 1.26-1.18 (m, 6H, CH—Si), 1.08 (d, J=7.5 Hz, 36H, $(CH_3)_2C$), 0.97 (t, J=7.5 Hz, 3H, $CH_3$); ¹³C NMR (125 MHz; CDCl₃) $\delta_c$ 171.1, 157.1, 151.8, 132.0, 129.6, 128.6, 128.3, 128.3, 128.2, 128.1, 128.1, 128.0, 127.9, 127.0, 109.2, 106.9, 34.4, 25.6, 25.5, 22.7, 20.6, 17.8, 14.2, 12.7; HRMS (ESI-TOF) m/z: [M+H]⁺ calcd. for $C_{46}H_{77}O_4Si_2$ 749.5354; found 749.5363.

(4,7,10,13,16,19 Z)-3,5-dihydroxyphenyl-docosa-4,7,10, 13,16,19-hexaenoate 6: Deprotection of the protected DHA-phloroglucinol 4 (50 mg, 0.07 mmol) was performed using the general procedure and afforded 6 (23 mg, 78%) as an uncolored oil after purification on silica gel chromatography (hexane/AcOEt 9/1 to 75/25).

$R_f$ (hexane/AcOEt 70/30) 0.36; ¹H NMR (500 MHz; CDCl₃) $\delta_H$ 6.06 (s, 3H, $CH_{aro}$), 5.48-5.28 (m, 12H, CH=CH), 2.87-2.79 (m, 10H, $CH_2$ bis-allylic), 2.63 (t, J=7.0 Hz, 2H, $CH_2$—C=O), 2.53-2.48 (m, 2H, $CH_2$ allylic), 2.06 (quint, J=7.5 Hz, 2H, $CH_2$ allylic), 0.96 (t, J=7.5 Hz, 3H, $CH_3$); ¹³C NMR (125 MHz; CDCl₃) $\delta_c$ 172.7, 157.3, 151.8, 132.0, 129.9, 128.6, 128.4, 128.3, 128.3, 128.1, 128.0, 127.8, 127.8, 127.2, 127.0, 101.9, 101.1, 34.3, 25.6, 25.6, 25.6, 25.5, 22.7, 20.5, 14.2; HRMS (ESI-TOF) m/z: [M–H]⁻ calcd. for $C_{28}H_{35}O_4$ 435.2535; found 435.2538.

5-(triisopropylsilyloxy)benzene-1,3-diol 3: The tri-protected phloroglucinol 1 (200 mg, 0.33 mmol) was dissolved in dry THF (12 mL). $Et_3N$-3HF (164 μl mL, 1 mmol) was added dropwise and the reaction was followed by TLC and stopped in order to reduce as much as possible the formation of the mono-deprotected derivative. After 6 h of stirring at room temperature, 1 additional equivalent of $Et_3N$-3HF is added to the mixture. The reaction was stopped after 8 h. AcOEt (15 mL) was added to the mixture and the organic layer was washed with water (10 mL) and brine (10 mL). The organic phase was dried ($MgSO_4$) and concentrated under vacuum. The residue obtained was purified by chromatography on silica gel (pentane/AcOEt 95/5) to give the mono-protected phloroglucinol 3 (59 mg, 62%) as a white solide. The di-protected derivative 2 was isolated in 13% as a yellow oil (20 mg).

$R_f$ (hexane/AcOEt 70/30) 0.34; ¹H NMR (500 MHz; CDCl₃) $\delta_H$ 5.99 (d, J=2.0 Hz, 2H, $CH_{aro}$), 6.01 (t, J=2.0 Hz, 1H, $CH_{aro}$), 1.27-1.18 (m, 3H, CH—Si), 1.08 (d, J=7.5 Hz, 18H, $(CH_3)_2C$); ¹³C NMR (125 MHz; CDCl₃) $\delta_c$ 158.2, 157.3, 100.5, 96.5, 18.0, 12.8; HRMS (ESI-TOF) m/z: [M–H]⁻ calcd. for $C_{15}H_{25}O_3Si$ 281.1573; found 281.1570.

(4,4',7,7',10,10',13,13',16,16',19,19'Z)-5-(triisopropylsilyloxy)-1, 3-phenylene-didocosa-4,7,10,13,16,19-hexaenoate 5: Coupling of the mono-TIPS-phloroglucinol 3 (86 mg, 0.30 mmol) and DHA (200 mg, 0.60 mmol) was performed with the general procedure and afforded 5 (183 mg, 66%) as an uncolored oil after purification on silica gel chromatography (pentane/AcOEt 98/2).

$R_f$ (pentane/AcOEt 98/2) 0.34; $^1$H NMR (500 MHz; CDCl$_3$) $\delta_H$ 6.51 (s, 3H, CH$_{aro}$), 5.47-5.28 (m, 24H, CH=CH), 2.87-2.80 (m, 20H, CH$_2$ bis-allylic), 2.60-2.57 (m, 4H, CH$_2$—C=O), 2.51-2.47 (m, 4H, CH$_2$ allylic), 2.07 (quint, J=7.5 Hz, 4H, CH$_2$ allylic), 1.27-1.22 (m, 3H, CH—Si), 1.08 (d, J=7.5 Hz, 18H, (CH$_3$)$_2$C), 0.97 (t, J=7.5 Hz, 6H, CH$_3$); $^{13}$C NMR (125 MHz; CDCl$_3$) $\delta_c$ 170.9, 157.0, 151.4, 132.0, 129.7, 128.5, 128.3, 128.2, 128.2, 128.1, 128.0, 127.9, 127.8, 127.4, 127.0, 110.9, 108.0, 34.2, 25.6, 25.6, 25.5, 22.6, 20.5, 17.8, 14.2, 12.5; HRMS (ESI-TOF) m/z: [M+H]$^+$ calcd. for C$_{59}$H$_{87}$O$_5$Si 903.6317; found 903.6321.

(4,4',7,7',10,10',13,13',16,16',19,19'Z)-5-hydroxy-1,3-phenylene didocosa-4,7,10,13,16,19-hexaenoate 7: Deprotection of the protected DHA-phloroglucinol 5 (168 mg, 0.19 mmol) was performed with the general procedure and afforded 7 (119 mg, 86%) as an uncolored oil after purification on silica gel chromatography (hexane/AcOEt 90/10).

$R_f$ (hexane/AcOEt 90/10) 0.19; $^1$H NMR (500 MHz; CDCl$_3$) $\delta_H$ 6.48 (s, 3H, CH$_{aro}$), 5.48-5.29 (m, 24H, CH=CH), 2.88-2.80 (m, 20H, CH$_2$ bis-allylic), 2.60 (t, J=7.1 Hz, 4H, CH$_2$—C=O), 2.52-2.48 (m, 4H, CH$_2$ allylic), 2.08 (quint, J=7.5 Hz, 4H, CH$_2$ allylic), 0.98 (t, J=7.5 Hz, 6H, CH$_3$); $^{13}$C NMR (125 MHz; CDCl$_3$) $\delta_c$ 171.1, 156.7, 151.6, 132.0, 129.8, 128.5, 128.3, 128.3, 128.2, 128.0, 128.0, 127.9, 127.8, 127.3, 127.0, 107.6, 106.7, 34.2, 25.6, 25.6, 25.6, 25.5, 22.6, 20.5, 14.2; HRMS (ESI-TOF) m/z: [M+H]$^+$ calcd. for C$_{50}$H$_{67}$O$_5$ 747.4989; found 747.4994.

(4,4',4'',7,7',7'',10,10',10'',13,13',13'',16,16',16'',19,19',19''Z)-benzene-1,3,5-triyl tridocosa-4,7,10,13,16,19-hexaenoate 8: Coupling of the di-DHA-phloroglucinol 7 (108 mg, 0.14 mmol) and DHA (46 mg, 0.15 mmol) was performed with the general procedure and afforded 8 (108 mg, 73%) as an uncolored oil after purification on silica gel chromatography (hexane/AcOEt 95/2).

$R_f$ (hexane/AcOEt 95/5) 0.29; $^1$H NMR (500 MHz; CDCl$_3$) $\delta_H$ 6.82 (s, 3H, CH$_{aro}$), 5.48-5.28 (m, 36H, CH=CH), 2.87-2.79 (m, 30H, CH$_2$ bis-allylic), 2.59 (t, J=7.5 Hz, 6H, CH$_2$—C=O), 2.46-2.50 (m, 6H, CH$_2$ allylic), 2.07 (quint, J=7.5 Hz, 6H, CH$_2$ allylic), 0.97 (t, J=7.5 Hz, 9H, CH$_3$); $^{13}$C NMR (125 MHz; CDCl$_3$) $\delta_c$ 170.9, 151.4, 132.3, 130.1, 128.8, 128.6, 128.5, 128.5, 128.3, 128.3, 128.2, 128.1, 127.6, 127.3, 112.9, 34.5, 25.9, 25.9, 25.8, 22.8, 20.8, 14.5; HRMS (ESI-TOF-ASAP+) m/z: [M+H]$^+$ calcd. for C$_{72}$H$_{97}$O$_6$ 1057.7280; found 1057.7285.

Example 2: Synthesis of Alkylated DHA-Phloroglucinol Conjugates

Alkylation such as methylation is one of the most abundant metabolization of dietary (poly)phenols after ingestion. It appears thus interesting to evaluate the impact of O-alkylation of the phenol function on the efficiency of the carbonyl trap action. Regarding the mechanism of the chromene formation starting from phloroglucinol and trans-retinal, O- and C-alkylation may be influenced by the introduction of such an alkyl substituent. The nucleophilicity developed by the carbon atoms of such aromatic rings may be adjusted by the presence of inductive electron effect and make phloroglucinol derivatives more reactive with the trans-retinal carbonyl soft-type electrophiles.

In order to access alkylated phloroglucinol-DHA, the synthesis of mono-alkylated and mono-protected phloroglucinol 11 was investigated to allow the introduction of the lipid moiety at the latest step of the synthetic pathway.

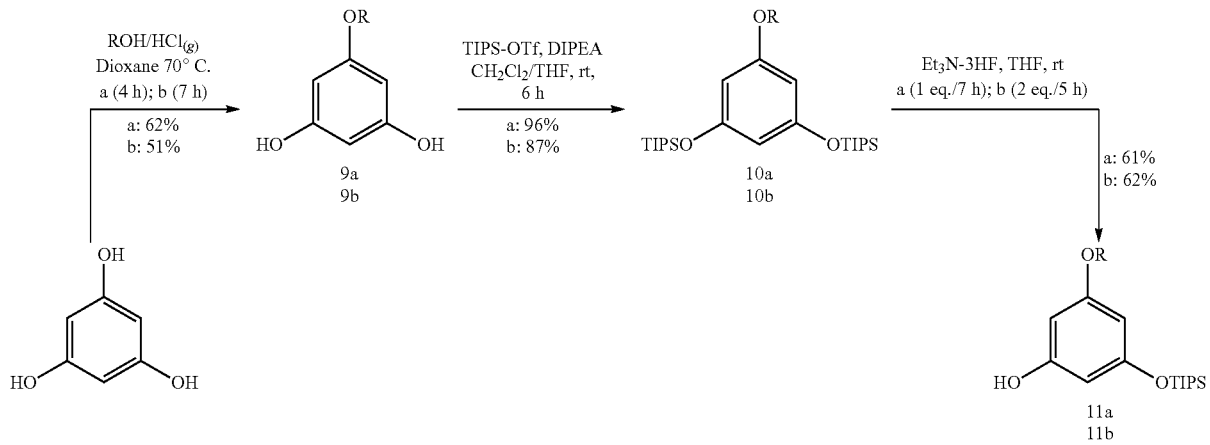

a: R = Me
b: R = iPr

The difficulty in the strategy was to perform a selective mono-alkylation and/or mono-silylation of the symmetrical phloroglucinol in the presence of phenol functions with identical reactivity. Using a solution of MeOH, or iPrOH saturated with HCl gas the mono-alkylation could be performed starting from the phloroglucinol, in an acceptable yield lowering the proportion of dialkylated derivatives observed using commonly-used O-alkylation reageant such as DMS or 2-bromopropane reagent. The total protection of phloroglucinol with the TIPS protecting group (10), followed by the mono deprotection process, afforded the desired mono-methytaled/isopropylated and protected phloroglucinol 11 in 58% and 54% in two steps.

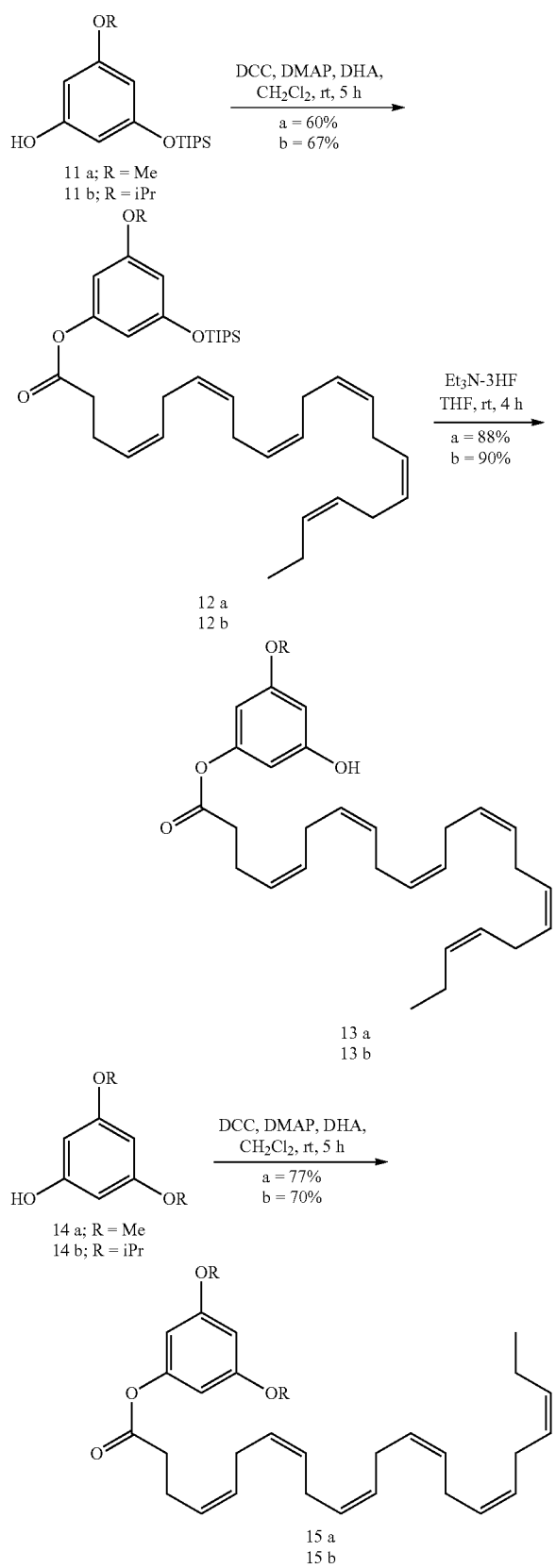

Using the same coupling conditions (DCC/DMAP) as for lipophenol 6, mono-alkyl and di-alkyl phloroglucinols 11 and 14 were coupled to DHA and afforded alkylated-phloroglucinol DHA conjugates 13 and 15 in excellent to moderate yield, after removal of TIPS groups in the presence of Et$_3$N-3HF for protected derivatives.

The implemented steps as mentioned above are described hereafter in detail.

5-methoxybenzene-1,3-diol 9a: To a suspension of phloroglucinol (0.40 g, 3.17 mmol) in dioxane (1 mL) was added a freshly prepared solution of MeOH saturated with dry HCl (gaz) (4 mL, 17N). The reaction was stirred at room temperature during 3 h. An additional amount of the saturated HCl solution was added (1 mL) and the reaction was kept at 70° C. for 1 h. The solvents were evaporated under vacuum and the residue obtained was purified by chromatography on silica gel (CH$_2$Cl$_2$/MeOH 98/2) to give 9a (0.28 mg, 62%) as a white solid. The di-methylated residue 14a was isolated in 25% yield.

R$_f$ (CH$_2$Cl$_2$/MeOH 95/5) 0.47; $^1$H NMR (500 MHz; MeOD) δ$_H$ 5.88 (s, 3H, CH$_{aro}$) 3.69 (s, 3H, CH$_3$O); $^{13}$C NMR (125 MHz; CDCl$_3$) δ$_c$ 161.7, 158.1, 95.7, 94.0, 55.2; HRMS (ESI-TOF) m/z: [M−H]$^-$ calcd. for C$_7$H$_7$O$_3$ 139.0395; found 139.0397.

5-isopropoxybenzene-1,3-diol 9b: To a suspension of phloroglucinol (0.40 g, 3.17 mmol) in dioxane (1 mL) was added a freshly prepared solution of iPOH saturated with dry HCl (gaz) (4 mL, 32N). The reaction was stirred at room temperature during 1 h. An additional amount of the saturated HCl solution was added (1 mL) and the reaction was kept at 70° C. for 7 h. The solvents were evaporated under vacuum and the residue obtained was purified by chromatography on silica gel (CH$_2$Cl$_2$/MeOH 98/2) to give 9b (0.27 mg, 51%) as a white solid. The di-alkylated derivative 14b was isolated in 13% yield.

R$_f$ (CH$_2$Cl$_2$/MeOH 95/5) 0.4; $^1$H NMR (500 MHz; CDCl$_3$) δ$_H$ 5.99 (d, J=1.9 Hz, 2H, CH$_{aro}$), 5.96 (t, J=1.9 Hz, 1H, CH$_{aro}$), 5.70 (br, 2H, OH), 4.45 (quint, J=7.5 Hz, 1H, CH), 1.31 (d, J=6.0 Hz, 6H, CH3); $^{13}$C NMR (125 MHz; CDCl$_3$) δ$_c$ 160.0, 158.1, 95.8, 95.5, 70.0, 22.0; HRMS (ESI-TOF) m/z: [M−H]$^-$ calcd. for C$_9$H$_{11}$O$_3$ 167.0708; found 167.0710.

5-methoxy-1,3-bis(triisopropylsilyloxy)benzene 10a: Phloroglucinol-OMe 9a (100 mg, 0.71 mmol) was dissolved in dry CH$_2$Cl$_2$ (6 mL) and dry THF (600 µl). Diisopropylethylamine (257 µl, 1.50 mmol) and TIPS-OTf (403 µL, 1.50 mmol) were added dropwise to the solution and the reaction mixture was stirred at room temperature during 6 h. Additional amount of DIPEA and TIPS-OTf were added to reach completion of the reaction. After 6 h of reaction, AcOEt (15 mL) was added to the mixture and the organic layer was washed with water (10 mL) and brine (10 mL). The organic phase was dried (MgSO$_4$) and concentrated under vacuum. The residue obtained was purified by chromatography on silica gel (hexane/AcOEt 99/1) to give the di-protected phloroglucinol-OMe 10a (311 mg, 96%) as an uncolored oil.

R$_f$ (hexane/AcOEt 95/5) 0.80; $^1$H NMR (500 MHz; CDCl$_3$) δ$_H$ 6.09-6.08 (m, 2H, CH$_{aro}$), 6.07-6.06 (m, 1H, CH$_{aro}$), 3.73 (s, 3H, CH$_3$O), 1.27-1.21 (m, 6H, CH—Si), 1.10 (d, J=7.0 Hz, 36H, (CH$_3$)$_2$C); $^{13}$C NMR (125 MHz; CDCl$_3$) δ$_c$ 161.3, 157.8, 105.0, 99.7, 55.5, 18.2, 13.0; HRMS (ESI-TOF) m/z: [M+H]$^+$ calcd. for C$_{25}$H$_{49}$O$_3$Si$_2$ 453.3214; found 453.3226.

5-isopropoxy-1,3-bis(triisopropylsilyloxy)benzene 10b: Phloroglucinol-OiP 9b (231 mg, 1.37 mmol) was dissolved in dry CH$_2$Cl$_2$ (24 mL). Diisopropylethylamine (617 µl, 3.60 mmol) and TIPS-OTf (969 µL, 3.60 mmol) were added dropwise to the solution and the reaction mixture was stirred at room temperature during 6 h. AcOEt (30 mL) were added to the mixture and the organic layer was washed with water (15 mL) and brine (15 mL). The organic phase was dried (MgSO$_4$) and concentrated under vacuum. The residue obtained was purified by chromatography on silica gel (hexane/AcOEt 99.5/0.5) to give the di-protected phloroglucinol-OiP 10b (573 mg, 87%) as an uncolored oil.

R$_f$ (hexane/AcOEt 95/5) 0.88; $^1$H NMR (500 MHz; CDCl$_3$) $\delta_H$ 6.07-6.06 (m, 2H, CH$_{aro}$), 6.04-6.02 (m, 1H, CH$_{aro}$), 4.42 (quint, J=6.0 Hz, 1H, CH$_{ip}$), 1.29 (d, J=6.0 Hz, (CH$_3$)$_2$C$_{ip}$), 1.26-1.19 (m, 6H, CH—Si), 1.09 (d, J=6.0 Hz, 36H, (CH$_3$)$_2$C$_{TIPS}$); $^{13}$C NMR (125 MHz; CDCl$_3$) $\delta_c$ 159.5, 157.7, 105.0, 101.9, 70.2, 22.3, 18.2, 12.9; HRMS (ESI-TOF) m/z: [M+H]$^+$ calcd. for C$_{27}$H$_{53}$O$_3$Si$_2$ 481.3527; found 481.3537.

3-methoxy-5-(triisopropylsilyloxy)phenol 11a: The di-protected phloroglucinol 10a (92 mg, 0.19 mmol) was dissolved in dry THF (6.50 mL). Et$_3$N-3HF (33 µL, 0.19 mmol) was added dropwise and the reaction was followed by TCL and stopped in order to reduce as much as possible the proportion of the fully deprotected derivative. After 7 h of stirring at room temperature, AcOEt (15 mL) was added to the mixture and the organic layer was washed with water (10 mL) and brine (10 mL). The organic phase was dried (MgSO$_4$) and concentrated under vacuum. The residue obtained was purified by chromatography on silica gel (hexane/AcOEt 95/5 to 70/30) to give the mono-protected phloroglucinol 11a (37 mg, 61%) as a white solid. The fully deprotected derivative was isolated in 11% (3.20 mg).

R$_f$ (hexane/AcOEt 70/30) 0.6; $^1$H NMR (500 MHz; CDCl$_3$) $\delta_H$ 6.05 (s, 1H, CH$_{aro}$), 6.02-6.00 (m, 2H, CH$_{aro}$), 4.86 (br, 1H, OH), 3.73 (s, 3H, CH$_3$O), 1.29-1.20 (m, 3H, CH—Si), 1.09 (d, J=7.5 Hz, 18H, (CH$_3$)$_2$C); $^{13}$C NMR (125 MHz; CDCl$_3$) $\delta_c$ 161.3, 157.9, 157.2, 100.1, 98.8, 94.6, 55.2, 17.9, 12.6; HRMS (ESI-TOF) m/z: [M–H]$^-$ calcd. for C$_{16}$H$_{27}$O$_3$Si 295.1729; found 295.1730.

3-isopropoxy-5-(triisopropylsilyloxy)phenol 11b: The di-protected phloroglucinol 10b (100 mg, 0.21 mmol) was dissolved in dry THF (6 mL). Et$_3$N-3HF (68 µL, 0.42 mmol) was added to the mixture and the reaction was followed by TLC and stopped in order to reduce as much as possible the formation on the fully deprotected derivative. After 5 h of stirring at room temperature, 15 mL of AcOEt were added to the mixture and the organic layer was washed with water (10 mL) and brine (10 mL). The organic phase was dried (MgSO$_4$) and concentrated under vacuum. The residue obtained was purified by chromatography on silica gel (hexane/AcOEt 95/5) to give the mono-protected phloroglucinol 11b (42 mg, 62%) as uncolored oil. The fully deprotected derivative was isolated in 14% (5 mg).

R$_f$ (hexane/AcOEt 70/30) 0.7; $^1$H NMR (500 MHz; CDCl$_3$) $\delta_H$ 6.04 (t, J=2.5 Hz, 1H, CH$_{aro}$), 6.01 (t, J=2.5 Hz, 1H, CH$_{aro}$), 5.99 (t, J=2.5 Hz, 1H, CH$_{aro}$), 4.87 (br, 1H, OH), 4.44 (quint, J=6.0 Hz, 1H, CH$_{ip}$), 1.31 (d, J=6.0 Hz, 6H, (CH$_3$)$_2$C$_{ip}$), 1.28-1.20 (m, 3H, CH—Si), 1.10 (d, J=7.5 Hz, 18H, (CH$_3$)$_2$C$_{TIPS}$); $^{13}$C NMR (125 MHz; CDCl$_3$) $\delta_c$ 159.6, 157.9, 157.0, 100.7, 100.0, 96.6, 70.0, 22.0, 17.9, 12.6; HRMS (ESI-TOF) m/z: [M–H]$^-$ calcd. for C$_{18}$H$_{31}$O$_3$Si 323,2042; found 323.2045.

(4,7,10,13,16,19 Z)-3-methoxy-5-(triisopropylsilyloxy)phenyl docosa-4,7,10,13,16,19-hexaenoate 12a: Coupling of the protected phloroglucinol-OMe 11a (96 mg, 0.32 mmol) and DHA (106 mg, 0.32 mmol) following the general procedure, afforded 12a (120 mg, 60%) as a uncolored oil after purification on silica gel chromatography (hexane/AcOEt 99/1).

R$_f$ (hexane/ AcOEt 99/1) 0.28; $^1$H NMR (500 MHz; CDCl$_3$) $\delta_H$ 6.30 (s, 1H, CH$_{aro}$), 6.25-6.23 (m, 2H, CH$_{aro}$), 5.48-5.28 (m, 12H, CH═CH), 3.74 (s, 3H, CH$_3$O), 2.87-2.79 (m, 10H, CH$_2$ bis-allylic), 2.60-2.57 (m, 2H, CH$_2$—C═O), 2.52-2.48 (m, 2H, CH$_2$ allylic), 2.07 (quint, J=7.5 Hz, 2H, CH$_2$ allylic), 1.29-1.20 (m, 3H, CH—Si), 1.09 (d, J=7.4 Hz, 18H, (CH$_3$)$_2$C), 0.97 (t, J=7.5 Hz, 3H, CH$_3$); $^{13}$C NMR (125 MHz; CDCl$_3$) $\delta_c$ 171.2, 160.8, 157.4, 152.0, 132.0, 129.6, 128.5, 128.3, 128.2, 128.2, 128.1, 128.1, 128.0, 127.8, 127.5, 127.0, 106.3, 103.8, 100.4, 55.4, 34.3, 25.6, 25.6, 25.5, 22.7, 20.5, 17.8, 14.2, 12.6; HRMS (ESI-TOF) m/z: [M+H]$^+$ calcd. for C$_{38}$H$_{59}$O$_4$Si 607.4183; found 607.4185.

(4,7,10,13,16,19 Z)-3-isopropoxy-5-(triisopropylsilyloxy)phenyl docosa-4,7,10,13,16,19-hexaenoate 12b: Coupling of the mono-TIPS-mono-isopropyl-phloroglucinol 11b (100 mg, 0.31 mmol) and DHA (101 mg, 0.31 mmol) was performed with the general procedure and afforded 12b (132 mg, 67%) as an uncolored oil after purification on silica gel chromatography (hexane/AcOEt 99/1).

R$_f$ (hexane/AcOEt 99/1) 0.30; $^1$H NMR (500 MHz; CDCl$_3$) $\delta_H$ 6.29 (t, J=2.0 Hz,1H, CH$_{aro}$), 6.24 (t, J=2.0 Hz,1H, CH$_{aro}$), 6.21 (t, J=2.0 Hz,1H, CH$_{aro}$), 5.49-5.29 (m, 12H, CH═CH), 4.45 (quint, J=6.0 Hz, 1H, CH$_{ip}$), 2.88-2.81 (m, 10H, CH$_2$ bis-allylic), 2.60-2.57 (m, 2H, CH$_2$—C═O), 2.52-2.48 (m, 2H, CH$_2$ allylic), 2.08 (quint, J=7.5 Hz, 2H, CH$_2$ allylic), 1.32 (d, J=6.0 Hz, 6H, (CH$_3$)$_2$C$_{ip}$), 1.28-1.22 (m, 3H, CH—Si), 1.10 (d, J=7.5 Hz, 18H, (CH$_3$)$_2$C$_{TIPS}$), 0.98 (t, J=7.5 Hz, 3H, CH$_3$); $^{13}$C NMR (125 MHz; CDCl$_3$) $\delta_c$ 171.1, 159.1, 157.3, 151.9, 132.0, 129.6, 128.5, 128.3, 128.2, 128.2, 128.1, 128.0, 128.0, 127.8, 127.6, 127.0, 106.0, 105.3, 102.3, 70.1, 34.3, 25.6, 25.6, 25.5, 22.7, 21.9, 20.5, 17.9, 14.2, 12.6; HRMS (ESI-TOF) m/z: [M+H]$^+$ calcd. for C$_{40}$H$_{63}$O$_4$Si 635.4496; found 635.4502.

(4,7,10,13,16,19 Z)-3-hydroxy-5-methoxyphenyl docosa-4,7,10,13,16, 19-hexaenoate 13a: Deprotection of the protected DHA-phloroglucinol-OMe 12a (75 mg, 0.12 mmol) was performed with the general procedure and afforded 13a (49 mg, 88%) as an uncolored oil after purification on silica gel chromatography (hexane/AcOEt 90/10).

R$_f$ (hexane/AcOEt 80/20) 0.29; $^1$H NMR (500 MHz; CDCl$_3$) $\delta_H$ 6.25 (s, 1H, CH$_{aro}$), 6.22 (s, 1H, CH$_{aro}$), 6.18 (s, 1H, CH$_{aro}$), 5.49-5.28 (m, 12H, CH═CH), 5.21 (br, 1H, OH), 3.75 (s, 3H, CH$_3$O), 2.88-2.80 (m, 10H, CH$_2$ bis-allylic), 2.60 (t, J=7.3 Hz, 2H, CH$_2$—C═O), 2.52-2.46 (m, 2H, CH$_2$ allylic), 2.07 (quint, J=7.3 Hz, 2H, CH$_2$ allylic), 0.97 (t, J=7.5 Hz, 3H, CH$_3$); $^{13}$C NMR (125 MHz; CDCl$_3$) $\delta_c$ 171.8, 161.2, 157.2, 152.0, 132.0, 129.7, 128.5, 128.3, 128.2, 128.2, 128.0, 128.0, 127.9, 127.8, 127.4, 127.0, 101.9, 100.0, 99.4, 34.3, 25.6, 25.6, 25.5, 22.7, 20.5, 14.2; HRMS (ESI-TOF) m/z: [M+H]$^+$ calcd. for C$_{29}$H$_{39}$O$_4$ 451.2848; found 451.2851.

(4,7,10,13,16,19 Z)-3-hydroxy-5-isopropoxyphenyl docosa-4, 7,10,13,16,19-hexaenoate 13b: Deprotection of the protected DHA-phloroglucinol 12b (120 mg, 0.19 mmol) was performed through the general procedure and afforded 13b (82 mg, 90%) as an uncolored oil after purification on silica gel chromatography (hexane/AcOEt 90/10).

R$_f$ (hexane/AcOEt 90/10) 0.30; $^1$H NMR (500 MHz; CDCl$_3$) $\delta_H$ 6.25 (t, J=2.0 Hz, 1H, CH$_{aro}$), 6.21 (t, J=2.0 Hz, 1H, CH$_{aro}$), 6.17 (t, J=2.0 Hz,1H, CH$_{aro}$), 5.48-5.29 (m, 12H, CH═CH), 4.95 (br, 1H, OH), 4.47 (quint, J=6.0 Hz, 1H, CH$_{ip}$), 2.89-2.81 (m, 10H, CH$_2$ bis-allylic), 2.61-2.58 (m, 2H, CH$_2$—C═O), 2.54-2.48 (m, 2H, CH$_2$ allylic), 2.08 (quint, J=7.5 Hz, 2H, CH$_2$ allylic), 1.32 (d, J=6.0 Hz, 6H, (CH$_3$)$_2$C$_{ip}$), 0.98 (t, J=7.5 Hz, 3H, CH$_3$); $^{13}$C NMR (125 MHz; CDCl$_3$) $\delta_c$ 171.3, 159.6, 156.9, 152.1, 132.0, 129.7, 128.5, 128.3, 128.3, 128.2, 128.1, 128.0, 128.0, 127.8, 127.5, 127.0, 101.9, 101.5, 100.8, 70.2, 34.3, 25.6, 25.6, 25.6, 25.5, 22.7, 21.9, 20.5, 14.2; HRMS (ESI-TOF) m/z: [M−H]⁻ calcd. for $C_{31}H_{41}O_4$ 477.3005; found 477.3007.

(4,7,10,13,16,19 Z)-3,5-dimethoxyphenyl docosa-4,7,10,13,16,19-hexaenoate 15a: Coupling of the di-OMe-phloroglucinol 14a (47 mg, 0.30 mmol) and DHA (100 mg, 0.30 mmol) was performed with the general procedure and afforded 15a (110 mg, 77%) as an uncolored oil after purification on silica gel chromatography (hexane/AcOEt 97/3).

$R_f$ (hexane/AcOEt 95/5) 0.36; ¹H NMR (500 MHz; CDCl₃) $\delta_H$ 6.33 (t, J=2.0 Hz, 1H, $CH_{aro}$), 6.25 (d, J=2.0 Hz, 2H, $CH_{aro}$), 5.49-5.28 (m, 12H, CH=CH), 3.76 (s, 6H, s CH₃O), 2.88-2.79 (m, 10H, CH₂ bis-allylic), 2.60 (t, J=7.3 Hz, 2H, CH₂—C=O), 2.54-2.49 (m, 2H, CH₂ allylic), 2.07 (quint, J=7.3 Hz, 2H, CH₂ allylic), 0.97 (t, J=7.5 Hz, 3H, CH₃); ¹³C NMR (125 MHz; CDCl₃) $\delta_c$ 171.4, 161.0, 152.1, 131.9, 129.8, 128.5, 128.3, 128.2, 128.2, 128.0, 128.0, 127.9, 127.8, 127.4, 126.9, 100.1, 98.1, 55.4, 34.3, 25.6, 25.5, 25.4, 22.7, 20.4, 14.2; HRMS (ESI-TOF) m/z: [M+H]⁺ calcd. for $C_{30}H_{41}O_4$ 465.3005; found 465.3011.

(4,7,10,13,16,19 Z)-3,5-diisopropoxyphenyl docosa-4,7,10,13,16, 19-hexaenoate 15b: Coupling of the di-OiP-phloroglucinol 14b (96 mg, 0.45 mmol) and DHA (150 mg, 0.45 mmol) was performed with the general procedure and afforded 15b (168 mg, 70%) as an uncolored oil after purification on silica gel chromatography (hexane/AcOEt 97/3).

$R_f$ (hexane/AcOEt 95/5) 0.57; ¹H NMR (500 MHz; CDCl₃) $\delta_H$ 6.28 (s, 1H, $CH_{aro}$), 6.19 (s, 2H, $CH_{aro}$), 5.48-5.28 (m, 12H, CH=CH), 4.46 (quint, J=5.9 Hz, 2H, CH), 2.89-2.78 (m, 10H, CH₂ bis-allylic), 2.59 (t, J=7.4 Hz, 2H, CH₂—C=O), 2.53-2.48 (m, 2H, CH₂ allylic), 2.07 (quint, J=7.3 Hz, 2H, CH₂ allylic), 1.31 (d, J=6.0 Hz, 12H, (CH₃)₂C), 0.97 (t, J=7.5 Hz, 3H, CH₃); ¹³C NMR (125 MHz; CDCl₃) $\delta_c$ 171.2, 159.3, 152.1, 131.9, 129.6, 128.5, 128.3, 128.2, 128.2, 128.0, 128.0, 127.9, 127.8, 127.5, 126.9, 101.4, 101.2, 70.0, 34.2, 25.6, 25.5, 25.4, 22.7, 21.9, 20.5, 14.2; HRMS (ESI-TOF) m/z: [M+H]⁺ calcd. for $C_{34}H_{49}O_4$ 521.3631; found 521.3636.

Example 2-1: Synthesis of Propyl-DHA-Phloroglucinol Conjugate 5-propylbenzene-1,3-diol (9c): To a suspension of phloroglucinol (0.40 g, 3.17 mmol) in dioxane (1 mL) was added a prepared solution of Propanol saturated with dry HCl (gaz) (4 mL). The reaction was stirred at room temperature during 4 h. An additional amount of the saturated HCl solution was added (1 mL) and the reaction was kept at 70° C. for 1 h. The solvents were evaporated under vacuum and the residue obtained was purified by chromatography on silica gel (CH₂Cl₂/MeOH 98/2) to give 9c (154 mg, 65%) as a white solid.

$R_F$ (CH₂Cl₂/MeOH 95/5) 0.6; ¹H NMR (500 MHz; MeOD) $\delta_H$ 5.87 (s, 3H, $CH_{aro}$), 4.89 (br, 2H, OH), 3.82 (t, J=6.5 Hz, 2H, CH₂—O), 1.74 (sex, J=7.2 Hz, 2H, CH₂—C), 1.01 (t, J=7.5 Hz, 3H, CH₃).

5-propyl-1,3-bis(triisopropylsilyloxy)benzene (10c): Phloroglucinol-OPropyl 9c (300 mg, 1.78 mmol) was dissolved in dry CH₂Cl₂ (30 mL). Diisopropylethylamine (641 µl, 3.75 mmol) and TIPS-OTf (1.01 mL, 3.75 mmol) were added dropwise to the solution and the reaction mixture was stirred at room temperature during 3 h. AcOEt (30 mL) was added to the mixture and the organic layer was washed with water (20 mL) and brine (20 mL). The organic phase was dried (MgSO₄) and concentrated under vacuum. The residue obtained was purified by chromatography on silica gel (Pentane/AcOEt 99.5/0.5) to give the di-protected phloroglucinol-OPropyl 10c (402 mg, 47%) as an uncolored oil, with was directly engaged in the selective monodeprotection.

3-propyl-5-(triisopropylsilyloxy)phenol (11c): The di-protected phloroglucinol 10c (400 mg, 0.83 mmol) was dissolved in dry THF (30 mL). Et₃N-3HF (277 µL, 1.66 mmol) was added dropwise and the reaction was followed by TCL and stopped in order to reduce as much as possible the proportion of the fully deprotected derivative. After 7 h of stirring at room temperature, AcOEt (30 mL) was added to the mixture and the organic layer was washed with water (20 mL) and brine (20 mL). The organic phase was dried (MgSO₄) and concentrated under vacuum. The residue obtained was purified by chromatography on silica gel (pentane/AcOEt 97/3) to give the mono-protected phloroglucinol 11c (137 mg, 51%) as a white oil.

$R_f$ (hexane/AcOEt 9.5/0.5) 0.5; ¹H NMR (500 MHz; CDCl₃) $\delta_H$ 6.04 (t, J=2.5 Hz, 1H, $CH_{aro}$), 6.01 (t, J=2 Hz,

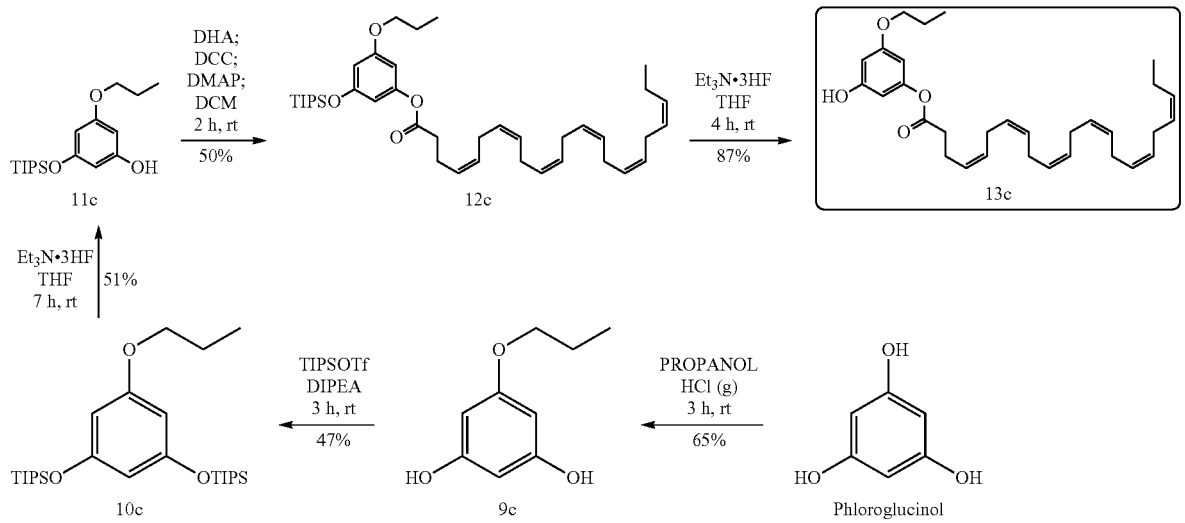

1H, CH$_{aro}$), 5.98 (t, J=2 Hz, 1H, CH$_{aro}$), 4.63 (br, 1H, OH), 3.83 (t, J=6.5 Hz, 2H, CH$_2$O),1.76 (sext, J=7 Hz, 2H, CH$_2$—C), 1.27-1.20 (m, 3H, CH—Si), 1.09 (d, J=7 Hz, 18H, (CH$_3$)$_2$C), 1.01 (t, J=7.5 Hz, 3H, CH$_3$).

(4,7,10,13,16,19Z)-3-propoxy-5-((triisopropylsilyl)oxy)phenyl docosa-4,7,10,13,16,19-hexaenoate (12c)

12c

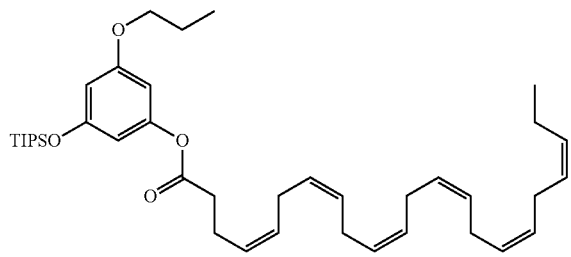

Chemical Formula: C$_{40}$H$_{62}$O$_4$Si
Molecular Weight: 635.00 g·mol$^{-1}$

Coupling of the mono-protected phloroglucinol-propyl 11c (100 mg, 0.30 mmol) and DHA (109 mg, 0.33 mmol) was performed with the general procedure and afforded 12c (96 mg, 50%) as a yellow oil after purification on silica gel chromatography (Hexane/AcOEt 99/1).

R$_f$ (Hexane/AcOEt 95/5) 0.45; $^1$H NMR (500 MHz, CDCl$_3$) δ 6.31 (t, J=2.2, 1H), 6.26 (t, J=2.1, 1H), 6.23 (t, J=2.1, 1H), 5.54-5.26 (m, 12H), 3.85 (t, J=6.6, 2H), 2.93-2.77 (m, 10H), 2.61-2.58 (m, 2H), 2.55-2.47 (m, 2H), 2.14-2.02 (m, 2H), 1.80-1.75 (m, 4H), 1.32-1.20 (m, 6H), 1.11 (d, J=7.3, 18H), 1.02 (t, J=7.4, 3H), 0.98 (t, J=7.5, 3H); $^{13}$C NMR (126 MHz, CDCl$_3$) δ 171.34, 160.51, 157.45, 152.05, 132.12, 129.74, 128.66, 128.44, 128.37, 128.36, 128.20, 128.19, 128.18, 128.12, 127.99, 127.70, 127.13, 106.14, 104.32, 101.16, 69.73, 34.42, 25.76, 25.74, 25.65, 22.90, 22.61, 18.01, 18.00, 14.40, 12.73, 10.62.

(4,7,10,13,16,19Z)-3-hydroxy-5-propoxyphenyl docosa-4,7,10,13,16, 19-hexaenoate (13c)

13c

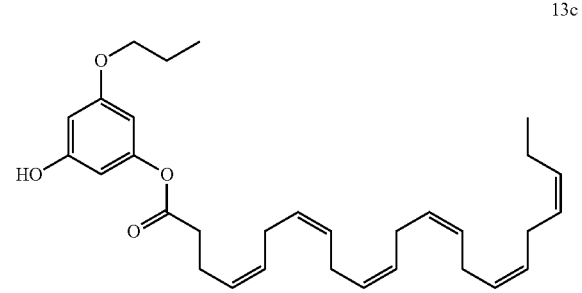

Chemical Formula: C$_{31}$H$_{42}$O$_4$
Molecular Weight: 478.66 g·mol$^{-1}$

Deprotection of the protected DHA-phloroglucinol-propyl 12c (95 mg, 0.14 mmol) was performed with the general procedure and afforded 13c (58 mg, 87%) as an uncoloured oil after 4h30 of reaction and purification on silica gel chromatography (Cyclohexane/AcOEt 95/5).

R$_f$ (Hexane/AcOEt 90/10) 0.21; $^1$H NMR (500 MHz, CDCl$_3$) δ 6.23 (m, 1H), 6.20 (m, 1H), 6.15 (m, 1H), 5.52-5.27 (m, 12H), 3.83 (t, J=6.5, 2H), 2.92-2.78 (m, 10H), 2.66-2.57 (m, 1H), 2.57-2.47 (m, 2H), 2.09-2.06 (m, 3H), 1.79-1.73 (m, 3H), 1.03-0.95 (m, 6H); $^{13}$C NMR (126 MHz, CDCl$_3$) δ 172.12, 160.87, 157.37, 152.07, 132.17, 129.88, 128.69, 128.48, 128.40, 128.38, 128.20, 128.20, 128.09, 128.00, 127.55, 127.14, 101.79, 100.66, 100.02, 69.84, 34.44, 25.75, 25.73, 22.87, 22.54, 20.67, 14.39, 10.58.

Example 3: Synthesis of DHA-Resveratrol Conjugate

As presented above, the trapping mechanism of a carbonyl stressor (AtR) by the phloroglucinol would require the presence of a resorcinol pattern on the phenolic backbone. Such a framework is found in many other naturally occurring polyphenols (ring A of flavonoids, for instance), but also in stilbenoids and especially in resveratrol, which is a perfect vinylogous of phloroglucinol. Because of the importance of the resorcinol reactivity to scavenge AtR, DHA was linked to the hydroxyl at the 4' position of resveratrol, to let 3- and 5-hydroxyl groups available to form the chromene derivative. Compared to phloroglucinol series, the strategy envisaged for the stilbenoid synthesis presents additional difficulties since it requires a selective protection of the phenol at the 3 and 5 positions, despite the close reactivity of the three hydroxyl groups of resveratrol. To overcome this drawback, resveratrol was regio-selectively acylated by *Candida antartica* lipase B (CALB or Novozyme 435, which present high selectivity for the hydroxyl group at the 4'-position) in the presence of vinyl acetate to afford a single protected product, the 4'-O-acetylresveratrol 16, in 57%. Hydroxyls at positions 3 and 5 were protected using TIPS-OTf to obtained 17 which was subjected to acetyl deprotection in the presence of a methanolic solution of MeONa in excellent yield. The 4'-deprotected resveratrol 18 was then coupled to DHA (19), as performed in the phloroglucinol series, and subjected to TIPS deprotection to afford resveratrol-DHA 20 with 20% overall yield.

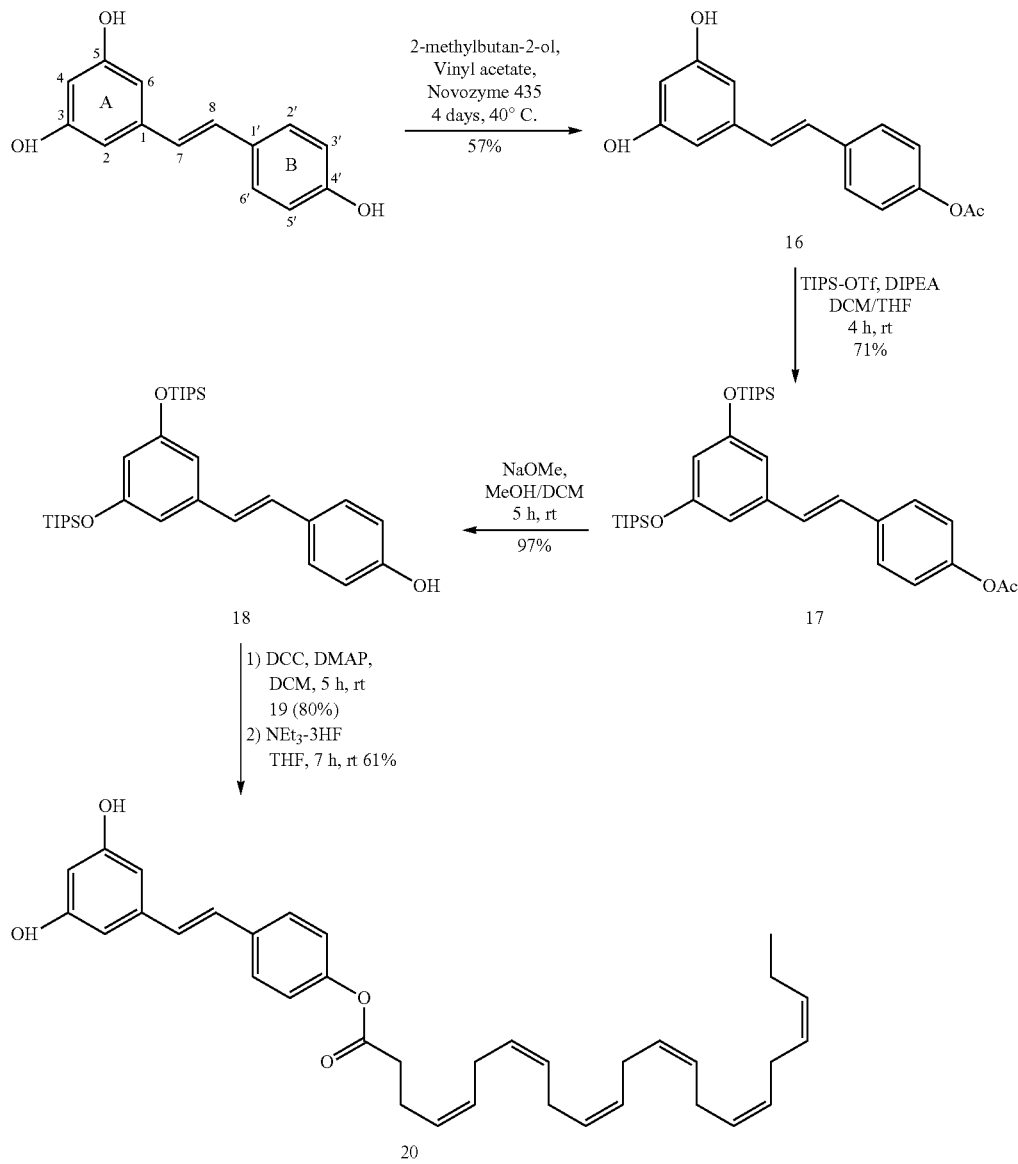

The implemented steps as mentioned above are described hereafter in detail.

(E)-4-(3,5-dihydroxystyryl)phenyl acetate 16: Resveratrol (200 mg, 0.88 mmol) was dissolved in 2-methylbutan-2-ol (20 mL) and vinyl acetate (5 mL) in presence of the supported lipase *Candida Antarctica* (Novozyme 435, CalB, 1 g). The mixture was stirred with a rotary evaporator at 40° C. during 4 days. The lipase was filtered off and washed with AcOEt twice and diethyl ether. The filtrate obtained was concentrated under reduced pressure and the residue obtained was purified by chromatography on silica gel ($CH_2Cl_2$/MeOH 99/1 to 90/10) to give the 4′-O-acetyl resveratrol 16 (135 mg, 57%) as white solid. 27% of starting material were recovered after purification (5 mg).

$R_f$ ($CH_2Cl_2$/MeOH 95/5) 0.30; $^1$H NMR (500 MHz; $CD_3OD$) $\delta_H$ 7.54 (d, J=7.6 Hz, 2H, $H_{2'}$ and $H_{6'}$), 7.07 (d, J=7.6 Hz, 2H, $H_{3'}$ and $H_{5'}$) 7.04 (d, J=16.2 Hz, 1H, $H_8$), 6.97 (d, J=16.2 Hz, 1H, $H_7$), 6.49 (s, 2H, $H_2$, $H_6$), 6.21-6.19 (m, 1H, $H_4$), 2.27 (s, 3H, $CH_{3(OAc)}$); $^{13}$C NMR (125 MHz; MeOD) $\delta_C$ 171.1, 159.7, 151.5, 140.6, 136.58, 130.24, 128.3, 128.3, 122.9, 106.1, 103.2, 20.9; HRMS (ESI-TOF) m/z: [M+H]$^+$ calcd. for $C_{16}H_{15}O_4$ 271.0964; found 271.0972.

(E)-4-(3,5-bis(triisopropylsilyloxy)styryl)phenyl acetate 17: Resveratrol-4′-OAc 16 (100 mg, 0.37 mmol) was dissolved in dry THF (6 mL). Triethylamine (109 μL, 0.78 mmol) and TIPS-OTf (208 μL, 0.78 mmol) were added dropwise to the solution and the reaction mixture was stirred at room temperature during 2 h. A same amount of $Et_3N$ and TIPS-OTf were added to reach completion of the reaction. After 3 additional hours of reaction, the solvent was evaporated under reduced pressure. The residue obtained was dissolved in 10 mL of AcOEt and washed with water (10 mL) and brine (10 mL). The organic phase was dried ($MgSO_4$) and concentrated under vacuum. The residue obtained was purified by chromatography on silica gel (pentane/AcOEt 80/20) to give the protected resveratrol 17 (152 mg, 71%) as an uncolored oil.

$R_f$ (pentane/AcOEt 95/5) 0.5; $^1$H NMR (500 MHz; $CDCl_3$) $\delta_H$ 7.51 (d, J=8.0 Hz, 2H, $H_{2'}$ and $H_{6'}$), 7.09 (d, J=8.0

Hz, 2H, H$_3'$ and H$_5'$), 6.98 (d, J=16.3 Hz, 1H, H$_8$), 6.92 (d, J=16.3 Hz, 1H, H$_7$), 6.65 (s, 2H, H$_2$, H$_6$), 6.37-6.36 (m, 1H, H$_4$), 2.31 (s, 3H, CH$_{3(OAc)}$), 1.26 (m, 6H, CH—Si), 1.12 (d, J=7.6 Hz, 36H, (CH$_3$)$_2$C); $^{13}$C NMR (125 MHz; CDCl$_3$) δ$_c$ 169.7, 157.3, 150.2, 139.0, 135.3, 129.3, 127.8, 127.7, 122.0, 111.6, 111.5, 21.4, 18.2, 13.9; HRMS (ESI-TOF) m/z: [M+H]$^+$ calcd. for C$_{34}$H$_{55}$O$_4$Si$_2$ 583.3633; found 583.3640.

(E)-4-(3,5-bis(triisopropylsilyloxy)styryl)phenol 18: The protected resveratrol 17 (239 mg, 0.41 mmol) was dissolved in dry MeOH (2 mL) and CH$_2$Cl$_2$ (1 mL). A catalytic amount of sodium methanolate (6.60 mg, 0.12 mmol) was added to the solution and the reaction mixture was stirred at room temperature during 2 h. An amount of NaOMe was added to reach completion of the reaction. After 5 h of reaction, the solvent was evaporated under reduced pressure. The residue obtained was purified by chromatography on silica gel (Hexane/AcOEt 95/5) to give the 4'-deprotected resveratrol 18 (214 mg, 97%) as an uncolored oil.

R$_f$ (hexane/AcOEt 90/10) 0.41; $^1$H NMR (500 MHz; CD$_3$OD) δ$_H$ 7.38 (d, J=8.5 Hz, 2H, H$_2'$ and H$_6'$), 6.95 (d, J=16.2 Hz, 1H, H$_8$), 6.84 (d, J=16.2 Hz, 1H, H$_7$), 6.77 (d, J=8.5 Hz, 2H, H$_3'$ and H$_5'$), 6.64-6.63 (m, 2H, H$_2$, H$_6$), 6.30-6.29 (m, 1H, H$_4$), 1.30-1.22 (m, 6H, CH—Si), 1.14 (d, J=7.5 Hz, 36H, (CH$_3$)$_2$C); $^{13}$C NMR (125 MHz; MeOD) δ$_c$158.5, 158.3, 141.3, 130.1, 129.9, 129.0, 126.5, 116.5, 112.1, 111.4, 18.4, 13.9; HRMS (ESI-TOF) m/z: [M+H]$^+$ calcd. for C$_{32}$H$_{53}$O$_3$Si$_2$ 541.3527; found 541.3536.

(4,7,10,13,16,19 Z)-4-((E)-3,5-bis(triisopropylsilyloxy) styryl)phenyl docosa-4,7,10,13,16,19-hexaenoate 19: Coupling of the di-protected resveratrol 18 (103 mg, 0.18 mmol) and DHA (67 mg, 0.20 mmol) was performed with the general procedure and afforded 19 (130 mg, 80%) as an uncolored oil after purification on silica gel chromatography (hexane/AcOEt 99/1).

R$_f$ (hexane/AcOEt 95/5) 0.73; $^1$H NMR (500 MHz; CDCl$_3$) δ$_H$ 7.50 (d, J=8.5 Hz, 2H, H$_2'$ and H$_6'$), 7.07 (d, J=8.4 Hz, 2H, H$_3'$ and H$_5'$), 6.98 (d, J=16.5 Hz, 1H, H$_8$), 6.92 (d, J=16.5 Hz, 1H, H$_7$), 6.64 (d, J=2.3 Hz, 2H, H$_2$, H$_6$), 6.36 (t, J=2.3 Hz 1H, H$_4$), 5.50-5.29 (m, 12H, CH=CH), 2.90-2.80 (m, 10H, CH$_2$ bis-allylic), 2.64 (t, J=7.0 Hz, 2H, CH$_2$—C=O), 2.55-2.51 (m, 2H, CH$_2$ allylic), 2.08 (quint, J=7.0 Hz, 2H, CH$_2$allylic), 1.29-1.22 (m, 6H, CH—Si), 1.12 (d, J=7.5 Hz, 36H, (CH$_3$)$_2$C); 0.98 (t, J=7.5 Hz, 3H, CH$_3$); $^{13}$C NMR (125 MHz; CDCl$_3$) δ$_c$ 171.8, 157.4, 150.4, 139.1, 135.3, 132.3, 130.0, 129.3, 128.9, 128.7, 128.6, 128.6, 128.4, 128.4, 128.3, 128.2, 127.9, 127.8, 127.7, 127.3, 122.0, 111.7, 111.6, 34.6, 25.9, 25.9, 25.8, 23.1, 20.9, 18.2, 14.6, 13.0; HRMS (ESI-TOF) m/z: [M+H]$^+$ calcd. for C$_{54}$H$_{83}$O$_4$Si$_2$ 851.5824; found 851.5825.

(4,7,10,13,16,19 Z)-4-((E)-3,5-dihydroxyphenylstyryl) phenyl docosa-4, 7,10,13,16,19-hexaenoate 20: Deprotection of the protected DHA-resveratrol 19 (142 mg, 0.17 mmol) was performed with the general procedure and afforded 20 (55 mg, 61%) as white solid after 7 h of reaction and purification on silica gel chromatography (hexane/AcOEt 95/5 to 70/30).

R$_f$ (hexane/AcOEt 70/30)=0.22; $^1$H NMR (500 MHz; CDCl$_3$) δ$_H$ 7.45 (d, J=8.6 Hz, 2H, H$_2'$ and H$_6'$), 7.07 (d, J=8.5 Hz, 2H, H$_3'$ and H$_5'$), 6.95 (d, J=16.2 Hz, 1H, H$_8$), 6.85 (d, J=16.2 Hz, 1H, H$_7$), 6.51 (d, J=2.1 Hz, 2H, H$_2$, H$_6$), 6.26 (t, J=2.1 Hz, 1H, H$_4$), 5.52-5.29 (m, 12H, CH$_2$ bis-allylic), 5.13 (br, 2H, OH), 2.90-2.80 (m, 10H, CH$_2$ allylic), 2.66 (t, J=7.4 Hz, 2H, CH$_2$—C=O), 2.52-2.56 (m, 2H, CH$_2$ allylic), 2.08 (quint, J=7.8 Hz, 2H, CH$_2$ allylic), 0.98 (t, J=7.3 Hz, 3H, CH$_3$); $^{13}$C NMR (125 MHz; CDCl$_3$) δ$_c$ 172.3, 157.3, 150.4, 140.0, 135.2, 132.4, 130.1, 128.9, 128.7, 128.6, 128.6, 128.6, 128.5, 128.4, 128.4, 128.3, 128.2, 127.8, 127.7, 127.3, 122.1, 106.4, 102.7, 34.6, 25.9, 25.8, 23.1, 20.9, 14.6; HRMS (ESI-TOF) m/z: [M+H]$^+$ calcd. for C$_{36}$H$_{43}$O$_4$ 539.3155; found 539.3160.

Example 3-1: Synthesis of DHA-Resveratrol Conjugate at the 3 Position

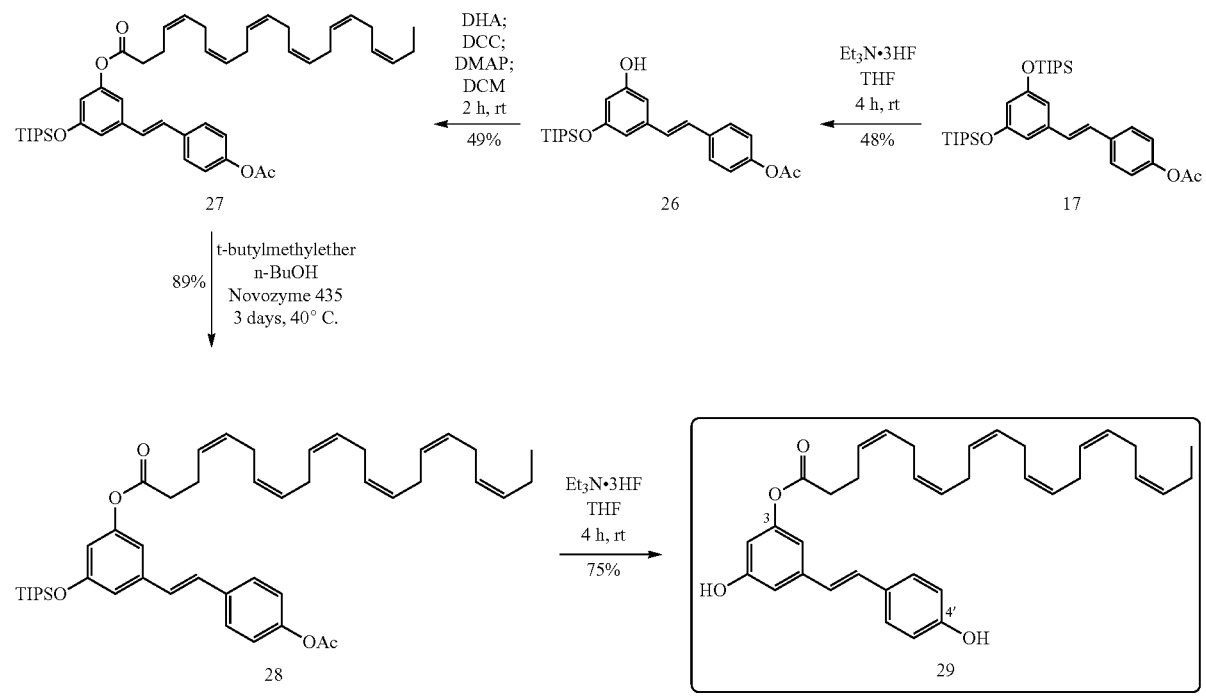

(E)-4-(3-hydroxy-5-((triisopropylsilyl)oxy)styryl)phenyl acetate (26)

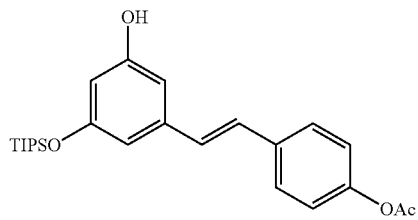

26

Chemical Formula: C$_{25}$H$_{34}$O$_4$Si
Molecular Weight: 426.62 g·mol$^{-1}$

The protected resveratrol 17 (1 g, 1.7 mmol) of Example 3 was dissolved in dry THF (60 mL), was added dropwise triethylammonium trihydrofluoride (554 µL, 3.4 mmol). The reaction was stirred at room temperature during 3 h. AcOEt (60 mL) was added to the mixture and the organic layer was washed with water (20 mL) and brine (20 mL). The organic phase was dried on MgSO$_4$ and concentrated under vacuum. The residue obtained was purified by chromatography on silica gel (Cyclohexane/AcOEt 95/5 to 80/20) to give the mono-protected resveratrol 26 (350 mg, 48%) as a white solid. The di-protected resveratrol was isolated in 26% as a white solid (118 mg).

R$_f$ (Hexane/AcOEt 70/30) 0.6; $^1$H NMR (500 MHz, CDCl$_3$) δ 7.48 (d, J=8.5 Hz, 2H), 7.08 (d, J=8.5 Hz, 2H), 6.92 (q, J=15.0 Hz, 2H), 6.59 (s, 1H), 6.55 (s, 1H), 6.32 (t, J=2.2 Hz, 1H), 5.35 (s, 1H), 2.32 (s, 3H), 1.33-1.22 (m, 3H), 1.12 (d, J=7.3 Hz, 18H); $^{13}$C NMR (126 MHz, CDCl$_3$) δ 170.23, 157.52, 156.89, 150.06, 139.24, 135.21, 128.88, 127.92, 127.61, 121.85, 111.26, 107.01, 106.28, 21.30, 18.06, 12.78.

(4,7,10,13,16,19Z)-3-((E)-4-acetoxystyryl)-5-((triisopropylsilyl)oxy)phenyl docosa-4,7,10,13,16,19-hexaenoate (27)

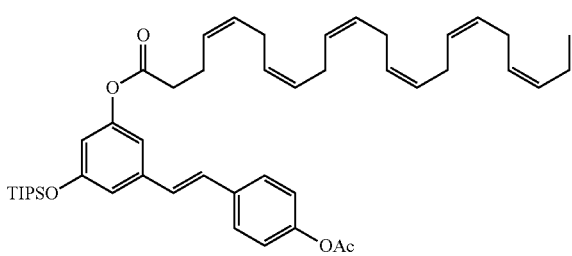

27

Chemical Formula: C$_{47}$H$_{64}$O$_5$Si
Molecular Weight: 737.09 g·mol$^{-1}$

Coupling of the mono-protected resveratrol 26 (470 mg, 1.1 mmol) and DHA (397 mg, 1.2 mmol) was performed with the general procedure and afforded 27 (391 mg, 49%) as a white solid after purification on silica gel chromatography (Cyclohexane/AcOEt 98/2).

R$_f$ (Hexane/AcOEt 90/10) 0.5; $^1$H NMR (500 MHz, CDCl$_3$) δ 7.49 (d, J=8.7 Hz, 2H), 7.08 (d, J=8.6 Hz, 2H), 6.97 (q, J=16.2 Hz, 2H), 6.85 (t, J=1.9 Hz, 2H), 6.53 (t, J=2.1Hz, 1H), 5.54-5.22 (m, 12H), 2.93-2.76 (m, 10H), 2.63-2.60 (m, 2H), 2.58-2.49 (m, 2H), 2.13-2.01 (m, 2H), 1.56 (s, 3H), 1.31-1.25 (m, 3H), 1.12 (d, J=7.3 Hz, 18H), 0.97 (t, J=7.5, 3H); $^{13}$C NMR (126 MHz, CDCl$_3$) δ 171.44, 169.55, 157.06, 151.81, 150.32, 139.23, 134.91, 132.15, 129.80, 128.70, 128.67, 128.48, 128.39, 128.38, 128.28, 128.20, 128.18, 128.11, 127.99, 127.68, 127.66, 127.13, 121.93, 115.79, 112.89, 112.26, 34.45, 25.77, 25.76, 25.74, 25.65, 22.90, 21.27, 20.68, 18.04, 14.41, 12.75.

(4,7,10,13,16,19Z)-3-((E)-4-hydroxystyryl)-5-((triisopropylsilyl)oxy)phenyl docosa-4,7,10,13,16,19-hexaenoate (28)

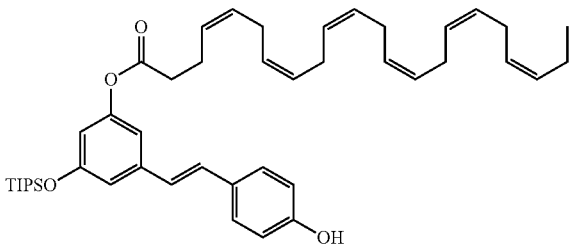

28

Chemical Formula: C$_{45}$H$_{62}$O$_4$Si
Molecular Weight: 695.06 g·mol$^{-1}$

The protected DHA-resveratrol 27 (345 mg, 0.47 mmol) was dissolved in t-butylmethylether (55 mL) and n-BuOH (2 mL). The supported lipase *Candida Antarctica* (Novozyme 435, CalB, 345 mg) was added to this solution and the mixture was stirred with a rotary evaporator at 40° C. during 3 days. The lipase was filtered off and washed with 5×30 mL AcOEt and 2×30 mL diethyl ether. The filtrate obtained was concentrated under reduced pressure and the residue obtained was purified by chromatography on silica gel (Cyclohexane/AcOEt 95/5 to 90/10) to give the compound 28 (291 mg, 89%) as a yellow oil.

R$_f$ (Hexane/AcOEt 90/10) 0.55; $^1$H NMR (500 MHz, CDCl$_3$) δ 7.37 (d, J=8.6 Hz, 2H), 6.96 (d, J=16.2 Hz, 1H), 6.88-6.78 (m, 5H), 6.50 (t, J=2.1 Hz, 1H), 5.52-5.26 (m, 12H), 2.95-2.74 (m, 10H), 2.67-2.59 (m, 2H), 2.54-2.52 (m, 2H), 2.14-2.00 (m, 2H), 1.34-1.20 (m, 3H), 1.11 (d, J=7.3 Hz, 18H), 0.97 (t, J=7.5 Hz, 3H); $^{13}$C NMR (126 MHz, CDCl$_3$) δ 171.54, 157.01, 155.52, 151.75, 139.68, 132.15, 130.09, 129.79, 129.18, 128.67, 128.47, 128.38, 128.37, 128.20, 128.18, 128.16, 128.12, 127.99, 127.69, 127.12, 125.99, 115.72, 115.52, 112.42, 112.04, 34.46, 25.76, 25.75, 25.73, 25.64, 22.90, 20.67, 18.03, 14.39, 12.75.

(4,7,10,13,16,19Z)-3-hydroxy-5-((E)-4-hydroxystyryl)phenyl docosa-4,7,10,13,16,19-hexaenoate (29)

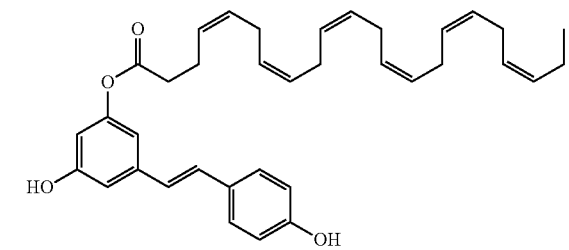

29

Chemical Formula: C$_{36}$H$_{42}$O$_4$
Molecular Weight: 538.72 g·mol$^{-1}$

Deprotection of the protected DHA-resveratrol 28 (330 mg, 0.47 mmol) was performed with the general procedure and afforded 29 (191 mg, 75%) as a white solid after 4h30 of reaction and purification on silica gel chromatography (Cyclohexane/AcOEt 80/20).

$R_f$ (Hexane/AcOEt 70/30) 0.33; $^1$H NMR (500 MHz, CDCl$_3$) δ 7.34 (d, J=8.6, 2H), 6.95 (d, J=16.3, 1H), 6.83-6.73 (m, 5H), 6.46 (t, J=2.1, 1H), 5.55-5.25 (m, 12H), 5.12 (d, J=21.8, 2H), 2.95-2.74 (m, 10H), 2.60-2.66 (m, 2H), 2.59-2.49 (m, 2H), 2.11-2.03 (m, 2H), 1.64 (s, 2H), 0.97 (t, J=7.5, 3H); $^{13}$C NMR (126 MHz, CDCl$_3$) δ 172.03, 156.61, 155.65, 151.87, 140.32, 132.22, 129.95, 129.92, 129.68, 128.73, 128.54, 128.44, 128.43, 128.26, 128.23, 128.23, 128.12, 128.03, 127.59, 127.16, 125.50, 34.49, 25.80, 25.78, 25.76, 25.68, 22.94, 20.71, 14.43.

Example 4: Synthesis of 1-phloroglucinol-2-DHA-glycerophosphatidyl-choline Conjugate DHA could accumulate in retina and brain through specific uptake of DHA-containing lysophosphatidylcholine (1-Lyso-2-DHA-PC or LysoPCDHA 21). Since DHA at the sn-2 position of LysoPCDHA, is considered as the physiological form of this polyunsaturated LysoPC, the coupling reaction of the phenolic moiety was performed at the sn-1 position. A method was developed, based on the sn1-LysoPCDHA 21, perfect intermediate to access the desired lipophenol from a chemical coupling with a phloroglucinol bearing an acidic linker. To quantitatively obtain compound 21, the enzymatic hydrolysis was performed in EtOH/H$_2$O 95/5. Using 200% (w/w) of enzyme and a reaction time of 40 h, the reaction led to 50% of purified LysoPC-DHA 21. Adding another portion of enzyme after 9 h and reducing the overall reaction time to 29 h, we increased the yield of LysoPC-DHA up to 85%. It appears that longer reaction time facilitates migration of DHA to the sn-1 position, to to form 1-DHA-2-LysoPC which, in turn, becomes the substrate of lipozyme for the regeneration of glycerophosphocholine. HPLC monitoring of the crude material revealed that in those conditions a very small proportion of migration was observed after 29 h of reaction. Moreover, according to HMBC NMR analysis of isolated 21, the DHA at the sn-2 position was confirmed by the presence of a coupling between the carbon of the carboxyl function of DHA and the CH proton of the glycerol moiety.

A short linker was selected to link both lipidic and phenolic parts in order to keep hydrophilic properties at the sn-1 position, to limit lipophilicity and to mimic as much as possible the physiological vector LysoPCDHA. A glutaryl linker was introduced on the phloroglucinol backbone using glutaric anhydride in the presence of DMAP (23). Then, the coupling step afforded the phospholipid conjugate 24 (65%) which was subjected to the deprotection of the TIPS group and led to the desired 1-glutaryl-phloroglucinol-2-DHA-PC 25 with an overall yield of 20% on 6 steps starting from commercially available compounds.

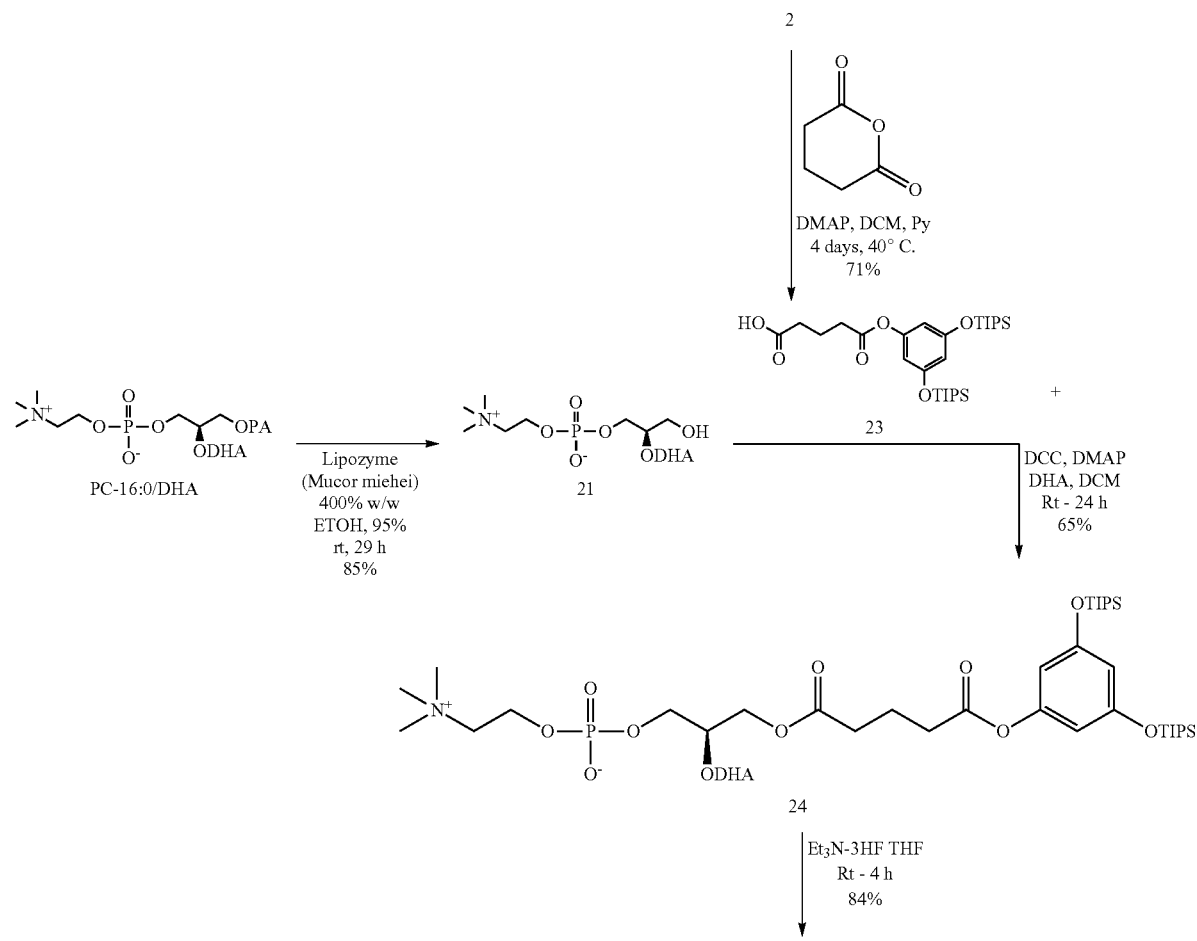

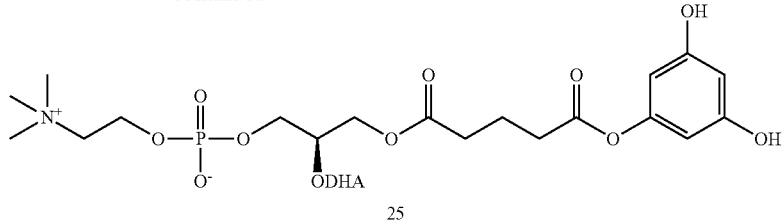

25

1-lyso-2-docosahexaenoyl-sn-glycero-3-phosphatidylcholine 21: The commercially available (Coger, France) PC-16:0-DHA (25 mg, 0.03 mmol) was dissolved in ethanol 96% (250 µL) of in presence of the supported lipozyme (immobilized from *Mucor miehei*) (25 mg). The mixture was stirred at room temperature during 9 h and an additional amount of supported enzyme (25 mg) was added to the mixture. After 29 h of overall reaction, the supported enzyme was filtered off and washed with absolute EtOH (3×3 mL) and chloroforme (3×3 mL). The filtrate was concentrated under vacuum and purified on Sepak SiOH cartridge (CHCl$_3$/MeOH 100/0 to 60/40) to give the sn1-Lyso-PC-DHA 21 (15 mg, 85%) as an uncoloured oil. 15% of starting material (4 mg) was recovered after the purification.

R$_f$ (CHCl$_3$/MeOH/H$_2$O 65/25/4) 0.19; $^1$H NMR (500 MHz; CDCl$_3$) δ$_H$ 5.41-5.29 (m, 12H, CH=CH), 4.96-4.91 (m, 1H, CH—O), 4.34-4.28 (m, 2H, CH$_2$—O), 4.06-4.00 (m, 1H, CH$_{2(a)}$—O), 3.98-3.92 (m, 1H, CH$_{2(b)}$—O), 3.80-3.75 (m, 2H, CH$_2$—N), 3.69-3.65 (m, 2H, CH$_2$—O), 3.32 (s, 9H, (CH$_3$)$_3$—N$^+$), 2.85-2.79 (m, 10H, CH$_2$ bis-allylic), 2.37-2.34 (m, 4H, CH$_2$—C=O and CH$_2$ allylic), 2.07 (quint, J=7.5 Hz, 2H, CH$_2$ allylic), 0.97 (t, J=7.5 Hz, 3H, CH$_3$); $^{13}$C NMR (125 MHz; CDCl$_3$) δ$_c$ 172.9, 132.2, 129.5, 128.8, 128.6, 128.5, 128.5, 128.3, 128.3, 128.2, 128.1, 128.1, 127.2, 73.7, 66.4, 63.3, 60.0, 59.6, 54.5, 34.3, 25.8, 25.8, 25.8, 25.8, 25.8, 22.8, 20.8, 14.5; HRMS (ESI-TOF) m/z: [M+H]$^+$ calcd. for C$_{30}$H$_{51}$NO$_7$P 568.3403; found 568.3409; HPLC rt: 25.80 min, (Atlantis C18 5 µm (4.6×250 mm), A: MeOH/H$_2$O/ACN 90/35/2.5, B: MeOH/H$_2$O/ACN 100/4/2.5, t$_{0'=100/0}$, t$_{15'=100/0}$, t$_{30'=0/100}$, t$_{50'0/100}$, detection 205 nm).

5-(3,5-bis(triisopropylsilyloxy)phenoxy)-5-oxopentanoic acid 23: The di-protected phloroglucinol 2 (100 mg, 0.23 mmol) was dissolved in CH$_2$Cl$_2$ (5 mL) in presence of pyridine (27 µL, 0.23 mmol). Glutaric anhydride (39 mg, 0.34 mmol) and DMAP (3 mg, 0.02 mmol) were added to the solution at room temperature and the reaction was heated at 40° C. Additional equivalent of reagents (1.5 equiv. for glutaric anhydride and 0.1 equiv. for DMAP) were added after one day of stirring. The reaction was stopped after 4 days by addition of water (10 mL). The organic phase was washed with water and brine, dried (MgSO$_4$) and concentrated under vacuum. The residue obtained was purified by chromatography on silica gel (pentane/AcOEt 90/10) to give the di-protected glutarate phloroglucinol 23 (90 mg, 71%) as a uncolored oil.

R$_f$ (pentane/AcOEt 60/40) 0.50; RMN $^1$H, CDCl$_3$, 500 MHz; δ ppm: 6.28 (t, J=2.2 Hz, 1H, CH$_{aro}$), 6.25 (d, J=2.2 Hz, 2H, CH$_{aro}$), 2.61 (t, J=7.4 Hz, 2H, CH2$_{glut}$), 2.51 (t, J=7.3 Hz, 2H, CH$_{2glut}$), 2.06 (quint, J=7.3 Hz, 2H, CH$_{2glut}$), 1.27-1.20 (m, 6H, CH—Si), 1.08 (d, J=7.3 Hz, 36H, (CH$_3$)$_2$C); $^{13}$C NMR (125 MHz; CDCl$_3$) δ$_c$ 178.2, 170.8, 157.1, 151.6, 109.3, 106.7, 33.2, 32.7, 19.7, 17.8, 12.6; HRMS (ESI-TOF) m/z: [M–H]$^-$ calcd. for C$_{29}$H$_{51}$O$_6$Si$_2$ 551.3224; found 551.3214.

1-[5-(3,5-bis(triisopropylsilyloxy)phenoxy)-5-oxopentanoyl]-2-docosahexaenoyl-sn-glycero-3-phosphatidylcholine 24: LysoPC-DHA 21 (15 mg, 0.02 mmol) and the di-protected glutaric phloroglucinol 23 (16 mg, 0.02 mmol) were dissolved in dry CH$_2$Cl$_2$ (2 mL). DCC (6 mg, 0.03 mmol) and DMAP (1 mg, 8.30 µmol) were added to the solution and the reaction was stirred at room temperature for 24 h under nitrogen. The solvent was evaporated under reduced pressure and the residue obtained was purified on Sepak SiOH cartridge (CHCl$_3$/MeOH 100/0 to 60/40) to give the desired polyphenolic-PC-DHA 24 (19 mg, 65%) as an uncoloured oil. 33% of starting material (5 mg) were recovered during the purification.

R$_f$ (CHCl$_3$/MeOH/H$_2$O 65/25/4) 0.40; $^1$H NMR (500 MHz; CDCl$_3$) δ$_H$ 6.28 (t, J=2.5 Hz, 1H, CH$_{aro}$), 6.23 (t, J=2.5 Hz, 2H, CH$_{aro}$), 5.41-5.28 (m, 12H, CH=CH), 5.25-5.20 (m, 1H, CH—O), 4.43 (dd, J=3.0 Hz, J=12.0 Hz, 1H, CH$_{2(a)}$—O), 4.36-4.30 (m, 2H, CH$_2$—O), 4.17 (dd, J=6.5 Hz, J=12.0 Hz, 1H, CH$_{2(b)}$—O), 4.02-3.95 (m, 2H, CH$_2$—O), 3.80-3.77 (m, 2H, CH$_2$—N), 3.35 (s, 9H, (CH$_3$)$_3$—N$^+$), 2.84-2.79 (m, 10H, CH$_2$ bis-allylic), 2.57 (t, J=7.5 Hz, 2H, CH$_2$—C=O$_{(glut)}$), 2.43 (t, J=7.5 Hz, 2H, CH$_2$—C=O$_{(glut)}$), 2.39-2.35 (m, 4H, CH$_2$—C=O$_{(DHA)}$ and CH$_2$ allylic), 2.07 (quint, J=7.5 Hz, 2H, CH$_2$ allylic), 2.00 (quint, J=7.5 Hz, 2H, CH$_{2(glut)}$), 1.24-1.18 (m, 6H, CH—Si), 1.08 (d, J=7.5 Hz, 36H, (CH$_3$)$_2$C), 0.97 (t, J=7.5 Hz, 3H, CH$_3$); $^{13}$C NMR (125 MHz; CDCl$_3$) δ$_c$ 172.8, 172.7, 171.2, 157.4, 151.9, 132.2, 129.5, 128.7, 128.5, 128.5, 128.5, 128.3, 128.3, 128.2, 128.1, 128.0, 127.2, 109.5, 107.0, 70.8, 66.8, 63.4, 63.3, 59.4, 54.9, 34.3, 33.5, 33.2, 25.8, 25.8, 25.7, 22.8, 20.8, 20.1, 18.1, 14.5, 12.8; HRMS (ESI-TOF) m/z: [M+H]$^+$ calcd. for C$_{59}$H$_{101}$NO$_{12}$PSi$_2$ 1102.6594; found 1102.6608.

1-[5-(3,5-dihydroxyphenoxy)-5-oxopentanoyl]-2-docosahexaenoyl-sn-glycero-3-phosphatidylcholine 25: To a solution of 24 (17 mg, 0.01 mmol) in dry THF (0.50 mL), was added Et$_3$N-3HF (10 µL, 0.06 mmol). The reaction was stirred at room temperature during 4 h. The solvent was evaporated under reduced pressure and the residue obtained was purified on Sepak SiOH cartridge (CHCl$_3$/MeOH 100/0 to 80/20) to give the desired deprotected polyphenolic-PC-DHA 25 (10.20 mg, 84%) as an uncoloured oil.

R$_f$ (CHCl$_3$/MeOH/H$_2$O 65/25/4) 0.30; $^1$H NMR (500 MHz; CDCl$_3$) δ$_H$ 6.43 (s, 1H, CH$_{aro}$), 6.10 (s, 2H, CH$_{aro}$), 5.42-5.28 (m, 12H, CH=CH), 5.18-5.14 (m, 1H, CH—O), 4.42-4.37 (m, 1H, CH$_{2(a)}$—O), 4.21-4.13 (m, 3H, CH$_{2(b)}$—O and CH$_2$—O), 4.04-3.98 (m, 2H, CH$_2$—O), 3.52-3.46 (m, 2H, CH$_2$—N), 3.03 (s, 9H, (CH$_3$)$_3$—N$^+$), 2.84-2.81 (m, 10H, CH$_2$ bis-allylic), 2.56-2.51 (m, 2H, CH$_2$—C=O$_{(glut)}$), 2.46-2.41 (m, 2H, CH$_2$—C=O$_{(glut)}$), 2.37-2.33 (m, 4H, CH$_2$—C=O$_{(DHA)}$ and CH$_2$ allylic), 2.07 (quint, J=7.5 Hz, 2H, CH$_2$ allylic), 2.01-1.95 (m, 2H, CH$_{2(glut)}$), 0.97 (t, J=7.5 Hz, 3H, CH$_3$); $^{13}$C NMR (125 MHz; CDCl$_3$) δ$_c$ 172.7, 172.6, 172.1, 159.5, 152.5, 132.2, 129.5, 128.8, 128.5, 128.5, 128.5, 128.3, 128.3, 128.3, 128.1, 128.0, 127.2, 101.4, 101.2, 70.5, 66.1, 63.5, 62.3, 59.7, 54.0, 34.0, 33.1, 33.0, 25.9, 25.8, 25.8, 25.8, 22.8, 20.8, 20.4, 14.5; HRMS (ESI-TOF) m/z: [M+H]+ calcd. for $C_{41}H_{61}NO_{12}P$ 790.3931; found 790.3940; HPLC rt: 24.12 min, (Atlantis C18 5 μm (4.6×250 mm), A: MeOH/H$_2$O/ACN 90/35/2.5, B: MeOH/H$_2$O/ACN 100/4/2.5, $t_{0'=100/0}$, $t_{15'=100/0}$, $t_{30'=0/100}$, $t_{50'=0/100}$, detection 272 nm).

Example 5: Synthesis of EPA-Phloroglucinol Conjugate

Preparation of (5,8,11,14,17 Z)-3,5-dihydroxyphenyl icosa-5,8,11,14,17-pentaenoate Coupling of the di-TIPS-phloroglucinol 2 (652 mg, 1.48 mmol) and EPA (543 mg, 1.79 mmol) was performed according to the general procedure used in example 1 and afforded the protected phloroglucinol-EPA (753 mg, 70%) as an uncolored oil after purification on silica gel chromatography (hexane/AcOEt 99.7/0.3).

Deprotection of this protected EPA-phloroglucinol (830 mg, 1.15 mmol) was performed using the general procedure used in example 1 and afforded the (5,8,11,14,17 Z)-3,5-dihydroxyphenyl icosa-5,8,11,14,17-pentaenoate (455 mg, 96%) as an uncolored oil after purification on silica gel chromatography (hexane/AcOEt 9/1 to 7/3).

$R_f$ (hexane/AcOEt 7/3) 0.3; $^1$H NMR (500 MHz, CDCl$_3$) δ 6.09 (s, 3H), 5.46-5.30 (m, 10H), 2.85-2.80 (m, 8H), 2.57 (t, J=7.5 Hz, 2H), 2.20 (q, J=7.0 Hz, 2H), 2.10-2.05 (m, 2H), 1.83 (q, J=7.5 Hz, 2H), 0.97 (t, J=7.5 Hz, 3H); $^{13}$C NMR (126 MHz, CDCl$_3$) δ 173.8, 157.6, 152.0, 132.3, 129.5, 128.8, 128.5, 128.5, 128.5, 128.3, 128.3, 128.1, 127.2, 102.1, 101.4, 34.0, 26.7, 25.9, 25.8, 25.7, 24.8, 20.8, 14.5.

Example 6: Synthesis of Alkylated EPA-Phloroglucinol Conjugate

Preparation of (5,8,11,14,17 Z)-3-hydroxy-5-isopropoxyphenyl icosa-5,8,11,14,17-pentaenoate Coupling of the mono-TIPS-mono-isopropyl-phloroglucinol 11b (70 mg, 0.22 mmol) and EPA (65 mg, 0.22 mmol) was performed according to the general procedure used in example 1 and afforded the protected mono-isopropyl-phloroglucinol-EPA (71 mg, 54%) as an uncolored oil after purification on silica gel chromatography (hexane/AcOEt 99.5/0.5).

Deprotection of this protected EPA-phloroglucinol (65 mg, 0.11 mmol) was performed using the general procedure used in example 1 and afforded the (5,8,11,14,17 Z)-3-hydroxy-5-isopropoxyphenyl icosa-5,8,11,14,17-pentaenoate (37 mg, 76%) as an uncolored oil after purification on silica gel chromatography (hexane/AcOEt 9/1).

$R_f$ (hexane/AcOEt 9/1) 0.3; $^1$H NMR (500 MHz, CDCl$_3$) δ 6.22 (t, J=2.2 Hz, 1H), 6.18 (t, J=2.1 Hz, 1H), 6.14 (t, J=2.1 Hz, 1H), 5.64 (br, 1H), 5.48-5.28 (m, 10H), 4.44 (quint, J=6.0 Hz, 1H), 2.83-2.80 (m, 8H), 2.56- 2.53 (m, 2H), 2.21-2.17 (m, 2H), 2.12-2.02 (m, 2H), 1.82 (quint, J=7.5 Hz, 2H), 1.30 (d, J=6.0 Hz, 6H), 0.97 (t, J=7.5 Hz, 3H); $^{13}$C NMR (126 MHz, CDCl$_3$) δ 172.7, 159.8, 157.5, 152.3, 132.4, 129.4, 129.0, 128.9, 128.6, 128.5, 128.5, 128.4, 128.2, 127.3, 101.9, 101.9, 101.3, 70.6, 34.0, 26.8, 25.9, 25.9, 25.8, 25.8, 25.0, 22.2, 20.9, 14.6.

Example 7: Synthesis of Alkylated Docosanoic-Phloroglucinol Conjugate

Preparation of 3-hydroxy-5-isopropoxyphenyl docosanoate

Docosanoic acid (136.6 mg, 0.40 mmol) and the mono-TIPS-mono-isopropyl-phloroglucinol 11b (100 mg, 0.30 mmol) were dissolved in dry CH$_2$Cl$_2$ (6 mL) and dry DMF (1.5 mL). DCC (82.7, 0.40 mmol) and DMAP (5 mg, 0.04 mmol) were added to the solution and the reaction was stirred at room temperature for 5 h under nitrogen, and then overnight at 50° C. Then, the mixture was left 2 h at 4° C. to induce dicyclohexylurea crystallization. The urea residue was then filtered off, and the filtrate was washed with water and brine. The organic layer was dried on MgSO$_4$ and concentrated under reduced pressure. Purification of the crude material was performed by chromatography on silica gel (hexane/AcOEt 99.5/0.5) to afford (95 mg, 48%) the protected derivative as an uncolored oil.

Deprotection of this protected-docosanoic-phloroglucinol (90 mg, 0.14 mmol) was performed using the general procedure used in example 1 and afforded 3-hydroxy-5-isopropoxyphenyl docosanoate (56 mg, 82%) as white solid after purification on silica gel chromatography (hexane/AcOEt 9/1).

$R_f$ (hexane/AcOEt 9.5/0.5) 0.3; $^1$H NMR (500 MHz, CDCl$_3$) δ 6.22 (t, J=2.2 Hz, 1H), 6.17 (t, J=2.1 Hz, 1H), 6.14 (t, J=2.1 Hz, 1H), 6.07 (br, 1H), 4.44 (hept, J=6.1 Hz, 1H), 2.52 (t, J=7.6 Hz, 2H), 1.75-1.69 (m, 2H), 1.42-1.34 (m, 4H), 1.30 (d, J=6.1 Hz, 6H), 1.28-1.22 (m, 30H), 0.88 (t, J=7.0 Hz, 3H); $^{13}$C NMR (126 MHz, CDCl$_3$) δ 173.1, 159.8, 157.7, 152.4, 102.0, 101.9, 101.26, 70.6, 34.8, 32.3, 30.0, 30.0, 29.7, 29.8, 29.7, 29.6, 29.4, 25.2, 23.0, 22.3, 14.5.

Example 8: Preparation of (9,12,15Z)-3-hydroxy-5-isopropoxyphenyl octadeca-9,12,15-trienoate (PG-OiP-ALA)

(9,12,15Z)-3-isopropoxy-5-((triisopropylsilyl)oxy) phenyl octadeca-9,12,15-trienoate (34)

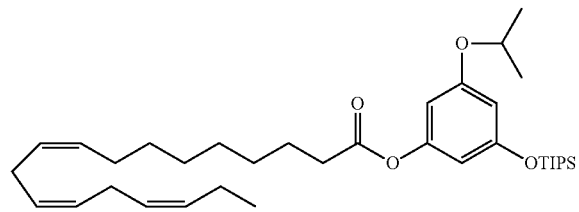

34

Coupling of the mono-TIPS-mono-isopropyl-phloroglucinol 11b (70 mg, 0.22 mmol) and ALA (60 mg, 0.22 mmol) was performed according to the general procedure used in example 1 and afforded the protected mono-isopropyl-phloroglucinol-ALA 34 (101 mg, 80%) as an uncolored oil after purification on silica gel chromatography (hexane/AcOEt 99.5/0.5).

$R_f$ (hexane/AcOEt 99/1) 0.2; $^1$H NMR (500 MHz, CDCl$_3$) δ 6.28 (t, J=2.1 Hz, 1H), 6.23 (t, J=2.1 Hz, 1H), 6.20 (t, J=2.1

Hz, 1H), 5.42-5.29 (m, 6H), 4.44 (sept, J=6.0 Hz, 1H), 2.82-2.80 (m, 4H), 2.50 (t, J=7.5 Hz, 2H), 2.11-2.04 (m, 4H), 1.72 (quint, J=7.5 Hz, 2H), 1.43-1.34 (m, 8H), 1.30 (d, J=6.0 Hz, 6H),1.27-1.19 (m, 3H), 1.09 (d, J=7.3 Hz, 18H), 0.97 (t, J=7.5 Hz, 3H); $^{13}$C NMR (126 MHz, CDCl$_3$) δ 172.3, 159.5, 157.7, 152.3, 132.3, 130.6, 128.6, 128.6, 128.1, 127.4, 106.4, 105.6, 102.7, 70.5, 34.8, 29.9, 29.5, 29.5, 29.4, 27.5, 25.9, 25.9, 25.2, 22.3, 20.9, 18.2, 14.6, 12.9.

(9,12,15Z)-3-hydroxy-5-isopropoxyphenyl octadeca-9,12,15-trienoate (35)

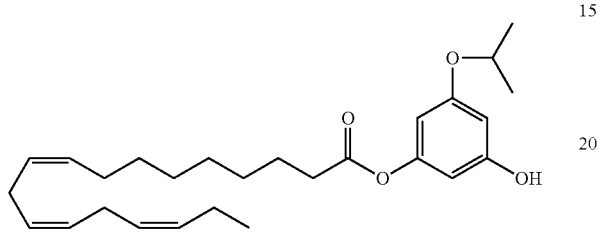

Deprotection of the protected ALA-phloroglucinol 34 (90 mg, 0.15 mmol) was performed using the general procedure used in example 1 and afforded coumpound 35 PG-OiP-ALA (56 mg, 58%) as an uncolored oil after purification on silica gel chromatography (hexane/AcOEt 9/1).

R$_f$ (hexane/AcOEt 8/2) 0.5; $^1$H NMR (500 MHz, CDCl$_3$) δ 6.22 (t, J=2.1 Hz, 1H), 6.17 (t, J=2.1 Hz, 1H), 6.13 (t, J=2.1 Hz, 1H), 5.87 (Br, 1H), 5.42-5.29 (m, 6H), 4.44 (sept, J=6.0 Hz, 1H), 2.82-2.80 (m, 4H), 2.52 (t, J=7.5 Hz, 2H), 2.11-2.04 (m, 4H), 1.73 (quint, J=7.5 Hz, 2H), 1.43-1.32 (m, 8H), 1.30 (d, J=6.0 Hz, 6H), 0.97 (t, J=7.5 Hz, 3H); $^{13}$C NMR (126 MHz, CDCl$_3$) δ 173.1, 159.8, 157.6, 152.3, 132.3, 130.6, 128.6, 128.6, 128.1, 127.4, 102.0, 101.9, 101.3, 70.6, 34.8, 29.9, 29.5, 29.4, 29.4, 27.5, 25.9, 25.8, 25.2, 22.2, 20.9, 14.6.

Example 9: Synthesis of Deuterated Fatty Acid-Alkyl-Phloroglucinol

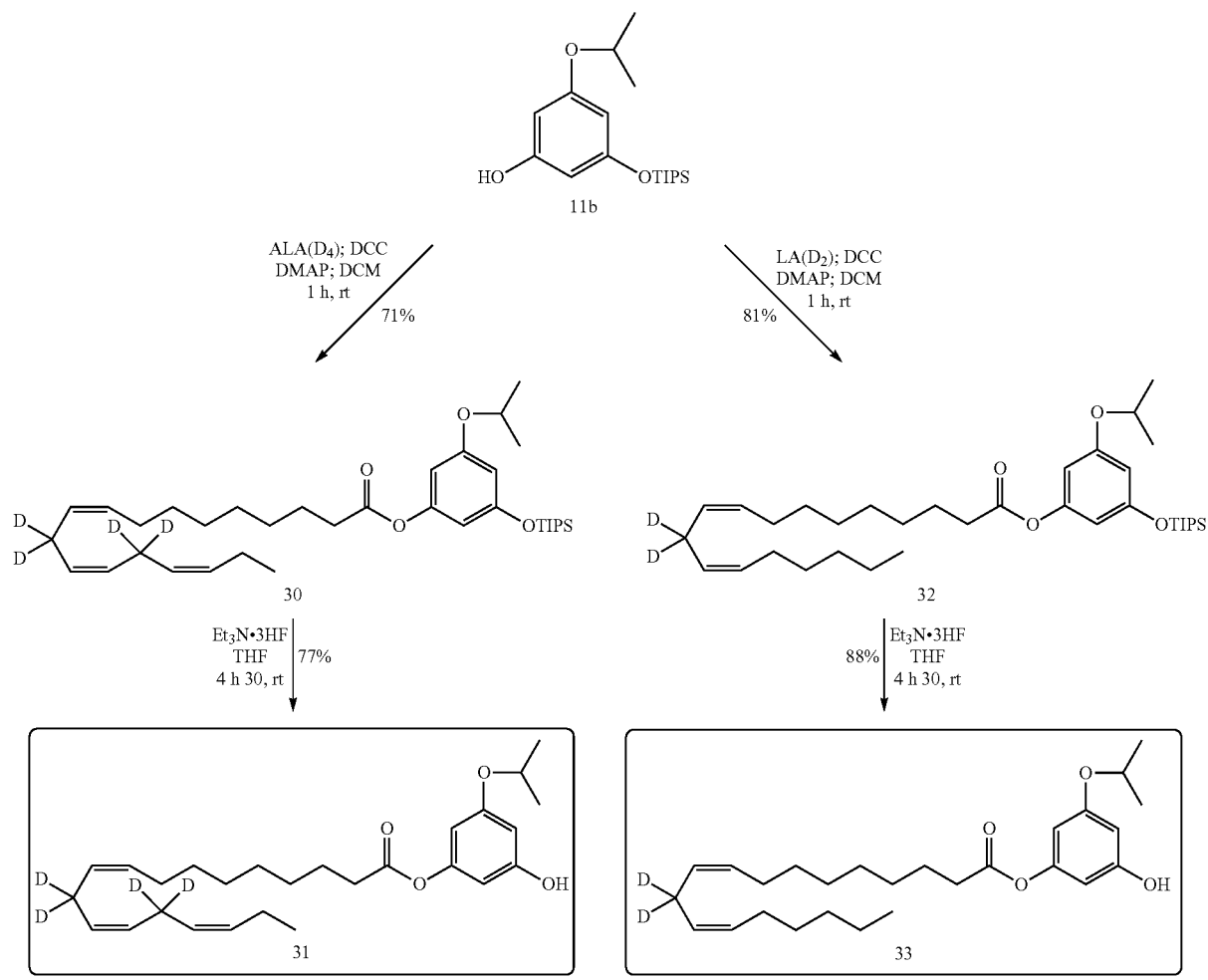

11,11,14,14-D₄-(9,12,15Z)-3-isopropoxy-5-((triisopropylsilyl)oxy)phenyl octadeca-9,12,15-trienoate (30)

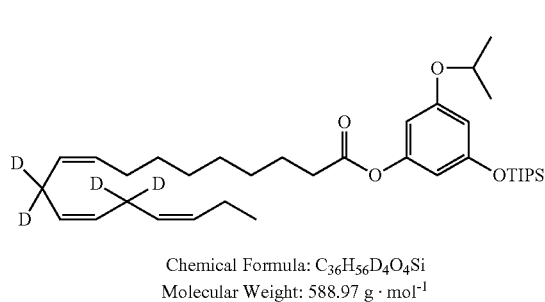

Chemical Formula: C₃₆H₅₆D₄O₄Si
Molecular Weight: 588.97 g·mol⁻¹

Coupling of the mono-TIPS-mono-isopropyl-phloroglucinol 11b (104 mg, 0.32 mmol) and ALA(D₄) (100 mg, 0.35 mmol) (ALA(D₄) was furnished by Retrotope company) was performed with the general procedure as explained in example 1 and afforded 30 (133 mg, 71%) as an uncolored oil after purification on silicagel chromatography (Cyclohexane/AcOEt 99/1).

$R_f$ (Hexane/AcOEt 95/5) 0.6; ¹H NMR (500 MHz, CDCl₃) δ 6.28 (t, J=2.2 Hz, 1H), 6.23 (t, J=2.1 Hz, 1H), 6.20 (t, J=2.1 Hz, 1H), 5.46-5.26 (m, 6H), 4.44 (hept, J=6.0 Hz, 1H), 2.51 (t, J=7.5 Hz, 2H), 2.15-1.99 (m, 4H), 1.80-1.65 (m, 2H), 1.45-1.32 (m, 8H), 1.31 (d, J=6.1 Hz, 6H), 1.29-1.19 (m, 3H), 1.10 (d, J=5.0 Hz, 19H), 0.98 (t, J=7.5 Hz, 3H); ¹³C NMR (126 MHz, CDCl₃) δ 132.10, 130.38, 128.30, 127.76, 127.12, 106.14, 105.41, 102.47, 22.09, 18.00, 14.40, 12.71.

11,11,14,14-D₄-(9,12,15Z)-3-hydroxy-5-isopropoxyphenyl octadeca-9,12,15-trienoate (31)

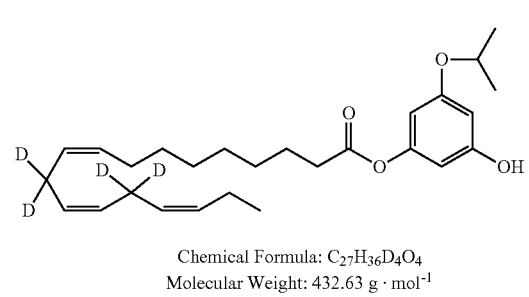

Chemical Formula: C₂₇H₃₆D₄O₄
Molecular Weight: 432.63 g·mol⁻¹

Deprotection of the protected ALA(D₄)-mono-isopropyl-phloroglucinol 30 (120 mg, 0.20 mmol) was performed through the general procedure as explained in exsample 1 and afforded 31 (67 mg, 77%) as an uncoloured oil after purification on silica gel chromatography (Cyclohexane/AcOEt 95/5).

$R_f$ (Hexane/AcOEt 90/10) 0.19; ¹H NMR (500 MHz, CDCl₃) δ 6.22 (t, J=2.2 Hz, 1H), 6.17 (t, J=2.1 Hz, 1H), 6.13 (t, J=2.1 Hz, 1H), 5.97 (s, 1H), 5.45-5.28 (m, 6H), 4.44 (hept, J=6.1 Hz, 1H), 2.53 (t, J=7.6 Hz, 2H), 2.18-1.97 (m, 4H), 1.81-1.65 (m, 2H), 1.44-1.32 (m, 8H), 1.30 (d, J=6.1 Hz, 6H), 0.98 (t, J=7.5, 3H); ¹³C NMR (126 MHz, CDCl₃) δ 172.94, 159.60, 157.44, 152.13, 132.10, 130.37, 128.33, 128.28, 127.78, 127.12, 101.77, 101.74, 101.10, 70.41, 34.55, 29.69, 29.26, 29.21, 29.16, 27.31, 24.99, 22.04, 20.67, 14.41.

11,11-D₂-(9,12Z)-3-isopropoxy-5-((triisopropylsilyl)oxy)phenyl octadeca-9,12-dienoate (32)

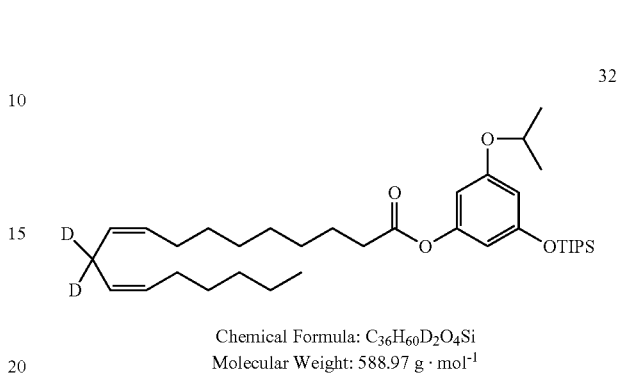

Chemical Formula: C₃₆H₆₀D₂O₄Si
Molecular Weight: 588.97 g·mol⁻¹

Coupling of the mono-TIPS-mono-isopropyl-phloroglucinol 11b (104 mg, 0.32 mmol) and LA(D₂) (100 mg, 0.35 mmol) (LA(D₂) was furnished by Retrotope company) was performed with the general procedure of example 1 and afforded 32 (153 mg, 81%) as an uncolored oil after purification on silica gel chromatography (Cyclohexane/AcOEt 99/1).

$R_f$ (Hexane/AcOEt 95/5) 0.75; ¹H NMR (500 MHz, CDCl₃) δ 6.28 (t, J=2.2 Hz, 1H), 6.23 (t, J=2.1 Hz, 1H), 6.20 (t, J=2.1 Hz, 1H), 5.45-5.27 (m, 4H), 4.44 (hept, J=6.1 Hz, 1H), 2.51 (t, J=7.5 Hz, 2H), 2.12-1.99 (m, 4H), 1.74-1.71 (m, 2H), 1.46-1.17 (m, 23H), 1.09 (d, J=7.2 Hz, 18H), 0.89 (t, J=7.0 Hz, 3H); ¹³C NMR (126 MHz, CDCl₃) δ 172.05, 159.23, 157.47, 152.12, 130.37, 130.17, 128.07, 127.90, 106.14, 105.41, 102.47, 70.26, 34.54, 31.64, 29.72, 29.47, 29.29, 29.23, 29.19, 27.32, 27.31, 25.02, 22.69, 22.09, 18.00, 17.99, 14.19, 12.72, 12.71.

11,11-D₂-(9Z,12Z)-3-hydroxy-5-isopropoxyphenyl octadeca-9,12-dienoate (33)

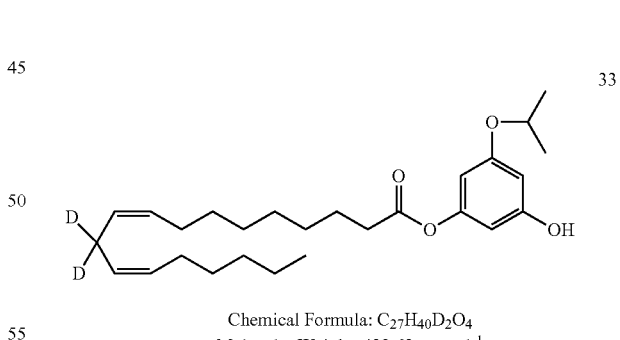

Chemical Formula: C₂₇H₄₀D₂O₄
Molecular Weight: 432.63 g·mol⁻¹

Deprotection of the protected LA(D₂)-mono-isopropyl-phloroglucinol 32 (130 mg, 0.22 mmol) was performed through the general procedure as explained in example 1 and afforded 33 (84 mg, 88%) as an uncoloured oil after purification on silica gel chromatography (Cyclohexane/AcOEt 95/5).

$R_f$ (Hexane/AcOEt 90/10) 0.23; ¹H NMR (500 MHz, CDCl₃) δ 6.22 (t, J=2.2 Hz, 1H), 6.17 (t, J=2.1 Hz, 1H), 6.13 (t, J=2.1 Hz, 1H), 5.89 (s, 1H), 5.46-5.28 (m, 4H), 4.44 (hept, J=6.1 Hz, 1H), 2.56-2.49 (m, 2H), 2.11-1.99 (m, 4H), 1.73 (m, 2H), 1.47-1.32 (m, 10H), 1.30 (d, J=10.0, 6H), 0.89 (t, J=7.0, 3H); $^{13}$C NMR (126 MHz, CDCl$_3$) δ 172.93, 159.62, 157.43, 152.15, 130.39, 130.17, 128.09, 127.91, 101.78, 101.76, 101.10, 70.41, 34.56, 31.64, 29.72, 29.47, 29.27, 29.22, 29.17, 27.33, 27.31, 25.01, 22.70, 22.05, 14.20.

Example 10: Effect of Lipophenol on All-Trans-Retinal Toxicity in ARPE-19 Cell Line In order to evaluate the ability of lipophenols to protect cells against all-trans-retinal toxicity, the synthesized derivatives were incubated in retinal pigment epithelium (ARPE-19 cell lines) cell cultures. The biological assay is based on the measure of cell survival after treatment with the lipophenol prior incubation (pre-incubation process) with the carbonyl stressor AtR. The toxic AtR concentration (25 μM) was determined to reduce cell survival by 60 to 70%. The effect of lipophenols on cell viability at 10 μM and 40 μM are presented in table 1 and FIG. 12. Results are expressed as % of cell survival in treated (lipophenol/all-trans-retinal) vs untreated cells (taken as 100%).

ARPE-19 cells were obtained from ATCC and grown following the instructions in Dulbecco's Modified Eagle's Medium (DMEM)/Ham'F12 (GIBCO) containing 10% (v/v) Foetal Bovine Serum, 1% (v/v) antibiotics at 95% air/5% CO$_2$ atmosphere at 37° C. ARPE-19 cells were settled in 96-well plates (3×10$^4$ cells/well) and cultured 24 h to reach confluence before drug treatment. Cell cultures received a serum-free medium containing drugs at different concentrations (10-40 μM) for one hour and trans-retinal (25 μM) was added for 4 more hours before rinsing with medium. The viability of cells in triplicate samples was determined 16-20 h after with a MTT colorimetric assay. After 2 h incubation with 0.5 mg/ml MU, insoluble purple formazan produced was dissolved in DMSO. The absorbance at 570 nm and 655 nm of individual wells was measured by a microplate reader (BioRad 550). The percentage of viable cells was calculated as [(OD570 sample–OD655 sample)/(OD570 control–OD655 control)]×100, controls corresponding of cells incubated with 0.2% DMSO and 0.14% DMF.

Table 1 hereafter shows the results of ARPE-19 cell viability in the presence of lipophenol and AtR.

|  | % Survival | n |
|---|---|---|
| Untreated cell | 100 | |
| AtR (25 μM) | 29.1 ± 5.4 | 7 |

| Compounds | [a] % Survival 10 μM | [a] % Survival 40 μM | n |
|---|---|---|---|
| Phloroglucinol | 35.5 ± 3.3 | 41.6 ± 9.2 | 3 |
| Compound 8 | 33.3 ± 4.1 | 47.7 ± 3.2 | 3 |
| Compound 13a | 32.6 ± 3.7 | 44.9 ± 1.9 | 3 |
| Compound 13b | 43.2 ± 7.5 | 66.8 ± 8.6 | 4 |
| Compound 9b | 30.6 ± 1.2 | 32.7 ± 1.8 | 3 |
| DHA | 23.5 ± 2.7 | 7.3 ± 5.0 | 3 |
| DHA + 9b | 29.0 ± 1.7 | 10 ± 2.6 | 3 |

[a] Incubation of lipophenols 1 h followed by AtR incubation at 25 μM during 4 h. Cell viability is measured by MTT assay after 16-20 h. Each experiment have been performed in triplicate The biological evaluation showed the phloroglucinol to be moderately to weakly active with an increase of RPE cell survival of 10% at 40 μM.

Increasing DHA parts, leads to active derivatives able to reach 50% of cell survival as observed for 8 (PG-TriDHA). Mono DHA-alkylated lipophenol 13a revealed to be as active as 8. The highest increase of viability (70%) was observed for 13b (mono-isopropyl derivative) in a dose-dependent manner (FIG. 1).

To confirm the interest in the conception of the lipophenol conjugate 13b, a mixture of DHA and mono-isopropyl phloroglucinol 9b was evaluated (in the same conditions) and presented an important toxicity, comparable to what is observed by treatment with DHA alone. This result strongly supports that introduction of a PUFA moiety on the O-alkylated-polyphenol backbone, is a promising approach to obtain potent derivatives.

Example 11: Biological Assessment of the Protective Effects of Phloroglucinol-Isopropyl-DHA (Compound 13b) Against All-Trans-Retinal-Induced Carbonyl and Oxidative Stresses in the Retina Following light stimulation, the visual chromophore 11-cis-retinal, which is covalently linked to photoreceptor opsins to form the visual pigments (rhodopsin), is photoisomerase to all-trans-retinal (atRal). This latter triggers the phototransduction through activation of the opsin before being released in the photoreceptor outer segment (POS) disc membranes. An excess of free all-trans-retinal following high level exposal to light is very reactive with amines and may cause both acute carbonyl and oxidative stresses. This accumulation of retinal worsens when loss-of-function mutations in the ABCA4 and/or RDH8/12 genes, which encode protein partners releasing retinal from the membrane and reducing it to retinol, are present in patients with retinopathies. The retinal pigment epithelium (RPE), whose apical microvilli are juxtaposed to the POS, contributes to the renewal of POS by daily phagocytosis. The latter will lead to lipofuscin accumulation and its excessive levels eventually cause RPE death as part of the pathophysiological process in several sight-threatening diseases such as Stargardt disease and age-related macular degeneration. The bisretinoid derivatives (RALdi, A2E) formation in the lipofuscin can contribute to generation of non-degradable material and be toxic to RPE again through oxidative and carbonyl stress.

Cytoprotective Action of Compound 13b in Neural Retina Cell Cultures

The effect of compound 13b on cell viability was examined after co-incubation with atRal. Cell cultures were incubated with 13b (10 to 100 μM) and atRal (50-75-100 μM) was added 1 h after for a 4 h co-incubation. Cells were then cultured in serum-free medium for 16-20 h and their viability was determined with a MTT assay. It was found that all atRal concentrations caused cytotoxicity that was robustly reversed by 13b treatment in a dose-dependent manner (FIG. 2). Therefore, it was demonstrated that the cytotoxicity of atRal on neural retina could be efficiently neutralized by an alkylated-phloroglucinol-DHA conjugate.

Mitochondrial Respiration

Oxidative stress originates from physiological reactions taking place practically inside each cell of an organism. The production of reactive oxygen species (ROS) accompanies, for example, oxidative phosphorylation-derived ATP-based energy metabolism which takes place in the mitochondria of a cell. Under physiological conditions, ROS are neutralized by effective enzymatic and non-enzymatic defense mechanisms, contributing to the maintenance of a proper balance.

However, an excess of ROS, resulting from their overproduction in pathophysiological conditions, will disturb the equilibrium and lead eventually to deleterious consequences for the cell. Maeda et al. (JBC 284(22), 2009) have reported that atRal impairs mitochondrial oxidative phosphorylation. Therefore, mitochondrial respiration was measured in ARPE-19 cell line using oxygraph after exposure to 25 µM atRal and/or 40 µM 13b (FIG. 3). AtRal strongly inhibits the activity of complexes CI and CII while 13b partially reverse this inhibition, 13b showing no significant inhibition of the activity of each complex.

Such results confirmed the mitochondrial poisoning by atRal and the rescue by phloroglucinol-isopropyl-DHA.

Example 12: Protective Activity of Lipophenol Conjugates against atRAL in RPE Cells (ARPE-19 Cell Line and RPE Primary Cultures)

Protective Effects of Lipophenols on ARPE-19 Cell Lines in the Presence of atRAL (25 µM)

Further to the results of examples 10 and 11, the lipophenols of the invention were incubated in retinal pigment epithelium (ARPE-19 cell lines) cell cultures and the biological assay is based on the measure of cell survival after treatment with the lipophenol prior incubation for 4 hours with the carbonyl stressor AtR at 25 µM (co-treatment process).

Co-treatment were performed with lipophenols onto ARPE-19 (FIG. 4). Incubation for 4 h with atRAL decreased cell viability to 35%. The protection of ARPE-19 by phloroglucinol (PG) was dose-dependent but weak (less than 10%). In contrast, most of the PG derivatives were more protective, in particular the presence of two or three DHA linked to PG provided a strong protection (up to 73% survival), as well as the mono-alkylation (methyl and isopropyl) were sufficient to protect 60% of cells. PG-OiP-DHA was confirmed to be among the most efficient (74%). Interestingly, resveratrol-DHA was also very potent, whereas DHA appeared to be toxic.

Mitochondrial Enzymatic Activities and Protein Expression

In a cellular context, PG-OiP-DHA (compound 13b) has been shown able to partially restore mitochondrial oxidative respiration impaired by the atRAL (example 10). Because this repair might be produced by targeting the whole oxidative chain or each individual respiratory complex, this potency was further investigated by measuring the intrinsic activity of each mitochondrial respiratory chain (MRC) complex (enzymology) and their level of protein expression (FIG. 5). The enzymatic activities indicated that complex II and IV were affected by atRAL and significantly preserved by PG-OiP-DHA. Citrate synthase (CS) activity markedly dropped with atRAL treatment, suggesting a loss of mitochondrial mass related to necrotic cell death. This was supported by the loss of MRC protein expression. Altogether, PG-OiP-DHA showed a protective effect on the mitochondrial activity.

Characterization of atRAL-Induced Cell Death

Further investigations were made to define the atRAL-induced cell death (apoptotic versus necrotic) and validate the protective effect of PG-OiP-DHA (FIG. 6). Cells were incubated for 4 h with atRAL 25 µM, PG-OiP-DHA (compound 13b) 40 µM, or both. Treated ARPE-19 were labeled with Annexin V-FITC (A) and propidium iodide (PI) to separate by flow cytometry healthy cells (no labeling), early apoptosis (A+ and PI−) and necrotic cells (A+ and PI+). In CTL or PG-OiP-DHA-treated cells only 6 to 10% died. After 4 h atRAL, cell death reached 46%, mainly at necrotic stage (41%). Co-incubation with PG-OiP-DHA markedly reduced both the total cell death (18%) and the necrotic cells (16%).

Primary RPE Cultures a. Pre-treatment 24 h, $H_2O_2$ 450 µM 2 h; cell viability assay To compare the anti-oxidant efficacies of phloroglucinol (10% gain of survival) and PG-OiP-DHA (20%) in the RPE (FIG. 7). These results suggest that both contributed by pre-treatment to reduce the $H_2O_2$-induced oxidative damage, and PG-OiP-DHA appears to be more protective in primary RPE cells.

b. Pre-treatment 24 h, atRAL 25 µM 4 h; cell viability assay

To compare the anti-carbonyl efficacies of phloroglucinol (18% gain of survival) and PG-OiP-DHA (42%) in the RPE (FIG. 8). These results suggest that both contributed by pre-treatment to reduce the atRAL-induced cell damage, and PG-OiP-DHA appears to be more protective at higher concentrations, in primary RPE cells.

c. Co-incubation 4 h with atRAL 25 µM; cell viability assay

To compare the anti-carbonyl efficacies of phloroglucinol (22% gain of survival) and PG-OiP-DHA (69%) in a condition to probe their scavenging properties in primary RPE cells (FIG. 9). These results show that both contributed by co-treatment to reduce the atRAL-induced cell damage, and PG-OiP-DHA appears to be more protective at lower concentrations.

Example 13: Effect of the Polyunsaturated Fatty Acid (PUFA) and Isopropyl Alkylation for the Protection Effect of the Presence of a PUFA Residue Some experiments (in ARPE-19 cell lines) were made to compare the anti-carbonyl efficacies of PG-OiP-ALA (C18:3 ω-3)(compound 35), PG-OiP-EPA (C20:5 ω-3) (compound of example 6), PG-OP-DHA (C22:6 ω-3)(compound 13b), and saturated C22 (compound of example 7) (FIGS. 10 and 11).

The rank of efficacy was DHA>EPA=ALA>C22, demonstrating that the presence of PUFA was most advantageous for the activity. However there was no correlation between the efficacy and the number or the position of double bounds.

Effect of the Presence of an Alkyl Group

Several experiments (in ARPE-19 cell lines) were made to study the effect of the presence of an alkyl group, in particular of an isopropyl group.

These experiments compare the anti-carbonyl efficacies of PG-EPA and PG-DHA (without alkyl part) and the corresponding PG-OiP-EPA and PG-OiP-DHA (FIG. 13). Whatever the PUFA, isopropyl was necessary for the proper protection.

Mitochondrial Enzymatic Activities and MRC Protein Expression

Several experiments were made to validate the efficacy of PG-OiP-DHA in the protection of the mitochondrial activity (FIG. 14). The enzymatic activities indicated that complex II and IV were affected by atRAL and significantly preserved by PG-OP-DHA. These results were supported by the analysis of MRC protein expression (FIG. 15).

The invention claimed is:

1. A method for treating a retinal pathology caused by either or both carbonyl and oxidative stress, comprising a step of administering to a patient in need thereof a pharmaceutically acceptable amount of a compound of formula (I):

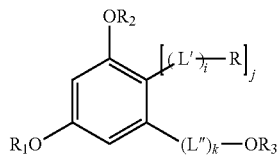
(I)

wherein:
i is 0 or 1;
j is 0 or 1;
k is 0 or 1;
$R_1$ is chosen from the group consisting of: H, $(C_1\text{-}C_{12})$ alkyl, $(C_3\text{-}C_6)$cycloalkyl, and $(C_6\text{-}C_{10})$aryl radicals; or $R_1$ may form a heterocycloalkyl radical with the oxygen atom bearing it; or $R_1$ is a group of formula C(O)R, R being as defined below;
$R_2$ is chosen from the group consisting of: H, $(C_1\text{-}C_{12})$ alkyl, $(C_3\text{-}C_6)$cycloalkyl, and $(C_6\text{-}C_{10})$aryl radicals; or $R_2$ may form a heterocycloalkyl radical with the oxygen atom bearing it; or $R_2$ is a group of formula C(O)R, R being as defined below;
R is a, linear or branched, alkyl radical, possibly interrupted by one or several double bonds, comprising at least 19 carbon atoms, and wherein one or several hydrogen atoms may be replaced by deuterium atoms;
$R_3$ is H and k=0 when j=1; or, when j=0, $R_3$ is a group of formula —C(O)R or -L-C(O)R, R being as defined above;
L is a linker having one of the following formulae (L1) or (L2):

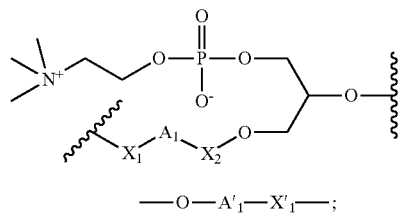

wherein:
$A_1$ is an alkylene radical comprising from 3 to 6 carbon atoms;
$A'_1$ is an alkylene radical comprising from 1 to 6 carbon atoms, optionally interrupted by one or several heteroatoms, such as oxygen atoms;
$X_1$ is a radical —C(O)— or an alkylene radical comprising from 1 to 6 carbon atoms;
$X_2$ is a radical —C(O)— or an alkylene radical comprising from 1 to 6 carbon atoms;
$X'_1$ is chosen from the group consisting of: —O—, —N($R_a$)— or an alkylene radical comprising from 1 to 6 carbon atoms, optionally interrupted by one or several heteroatoms, such as oxygen atoms, $R_a$ being H or an alkyl group comprising from 1 to 6 carbon atoms;
L' is a linker of formula $-(A)_p\text{-}(X)_q\text{—}C(O)\text{—}$, wherein:
p is 0 or 1;
q is 0 or 1;
A is an alkylene radical comprising from 1 to 6 carbon atoms, optionally interrupted by one or several heteroatoms, such as oxygen atoms,
X is —O—, —N($R_b$)— or an alkylene radical comprising from 1 to 6 carbon atoms, $R_b$ being H or an alkyl group comprising from 1 to 6 carbon atoms;
L" is a linker chosen from the group consisting of: $(C_6\text{-}C_{10})$arylene, $(C_1\text{-}C_{12})$alkylene, $(C_1\text{-}C_{12})$alkylene-$(C_6\text{-}C_{10})$arylene, $(C_6\text{-}C_{10})$arylene-$(C_1\text{-}C_{12})$alkylene, —CH=CH-$(C_6\text{-}C_{10})$arylene and $(C_1\text{-}C_{12})$alkylene-CH=CH-$(C_6\text{-}C_{10})$arylene radicals;
wherein, when j=0, at least one of the groups $R_1$, $R_2$ and $R_3$ comprises a radical R; provided that the compound of formula (I) is other than the following compound:

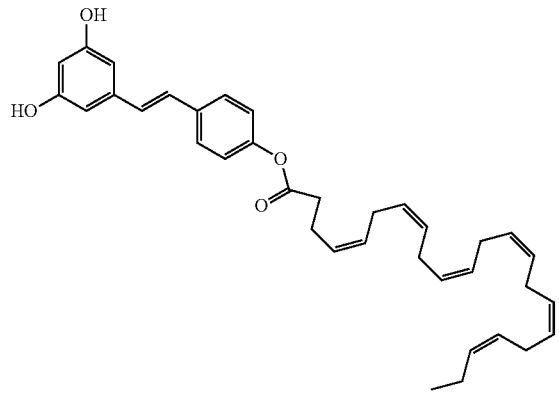 [SMILES: CC/C=C\C/C=C\C/C=C\C/C=C\C/C=C\C/C=C\CCC(=O)Oc1ccc(/C=C/c2cc(O)cc(O)c2)cc1]

or its pharmaceutically acceptable salts, racemates, diastereomers or enantiomers.

2. The method of claim 1, wherein, in formula (I), when j=0, at most one of the groups $R_1$, $R_2$ and $R_3$ is H.

3. The method of claim 1, comprising a step of administering a compound having the following formula (I-1):

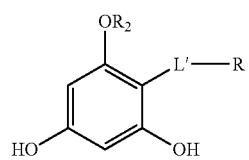
(I-1)

wherein L', R and $R_2$ are as defined in claim 1,
or its pharmaceutically acceptable salts, racemates, diastereomers or enantiomers.

4. The method of claim 1, comprising a step of administering a compound having the following formula (I-2):

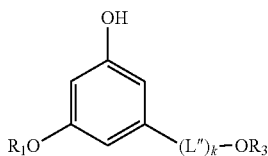
(I-2)

wherein k, L", $R_1$ and $R_3$ are as defined in claim 1, or its pharmaceutically acceptable salts, racemates, diastereomers or enantiomers.

5. The method of claim 4, wherein, in formula (I-2), $R^1$ is an alkyl group.

6. The method of claim 1, comprising a step of administering a compound having the following formula (I-2-1):

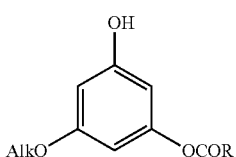
(I-2-1)

wherein Alk is a $(C_1-C_{12})$alkyl group, and R is as defined in claim 1, or its pharmaceutically acceptable salts, racemates, diastereomers or enantiomers.

7. The method of claim 1, comprising a step of administering a compound having the following formula (I-3):

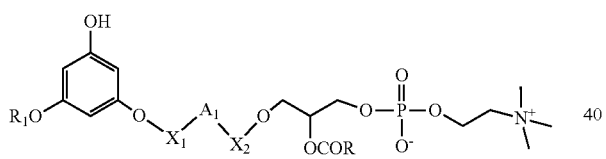
(I-3)

wherein $A_1$, $X_1$, $X_2$, R, and $R_1$ are as defined in claim 1, or its pharmaceutically acceptable salts, racemates, diastereomers or enantiomers.

8. The method of claim 1, comprising a step of administering a compound having the following formula (I-4):

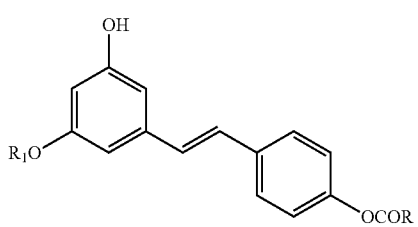
(I-4)

wherein R is as defined in claim 1, and $R_1$ is an alkyl group comprising from 1 to 12 carbon atoms, or its pharmaceutically acceptable salts, racemates, diastereomers or enantiomers.

9. The method of claim 1, comprising a step of administering a compound having the following formula (I-4-2):

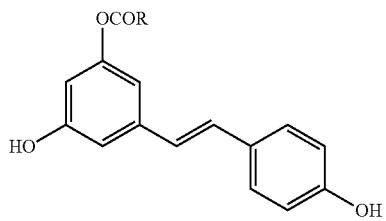
(I-4-2)

wherein R is as defined in claim 1, or its pharmaceutically acceptable salts, racemates, diastereomers or enantiomers.

10. The method of claim 1, wherein, in formula (I), $R_1$ is a $(C_1-C_{12})$alkyl group.

11. The method of claim 1, wherein, in formula (I), $R_1$ is a $(C_1-C_6)$alkyl group.

12. The method of claim 1, wherein, in formula (I), $R_1$ is an isopropyl group.

13. The method of claim 1, wherein, in formula (I), R is a linear or branched alkyl group, possibly interrupted by one or several double bonds, comprising from 19 to 23 carbon atoms.

14. The method of claim 1, wherein, in formula (I), R is a linear or branched alkyl group, possibly interrupted by one or several double bonds, comprising from 19 to 23 carbon atoms, and wherein one or several hydrogen atoms are replaced by deuterium atoms.

15. The method of claim 1, wherein, in formula (I), R is a linear or branched alkyl group, interrupted by at least one double bond, comprising from 19 to 21 carbon atoms.

16. The method of claim 1, wherein, in formula (I), R is the following radical:

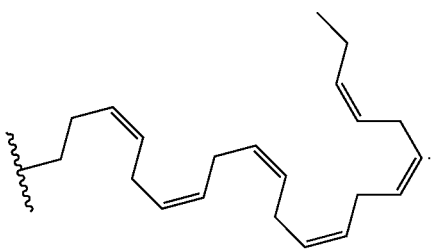 [SMILES: *CC/C=C\C/C=C\C/C=C\C/C=C\C/C=C\C/C=C\CC]

17. The method of claim 1, wherein, in formula (I), R is the following radical:

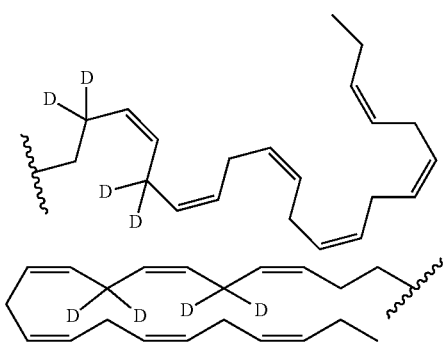

18. The method of claim 1, wherein the retinal pathology is Age-related Macular Degeneration (AMD) or Stargardt disease.

\* \* \* \* \*